United States Patent
Dakin et al.

(10) Patent No.: US 8,901,307 B2
(45) Date of Patent: Dec. 2, 2014

(54) CHEMICAL COMPOUNDS 251

(75) Inventors: Leslie Dakin, Waltham, MA (US); James Edward Dowling, Waltham, MA (US); Michelle Lamb, Waltham, MA (US); Jon Read, Waltham, MA (US); Xiaolan Zheng, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 795 days.

(21) Appl. No.: 13/000,138

(22) PCT Filed: Jul. 2, 2009

(86) PCT No.: PCT/GB2009/050773
§ 371 (c)(1),
(2), (4) Date: May 25, 2011

(87) PCT Pub. No.: WO2010/001169
PCT Pub. Date: Jan. 7, 2010

(65) Prior Publication Data
US 2011/0218182 A1  Sep. 8, 2011

Related U.S. Application Data

(60) Provisional application No. 61/183,278, filed on Jun. 2, 2009, provisional application No. 61/077,639, filed on Jul. 2, 2008.

(51) Int. Cl.
| | | |
|---|---|---|
| *C07D 417/10* | (2006.01) | |
| *A61K 31/454* | (2006.01) | |
| *C07D 417/14* | (2006.01) | |
| *A61K 31/427* | (2006.01) | |
| *C07D 277/34* | (2006.01) | |
| *C07D 417/06* | (2006.01) | |
| *A61K 31/426* | (2006.01) | |

(52) U.S. Cl.
CPC ............ *C07D 417/10* (2013.01); *C07D 417/14* (2013.01); *A61K 31/427* (2013.01); *C07D 277/34* (2013.01); *C07D 417/06* (2013.01); *A61K 31/426* (2013.01)
USPC .......................................... 546/209; 514/326

(58) Field of Classification Search
CPC ............................ C07D 417/10; A61K 31/454
USPC .......................................... 546/209; 514/326
See application file for complete search history.

(56) References Cited

U.S. PATENT DOCUMENTS

| | | |
|---|---|---|
| 6,730,687 B1 | 5/2004 | Miyachi et al. |
| 2002/0120144 A1 | 8/2002 | Akama et al. |
| 2006/0019956 A1 | 1/2006 | Green |

FOREIGN PATENT DOCUMENTS

| | | |
|---|---|---|
| EP | 0565135 A1 | 10/1993 |
| EP | 0676398 B1 | 10/1995 |
| EP | 0976748 B1 | 2/2000 |
| JP | 09003067 A1 | 1/1997 |
| WO | 97/22596 A1 | 6/1997 |
| WO | 97/30035 A1 | 8/1997 |
| WO | 97/32856 A1 | 9/1997 |
| WO | 98/13354 A1 | 4/1998 |
| WO | WO 98/14433 A1 | 4/1998 |
| WO | 99/02166 A1 | 1/1999 |
| WO | 00/40529 A1 | 7/2000 |
| WO | 00/41669 A2 | 7/2000 |
| WO | WO 01/02377 A1 | 1/2001 |
| WO | 01/34133 A2 | 5/2001 |
| WO | 01/92224 A1 | 12/2001 |
| WO | 02/04434 A1 | 1/2002 |
| WO | 02/08213 A1 | 1/2002 |
| WO | 2004/007491 A1 | 1/2004 |
| WO | 2004/093809 A2 | 11/2004 |
| WO | 2006/069186 A2 | 6/2006 |
| WO | 2009/064486 A9 | 5/2009 |

OTHER PUBLICATIONS

Dakin et al., "Discovery of Novel Benzylidene-1,3-thiazolidine-2,4-diones as Potent and Selective Inhibitors of the PIM-1, PIM-2 and PIM-3 Protein Kinases", Bioorganic & Medicinal Chemistry Letters 22: 4599-4604 (2012).
English language translation of abstract from foreign document No. JP09003067, 1997.
Ottana et al., "In vitro Antiproliferative Activity Against Human Colon Cancer Cell Lines of Representative 4-thiazolidinones. Part I", Bioorganic & Medicinal Chemistry Letters 15: 3930-3933 (2005).
Xia et al., "Synthesis and Evaluation of Novel Inhibitors of PIM-1 and PIM-2 Protein Kinases", Journal of Medicinal Chemistry 52: 74-86 (2009).
Arunesh et al., 'Small molecule inhibitors of PIM1 kinase: Jul. 2009 to Feb. 2013 patent update', Expert Opin. Ther. Patents (2014); 24; 1; 5-17.

(Continued)

*Primary Examiner* — Rebecca Anderson

(57) ABSTRACT

The invention relates to chemical compounds of formula (I), and salts thereof. In some embodiments, the invention relates to inhibitors or modulators of PIM-1 and/or PIM-2, and/or PIM-3 protein kinase activity or enzyme function. In still further embodiments, the invention relates to pharmaceutical compositions comprising compounds disclosed herein, and their use in the prevention and treatment of PIM kinase related conditions and diseases, preferably cancer.

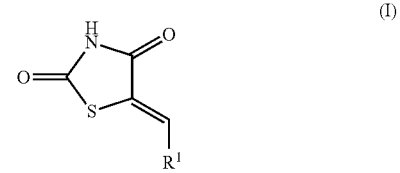

(I)

5 Claims, No Drawings

(56) References Cited

OTHER PUBLICATIONS

Chen et al, 'Synthesis and Biological Evaluation of Thiazolidine-2,4-dione and 2,4-thione Derivatives as Inhibitors of Translation Initiation', Bioorganic & Medicinal Chemistry Letters (2004); 14; 5401-5405.

Dhanasekaran et al, 'Delineation of Prognostic Biomarkers in Prostate Cancer', Nature (2001); 412; 822-826.

Knight et al., 'Discovery of GSK2126458, a Highly Potent Inhibitor of PI3K and the Mammalian Target of Rapamycin', ACS Medicinal Chemistry Letters (2010); 1; 39-43.

Li et al., 'Pim-3, A Proto-Oncogene with Serine/Threonine Kinase Activity, is Aberrantly Expressed in Human Pancreatic Cancer and Phosphorylates Bad to Block Bad-Mediated Apoptosis in Human Pancreatic Cancer Cell Lines', Cancer Research (2006); 66; 6741-6747.

Pomel et al., 'Furan-2-ylmethylene Thiazolidinediones as Novel, Potent, and Selective Inhibitors of Phosphoinositide 3-Kinase' Journal of Medicinal Chemistry (2006); 49; 3857-3871.

Richardson et al., 'Discovery of a potent CDK2 inhibitor with a novel binding mode, using virtual screening and initial, structure-guided lead scoping', Bioorganic & Medicinal Chemistry Letters (2007); 17; 3880-3885.

CHEMICAL COMPOUNDS 251

CROSS-REFERENCE TO RELATED APPLICATIONS

This application is a US National Stage under 35 U.S.C §371 of International Application No. PCT/GB2009/050773 (filed on Jul. 2, 2009, ) which claims priority under 35 U.S.C. §119(e) to Application No. 61/077,639 filed on Jul. 2, 2008, and 61/183,278, filed on Jun. 2, 2009.

FIELD OF INVENTION

The invention relates to chemical compounds of formula I,

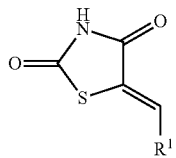

formula I and salts thereof. In some embodiments, the invention relates to inhibitors or modulators of PIM-1 and/or PIM-2, and/or PIM-3 protein kinase activity or enzyme function. In still further embodiments, the invention relates to pharmaceutical compositions comprising compounds disclosed herein, and their use in the prevention and treatment of PIM kinase related conditions and diseases, preferably cancer.

BACKGROUND

PIM-1 gene was first identified as a proviral insertion site in Moloney murine leukemia virus-induced T-cell lymphoma. PIM-1 gene translates a Ser/Thr protein kinase. The known PIM kinase family also includes PIM-2 and PIM-3. Mice studies suggest that physiologically the PIM kinases are involved in growth factor and cytokine signaling. Deregulated PIM kinase expression occurs a in large number of hematopoietic tumors, such as myeloid and lymphoblastic leukemias and lyphomas. PIM kinases are also expressed in solid tumors, such as prostate cancer and pancreatic cancer, and transgenic mice which express PIM-1 develop T-cell lymphoma. Dhanasekaran et al., (2001). Nature 412: 822-826 and Li et al., (2006) Cancer Res 66: 6741-6747. Accordingly, it is believed that PIM Kinase inhibitors will be useful in the treatment and/or prevention of cancer. Thus, there is a need to identify inhibitors of PIM kinases.

SUMMARY OF INVENTION

The invention relates to chemical compounds of formula I,

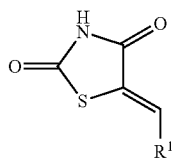

formula I and salts thereof. In some embodiments, the invention relates to inhibitors or modulators of PIM-1 and/or PIM-2, and/or PIM-3 protein kinase activity or enzyme function. In still further embodiments, the invention relates to pharmaceutical compositions comprising compounds disclosed herein, and their use in the prevention and treatment of PIM kinase related conditions and diseases, preferably cancer.

DETAILED DESCRIPTION

The invention relates to a method of treating or preventing cancer comprising, a) providing a pharmaceutical composition comprising a compound of formula I,

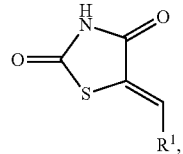

formula I or pharmaceutically acceptable salts thereof, functioning to inhibit a PIM kinase, wherein $R^1$ is selected from a carbocyclyl, aryl, and heterocyclyl, wherein $R^1$ is optionally substituted with one or more, the same or different, $R^2$;

$R^2$ is selected from $C_{1-6}$alkyl, halogen, nitro, cyano, hydroxy, amino, mercapto, formyl, carboxy, carbamoyl, $C_{1-6}$alkoxy, $C_{1-6}$alkylthio, $C_{1-6}$alkylamino, $(C_{1-6}$alkyl$)_2$amino, $C_{1-6}$alkylsulfamoyl, arylsulfamoyl, carbocyclyl, aryl, and heterocyclyl, wherein $R^2$ is optionally substituted with one or more, the same or different, $R^3$;

$R^3$ is selected from $C_{1-6}$alkyl, halogen, nitro, cyano, hydroxy, amino, mercapto, formyl, carboxy, carbamoyl, $C_{1-6}$alkoxy, $C_{1-6}$alkylthio, $C_{1-6}$alkylamino, $(C_{1-6}$alkyl$)_2$amino, $C_{1-6}$alkylsulfinyl, $C_{1-6}$alkylsulfonyl, arylsulfonyl, carbocyclyl, aryl, and heterocyclyl, wherein $R^3$ is optionally substituted with one or more, the same or different, $R^4$;

$R^4$ is selected from $C_{1-6}$alkyl, halogen, nitro, cyano, hydroxy, amino, mercapto, formyl, carboxy, carbamoyl, $C_{1-6}$alkoxy, $C_{1-6}$alkylthio, $C_{1-6}$alkylamino, $(C_{1-6}$alkyl$)_2$-amino, $C_{1-6}$alkylsulfinyl, $C_{1-6}$alkylsulfonyl, arylsulfonyl, carbocyclyl, aryl, and heterocyclyl, wherein $R^4$ is optionally substituted with one or more, the same or different, $R^5$; and $R^5$ is selected from halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl; and b) administering said pharmaceutical composition to a subject diagnosed with, exhibiting symptoms of, or at risk for cancer with the proviso that said compound of formula I is not 5-[[2-[(2,6-dichloro-3-methylphenyl)amino]phenyl]methylene]-2,4-thiazolidinedione.

In some embodiments, the invention relates to a method of treating or preventing cancer comprising, a) providing a pharmaceutical composition comprising a compound of formula I,

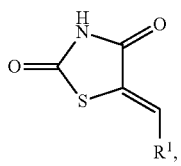

formula I or salts thereof, functioning to inhibit a PIM kinase, wherein $R^1$ is selected from a carbocyclyl, aryl, and heterocyclyl, wherein $R^1$ is optionally substituted with one or more, the same or different, $R^2$;

$R^2$ is selected from halogen, $C_{1-6}$alkyl, halogenated $C_{1-6}$alkyl, amino, $C_{1-6}$alkylamino, $(C_{1-6}$alkyl$)_2$amino, and heterocyclyl, wherein $R^2$ is optionally substituted with one or more, the same or different, $R^3$;

$R^3$ is selected from $C_{1-6}$alkyl, halogen, nitro, cyano, hydroxy, amino, mercapto, formyl, carboxy, carbamoyl, $C_{1-6}$alkoxy, $C_{1-6}$alkylthio, $C_{1-6}$alkylamino, $(C_{1-6}$alkyl$)_2$amino, $C_{1-6}$alkylsulfinyl, $C_{1-6}$alkylsulfonyl, arylsulfonyl, carbocyclyl, aryl, and heterocyclyl, wherein $R^3$ is optionally substituted with one or more, the same or different, $R^4$;

$R^4$ is selected from $C_{1-6}$alkyl, halogen, nitro, cyano, hydroxy, amino, mercapto, formyl, carboxy, carbamoyl, $C_{1-6}$alkoxy, $C_{1-6}$alkylthio, $C_{1-6}$alkylamino, $(C_{1-6}$alkyl$)_2$amino, $C_{1-6}$alkylsulfinyl, $C_{1-6}$alkylsulfonyl, arylsulfonyl, carbocyclyl, aryl, and heterocyclyl, wherein $R^4$ is optionally substituted with one or more, the same or different, $R^5$; and $R^5$ is selected from halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl; and b) administering said pharmaceutical composition to a subject diagnosed with, exhibiting symptoms of, or at risk for cancer under conditions such that cancer is reduced or prevented.

In further embodiments, the invention relates to a method of treating cancer comprising administering to a subject in need thereof a pharmaceutical composition comprising a compound of the formula disclosed herein, wherein said cancer is selected from a leukemia, lymphoma, prostate cancer, pancreatic cancer or other solid tumors.

In further embodiments, the invention relates to a compound of formula IA,

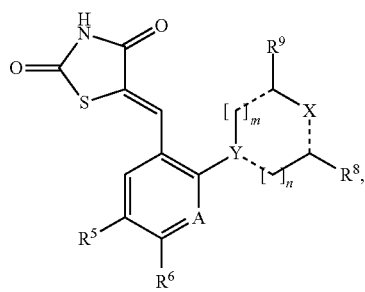

formula IA or salts thereof, wherein,

--- is individually at each occurrence selected from a single and double bond;

n is selected from 0, 1, or 2;
m is selected from 0, 1, or 2;
A is selected from N and $CR^7$;
X is selected from O, S, $CHR^{10}$ and $NR^{11}$;
Y is selected from N, CH, and C;

$R^5$, $R^6$, and $R^7$ are each individually and independently from hydrogen, $C_{1-6}$alkyl, halogen, cyano, nitro, hydroxy, amino, mercapto, formyl, carboxy, carbamoyl, $C_{1-6}$alkoxy, $C_{1-6}$alkylthio, $C_{1-6}$alkylamino, $(C_{1-6}$alkyl$)_2$amino, carbocyclyl, aryl, and heterocyclyl, wherein $R^5$, $R^6$, and $R^7$ are each optionally substituted with one or more, the same or different, $R^{12}$;

$R^8$ and $R^9$ are each individually and independently selected from hydrogen, amino, hydroxyl, mercapto, $C_{1-6}$alkyl, $C_{1-6}$alkylamino, carbocyclyl, aryl, and heterocyclyl wherein $R^8$ and $R^9$ are each optionally substituted with one or more, the same or different, $R^{15}$;

$R^{10}$ is selected from hydrogen, $C_{1-6}$alkyl, halogen, nitro, cyano, hydroxy, amino, mercapto, formyl, carboxy, carbamoyl, $C_{1-6}$alkoxy, $C_{1-6}$alkylthio, $C_{1-6}$alkylamino, $(C_{1-6}$alkyl$)_2$amino, $C_{1-6}$alkylsulfamoyl, arylsulfamoyl, carbocyclyl, aryl, and heterocyclyl, wherein $R^{10}$ is optionally substituted with one or more, the same or different, $R^{12}$;

$R^{11}$ is selected from hydrogen, formyl, $C_{1-6}$alkyl, $C_{1-6}$alkanoyl, $C_{1-6}$alkylsulfinyl, $C_{1-6}$alkylsulfonyl, arylsulfonyl, $C_{1-6}$alkoxycarbonyl, carbocyclyl, aryl, and heterocyclyl, wherein $R^{11}$ is optionally substituted with one or more, the same or different, $R^{12}$;

$R^{12}$ is selected from halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl, wherein $R^{12}$ is optionally substituted with one or more, the same or different, $R^{16}$;

$R^{15}$ is selected from $C_{1-6}$alkyl, $C_{1-6}$alkanoyl, $C_{1-6}$alkylsulfinyl, $C_{1-6}$alkylsulfonyl, arylsulfonyl, and $C_{1-6}$alkoxycarbonyl wherein $R^{15}$ is optionally substituted with one or more, the same or different, $R^{12}$;

$R^{16}$ is selected from halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, aminomethyl, aminoethyl, aminopropyl, aminobutyl, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, and N-methyl-N-ethylsulfamoyl; and provided that $R^5$, $R^6$, and $R^7$ are not all hydrogen and
provided the compound is not 5-((5-nitro-2-(1-piperidinyl) phenyl)methylene)-2,4-thiazolidinedione or 5-(2-(4-morpholinyl)-5-nitrophenyl)methylene)-2,4-thiazolidinedione.

In some embodiments, the invention relates to a compound of formula ID,

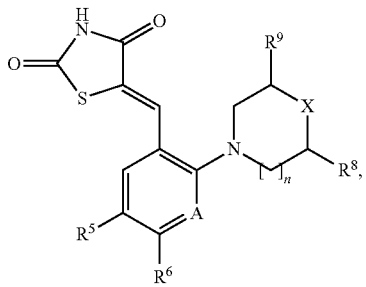

formula ID or salts thereof, wherein,
n is selected from 0, 1, or 2;
A is selected from N and $CR^7$;
X is selected from O, S, $CHR^{10}$ and $NR^{11}$;
$R^5$, $R^6$, and $R^7$ are each individually and independently from hydrogen, $C_{1-6}$alkyl, halogen, cyano, nitro, hydroxy, amino, mercapto, formyl, carboxy, carbamoyl, $C_{1-6}$alkoxy, $C_{1-6}$alkylthio, $C_{1-6}$alkylamino, $(C_{1-6}$alkyl$)_2$amino, carbocyclyl, aryl, and heterocyclyl, wherein $R^5$, $R^6$, and $R^7$ are each optionally substituted with one or more, the same or different, $R^{12}$;
$R^8$ and $R^9$ are each individually and independently selected from hydrogen, amino, hydroxyl, mercapto, $C_{1-6}$alkyl, $C_{1-6}$alkylamino, carbocyclyl, aryl, and heterocyclyl wherein $R^8$ and $R^9$ are each optionally substituted with one or more, the same or different, $R^{15}$;
$R^{10}$ is selected from hydrogen, $C_{1-6}$alkyl, halogen, nitro, cyano, hydroxy, amino, mercapto, formyl, carboxy, carbamoyl, $C_{1-6}$alkoxy, $C_{1-6}$alkylthio, $C_{1-6}$alkylamino, $(C_{1-6}$alkyl$)_2$amino, $C_{1-6}$alkylsulfamoyl, arylsulfamoyl, carbocyclyl, aryl, and heterocyclyl, wherein $R^{10}$ is optionally substituted with one or more, the same or different, $R^{12}$;
$R^{11}$ is selected from hydrogen, formyl, $C_{1-6}$alkyl, $C_{1-6}$alkanoyl, $C_{1-6}$alkylsulfinyl, $C_{1-6}$alkylsulfonyl, arylsulfonyl, $C_{1-6}$alkoxycarbonyl, carbocyclyl, aryl, and heterocyclyl, wherein $R^{11}$ is optionally substituted with one or more, the same or different, $R^{12}$;
$R^{12}$ is selected from halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl, wherein $R^{12}$ is optionally substituted with one or more, the same or different, $R^{16}$;
$R^{15}$ is selected from $C_{1-6}$alkyl, $C_{1-6}$alkanoyl, $C_{1-6}$alkylsulfinyl, $C_{1-6}$alkylsulfonyl, arylsulfonyl, and $C_{1-6}$alkoxycarbonyl wherein $R^{15}$ is optionally substituted with one or more, the same or different, $R^{12}$;
$R^{16}$ is selected from halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, aminomethyl, aminoethyl, aminopropyl, aminobutyl, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, and N-methyl-N-ethylsulfamoyl.

In some embodiments with regard to any of the compound formula provided herein, $R^5$, $R^6$, and $R^7$ are not all hydrogen.

In some embodiments with regard to any of the compound formula provided herein, $R^5$, $R^6$, and $R^7$ are not 5-((5-nitro-2-(1-piperidinyl)phenyl)methylene)-2,4-thiazolidinedione or 5-(2-(4-morpholinyl)-5-nitrophenyl)methylene)-2,4-thiazolidinedione.

In some embodiments, the invention relates to a compound of formula IB, formula IB or salts thereof, wherein,
n is selected from 0, 1, or 2;
X is selected from O, $CHR^{10}$ and $NR^{11}$;
$R^5$, $R^6$, and $R^7$ are each individually and independently from hydrogen, halogen, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, and N-methyl-N-ethylsulfamoyl;
$R^8$ and $R^9$ are each individually and independently selected from hydrogen, amino, $C_{1-6}$alkyl, $C_{1-6}$alkylamino, wherein $R^8$ and $R^9$ are each optionally substituted with one or more, the same or different, $R^{15}$;
$R^{10}$ is selected from hydrogen, $C_{1-6}$alkyl, halogen, nitro, cyano, hydroxy, amino, mercapto, formyl, carboxy, carbamoyl, $C_{1-6}$alkoxy, $C_{1-6}$alkylthio, $C_{1-6}$alkylamino, $(C_{1-6}$alkyl$)_2$ amino, $C_{1-6}$alkylsulfamoyl, arylsulfamoyl, carbocyclyl, aryl, and heterocyclyl, wherein $R^{11}$ is optionally substituted with one or more, the same or different, $R^{12}$;
$R^{11}$ is selected from hydrogen, $C_{1-6}$alkyl, $C_{1-6}$alkanoyl, $C_{1-6}$alkylsulfinyl, $C_{1-6}$alkylsulfonyl, arylsulfonyl, $C_{1-6}$alkoxycarbonyl, carbocyclyl, aryl, and heterocyclyl, wherein $R^{11}$ is optionally substituted with one or more, the same or different, $R^{12}$;
$R^{12}$ is selected from halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl, wherein $R^{12}$ is optionally substituted with one or more, the same or different, $R^{16}$;

$R^{15}$ is selected from $C_{1-6}$alkyl, $C_{1-6}$alkanoyl, $C_{1-6}$alkylsulfinyl, $C_{1-6}$alkylsulfonyl, arylsulfonyl, and $C_{1-6}$alkoxycarbonyl wherein $R^{15}$ is optionally substituted with one or more, the same or different, $R^{12}$;

$R^{16}$ is selected from halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, and N-methyl-N-ethylsulfamoyl.

In some embodiments, with regard to any of the compound formula provided herein, said compound is not, 5-[[2-(4-methyl-1-piperazinyl)phenyl]methylene]-2,4-thiazolidinedione or 5-[[2-[(2,6-dichloro-3-methylphenyl)amino]phenyl]methylene]-2,4-thiazolidinedione.

In further embodiments, the invention relates to a compound of formula IC,

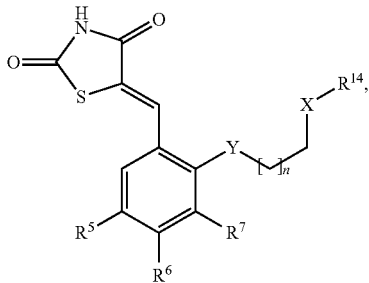

formula IC or salts thereof, wherein,
n is selected from 0, 1, 2, 3, 4, 5, 6, 7 or 8;
X is selected from O, S, $CHR^{10}$ and $NR^{11}$;
Y is selected from O, S, and $NR^{13}$;
$R^5$, $R^6$, and $R^7$ are each individually and independently from $C_{1-6}$alkyl, halogen, nitro, cyano, hydroxy, amino, mercapto, formyl, carboxy, carbamoyl, $C_{1-6}$alkoxy, $C_{1-6}$alkylthio, $C_{1-6}$alkylamino, $C_{1-6}$dialkylamino, carbocyclyl, aryl, and heterocyclyl, wherein $R^5$, $R^6$, and $R^7$ are each optionally substituted with one or more, the same or different, $R^{12}$;
$R^{10}$ is selected from hydrogen, $C_{1-6}$alkyl, halogen, nitro, cyano, hydroxy, amino, mercapto, formyl, carboxy, carbamoyl, $C_{1-6}$alkoxy, $C_{1-6}$alkylthio, $C_{1-6}$alkylamino, $(C_{1-6}$alkyl$)_2$amino, $C_{1-6}$alkylsulfamoyl, arylsulfamoyl, carbocyclyl, aryl, and heterocyclyl, wherein $R^{10}$ is optionally substituted with one or more, the same or different, $R^{12}$;
$R^{11}$, $R^{13}$, and $R^{14}$ are each individually and independently selected from hydrogen, $C_{1-6}$alkyl, $C_{1-6}$alkanoyl, $C_{1-6}$alkylsulfinyl, $C_{1-6}$alkylsulfonyl, aryl sulfonyl, and $C_{1-6}$alkoxycarbonyl wherein $R^{11}$ is optionally substituted with one or more, the same or different, $R^{12}$;

or $R^{11}$ and $R^{14}$, taken together with the atoms to which they are attached form a five, six, or seven membered heterocyclic ring optionally substituted with one or more, the same or different, $R^{12}$;

$R^{12}$ is selected from halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In some embodiments with regard to any of the compound formula provided herein, Y is $NR^{13}$, wherein $R^{13}$ is a $C_{1-6}$alkyl.

In some embodiments with regard to any of the compound formula provided herein, $R^5$ is a halogenated $C_{1-6}$alkyl.

In some embodiments with regard to any of the compound formula provided herein, $R^7$ is a halogen.

In some embodiments, the invention relates to a compound of formula IX,

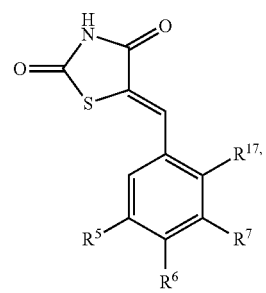

formula IX or salts thereof, wherein
$R^5$ is selected from hydrogen, $C_{1-6}$alkoxy, carbamoyl, and halogenated $C_{1-6}$alkyl;
$R^6$ is selected from hydrogen, halogen, $C_{1-6}$alkoxy, and 2-(1-piperidyl)ethoxy;
$R^7$ is selected from hydrogen, halogen, and $C_{1-6}$alkoxy;
$R^{17}$ is a heterocarbocylcyl, wherein $R^{17}$ is optionally substituted with one or more, the same or different, $R^{18}$;
$R^{18}$ is selected from halogen, formyl, amino, $C_{1-6}$alkyl, $C_{1-6}$alkylamino, $(C_{1-6}$alkyl$)_2$amino, carbocyclyl, aryl, heterocyclyl, wherein $R^{18}$ is optionally substituted with one or more, the same or different, $R^{19}$;
$R^{19}$ is selected from amino, $C_{1-6}$alkyl, hydroxy, carbocyclyl, and heterocyclyl wherein $R^{19}$ is optionally substituted with one or more, the same or different, $R^{20}$; and
$R^{20}$ is selected from amino, $C_{1-6}$alkyl, and halogen.

In further embodiments, $R^{17}$ is selected from (3R)-3-aminopyrrolidin-1-yl, (3R)-3-dimethylaminopyrrolidin-1-yl, (3S)-3-(3-aminopropylamino)pyrrolidin-1-yl, (3S)-3-(5-aminopentanoylamino)pyrrolidin-1-yl, (3S)-3-amino-1-piperidyl, (3S)-3-aminopyrrolidin-1-yl, (3S)-3-dimethylaminopyrrolidin-1-yl, (3S,5R)-3,5-dimethylpiperazin-1-yl, 1,4-diazepan-1-yl, 2-(1-piperidyl)ethoxy, 2-diethylaminoethoxy, 2-dimethylaminoethyl-methyl-amino, 2-hydroxyethoxy, 2-morpholinoethoxy, 3-(2-aminoethylamino)pyrrolidin-1-yl, 3-(2-hydroxyethylamino)pyrrolidin-1-yl, 3-(2-methylaminoethylamino)pyrrolidin-1-yl, 3-(3-aminopropanoylamino)pyrrolidin-1-yl, 3-(3-aminopropylamino)pyrrolidin-1-yl, 3-(3-methyl-1,2,4-oxadiazol-5-yl)-1-piperidyl, 3-(aminomethyl)-1-piperidyl, 3-(aminomethyl)pyrrolidin-1-yl, 3-acetamidopyrrolidin-1-yl, 3-aminopyrrolidin-1-yl, 3-dimethylaminopropoxy, 3-dimethylaminopropyl-methylamino, 3-dimethylaminopyrrolidin-1-yl, 3-hydroxypyrrolidin-1-yl, 3-pyridyl, 4-(1-methyl-4-piperidyl)piperazin-1-yl, 4-(1-piperidyl)-1-piperidyl, 4-(2-aminoethyl)piperazin-1-yl, 4-(2-hydroxyethyl)-1,4-diazepan-1-yl, 4-(2-hydroxyethyl)-1-piperidyl, 4-(2-hydroxyethyl)piperazin-1-yl, 4-(2-methylaminoethyl)piperazin-1-yl, 4-(2-morpholinoethyl)piperazin-1-yl, 4-(3-aminopropanoyl)-1,4-diazepan-1-yl, 4-(3-aminopropanoyl)piperazin-1-yl, 4-(3-aminopropyl)piperazin-1-yl, 4-(3-hydroxypropyl)piperazin-1-yl, 4-(3-methyl-1,2,4-oxadiazol-5-yl)-1-piperidyl, 4-(4-aminobutanoyl)-1,4-diazepan-1-yl, 4-(4-aminobutanoyl)piperazin-1-yl, 4-(4-chloro-2-fluoro-phenyl)piperazin-1-yl, 4-(4-fluorophenyl)piperazin-1-yl, 4-(4-pyridylmethyl)piperazin-1-yl, 4-(5-aminopentanoyl)-1,4-diazepan-1-yl, 4-(5-aminopentanoyl)piperazin-1-yl, 4-(azetidine-3-carbonyl)piperazin-1-yl, 4-(benzo[1,3]dioxol-5-ylmethyl)piperazin-1-yl, 4-(cyclopropylmethyl)piperazin-1-yl, 4-(hydroxymethyl)-1-piperidyl, 4-(piperidine-3-carbonyl)-1,4-diazepan-1-yl, 4-(piperidine-3-carbonyl)piperazin-1-yl, 4-(piperidine-4-carbonyl)piperazin-1-yl, 4-[(2-chlorophenyl)methyl]piperazin-1-yl, 4-[3-(aminomethyl)benzoyl]piperazin-1-yl, 4-[4-(piperazin-1-ylmethyl)benzoyl]piperazin-1-yl, 4-acetylpiperazin-1-yl, 4-amino-1-piperidyl, 4-butyl-1,4-diazepan-1-yl, 4-cyclopentylpiperazin-1-yl, 4-dimethylamino-1-piperidyl, 4-hydroxy-1-piperidyl, 4-isobutylpiperazin-1-yl, 4-isopropylpiperazin-1-yl, 4-methylpiperazin-1-yl, 4-morpholino-1-piperidyl, 4-pyridyl, 4-pyrrolidin-1-yl-1-piperidyl, 4-tert-butoxycarbonylpiperazin-1-yl, 4-tert-butylpiperazin-1-yl, morpholino, piperazin-1-yl, and pyrrolidin-1-yl.

In further embodiments, the invention relates to a compound selected from:

5-({2-[(3S)-3-aminopiperidin-1-yl]-3-chloro-5-(trifluoromethyl)phenyl}methylidene)-1,3-thiazolidine-2,4-dione;
5-({2-[(3R)-3-aminopiperidin-1-yl]-3-chloro-5-(trifluoromethyl)phenyl}methylidene)-1,3-thiazolidine-2,4-dione;
5-{[2-(4-aminopiperidin-1-yl)-3-chloro-5-(trifluoromethyl)phenyl]methylidene}-1,3-thiazolidine-2,4-dione;
5-({2-[3-(aminomethyl)piperidin-1-yl]-3-chloro-5-(trifluoromethyl)phenyl}methylidene)-1,3-thiazolidine-2,4-dione;
5-{[3-chloro-2-(1,4-diazepan-1-yl)-5-(trifluoromethyl)phenyl]methylidene}-1,3-thiazolidine-2,4-dione;
5-{[3-chloro-2-(4-cyclopentylpiperazin-1-yl)-5-(trifluoromethyl)phenyl]methylidene}-1,3-thiazolidine-2,4-dione;
5-({3-chloro-2-[4-(4-fluorophenyl)piperazin-1-yl]-5-(trifluoromethyl)phenyl}methylidene)-1,3-thiazolidine-2,4-dione;
5-({2-[4-(1,3-benzodioxol-5-ylmethyl)piperazin-1-yl]-3-chloro-5-(trifluoromethyl)phenyl}methylidene)-1,3-thiazolidine-2,4-dione;
5-({3-chloro-2-[4-(3-methyl-1,2,4-oxadiazol-5-yl)piperidin-1-yl]-5-(trifluoromethyl)phenyl}methylidene)-1,3-thiazolidine-2,4-dione;
5-{[3-chloro-2-(4-pyrrolidin-1-ylpiperidin-1-yl)-5-(trifluoromethyl)phenyl]methylidene}-1,3-thiazolidine-2,4-dione;
5-({3-chloro-2-[4-(1-methylethyl)piperazin-1-yl]-5-(trifluoromethyl)phenyl}methylidene)-1,3-thiazolidine-2,4-dione;
5-({3-chloro-2-[4-(2-methylpropyl)piperazin-1-yl]-5-(trifluoromethyl)phenyl}methylidene)-1,3-thiazolidine-2,4-dione;
5-({3-chloro-2-[4-(2-hydroxyethyl)piperidin-1-yl]-5-(trifluoromethyl)phenyl}methylidene)-1,3-thiazolidine-2,4-dione;
5-({3-chloro-2-[(3S)-3-(dimethylamino)pyrrolidin-1-yl]-5-(trifluoromethyl)phenyl}methylidene)-1,3-thiazolidine-2,4-dione;
5-({3-chloro-2-[4-(4-chloro-2-fluorophenyl)piperazin-1-yl]-5-(trifluoromethyl)phenyl}methylidene)-1,3-thiazolidine-2,4-dione;
5-({3-chloro-2-[3-(3-methyl-1,2,4-oxadiazol-5-yl)piperidin-1-yl]-5-(trifluoromethyl)phenyl}methylidene)-1,3-thiazolidine-2,4-dione;
5-({3-chloro-2-[4-(pyridin-4-ylmethyl)piperazin-1-yl]-5-(trifluoromethyl)phenyl}methylidene)-1,3-thiazolidine-2,4-dione;
5-({3-chloro-2-[4-(2-chlorobenzyl)piperazin-1-yl]-5-(trifluoromethyl)phenyl}methylidene)-1,3-thiazolidine-2,4-dione;
5-({3-chloro-2-[4-(1-methylpiperidin-4-yl)piperazin-1-yl]-5-(trifluoromethyl)phenyl}methylidene)-1,3-thiazolidine-2,4-dione;
5-({3-chloro-2-[4-(2-morpholin-4-ylethyl)piperazin-1-yl]-5-(trifluoromethyl)phenyl}methylidene)-1,3-thiazolidine-2,4-dione;
5-({3-chloro-2-[4-(cyclopropylmethyl)piperazin-1-yl]-5-(trifluoromethyl)phenyl}methylidene)-1,3-thiazolidine-2,4-dione;
5-{[3-chloro-2-(4-morpholin-4-ylpiperidin-1-yl)-5-(trifluoromethyl)phenyl]methylidene}-1,3-thiazolidine-2,4-dione;
5-({3-chloro-2-[4-(3-hydroxypropyl)piperazin-1-yl]-5-(trifluoromethyl)phenyl}methylidene)-1,3-thiazolidine-2,4-dione;
5-({3-chloro-2-[4-(dimethylamino)piperidin-1-yl]-5-(trifluoromethyl)phenyl}methylidene)-1,3-thiazolidine-2,4-dione;
5-{[3-chloro-2-{[3-(dimethylamino)propyl](methyl)amino}-5-(trifluoromethyl)phenyl]methylidene}-1,3-thiazolidine-2,4-dione;
5-({3-chloro-2-[4-(2-hydroxyethyl)-1,4-diazepan-1-yl]-5-(trifluoromethyl)phenyl}methylidene)-1,3-thiazolidine-2,4-dione;
5-{[2-(4-butyl-1,4-diazepan-1-yl)-3-chloro-5-(trifluoromethyl)phenyl]methylidene}-1,3-thiazolidine-2,4-dione;
5-({3-chloro-2-[4-(2-hydroxyethyl)piperazin-1-yl]-5-(trifluoromethyl)phenyl}methylidene)-1,3-thiazolidine-2,4-dione;
5-{[3-chloro-2-morpholin-4-yl-5-(trifluoromethyl)phenyl]methylidene}-1,3-thiazolidine-2,4-dione;
5-{[2-(4-tert-butylpiperazin-1-yl)-3-chloro-5-(trifluoromethyl)phenyl]methylidene}-1,3-thiazolidine-2,4-dione;
5-{[2-(1,4'-bipiperidin-1'-yl)-3-chloro-5-(trifluoromethyl)phenyl]methylidene}-1,3-thiazolidine-2,4-dione;
5-{[3-chloro-2-(4-methylpiperazin-1-yl)-5-(trifluoromethyl)phenyl]methylidene}-1,3-thiazolidine-2,4-dione;
5-({3-bromo-2-[(3S)-3-(dimethylamino)pyrrolidin-1-yl]phenyl}methylidene)-1,3-thiazolidine-2,4-dione; and
5-({2-[(3R,5S)-3,5-dimethylpiperazin-1-yl]-5-(trifluoromethyl)phenyl}methylidene)-1,3-thiazolidine-2,4-dione;

(5Z)-5-({2-[(3S)-3-aminopyrrolidin-1-yl]-3-chloro-5-(trifluoromethyl)phenyl}methylidene)-1,3-thiazolidine-2,4-dione,
(5Z)-5-({3-[3-(4-methylpiperazin-1-yl)propoxy]phenyl}methylidene)-1,3-thiazolidine-2,4-dione;
2-{3-[(Z)-(2,4-dioxo-1,3-thiazolidin-5-ylidene)methyl]phenoxy}acetamide;
(5Z)-5-{[3-(3-piperidin-1-ylpropoxy)phenyl]methylidene}-1,3-thiazolidine-2,4-dione;
(5Z)-5-({3-[(4-methylpiperazin-1-yl)methyl]phenyl}methylidene)-1,3-thiazolidine-2,4-dione;
N-[2-(dimethylamino)ethyl]-2'-[(Z)-(2,4-dioxo-1,3-thiazolidin-5-ylidene)methyl]-N-methylbiphenyl-4-sulfonamide;
5-({2-[(3S)-3-(dimethylamino)pyrrolidin-1-yl]-5-methoxyphenyl}methylidene)-1,3-thiazolidine-2,4-dione;
5-({2-[(3S)-3-(dimethylamino)pyrrolidin-1-yl]-5-(trifluoromethyl)phenyl}methylidene)-1,3-thiazolidine-2,4-dione;
5-({5-chloro-2-[(3S)-3-(dimethylamino)pyrrolidin-1-yl]phenyl}methylidene)-1,3-thiazolidine-2,4-dione;
5-({2-[(3S)-3-(dimethylamino)pyrrolidin-1-yl]-4-methylphenyl}methylidene)-1,3-thiazolidine-2,4-dione;
5-({2-[(3S)-3-(dimethylamino)pyrrolidin-1-yl]-5-fluorophenyl}methylidene)-1,3-thiazolidine-2,4-dione;
5-({2-[(3S)-3-(dimethylamino)pyrrolidin-1-yl]-5-methylphenyl}methylidene)-1,3-thiazolidine-2,4-dione;
5-({5-bromo-2-[(3S)-3-(dimethylamino)pyrrolidin-1-yl]phenyl}methylidene)-1,3-thiazolidine-2,4-dione;
5-({2-[(3S)-3-(dimethylamino)pyrrolidin-1-yl]-3-fluorophenyl}methylidene)-1,3-thiazolidine-2,4-dione;
5-({2-chloro-6-[(3S)-3-(dimethylamino)pyrrolidin-1-yl]phenyl}methylidene)-1,3-thiazolidine-2,4-dione;
(5Z)-5-({2-[(3R)-3-(aminomethyl)pyrrolidin-1-yl]-3-chlorophenyl}methylidene)-1,3-thiazolidine-2,4-dione;
(5Z)-5-({2-[(3S)-3-(aminomethyl)pyrrolidin-1-yl]-3-chlorophenyl}methylidene)-1,3-thiazolidine-2,4-dione;
(5Z)-5-({2-[(3R)-3-aminopiperidin-1-yl]-3-chlorophenyl}methylidene)-1,3-thiazolidine-2,4-dione;
(5Z)-5-({2-[(3R)-3-aminopiperidin-1-yl]-3-methoxyphenyl}methylidene)-1,3-thiazolidine-2,4-dione;
(5Z)-5-({2-[(3R)-3-aminopiperidin-1-yl]-3-bromophenyl}methylidene)-1,3-thiazolidine-2,4-dione;
(5Z)-5-({2-[(3R)-3-aminopyrrolidin-1-yl]-3-chlorophenyl}methylidene)-1,3-thiazolidine-2,4-dione;
(5Z)-5-({2-[(3S)-3-aminopyrrolidin-1-yl]-3-bromophenyl}methylidene)-1,3-thiazolidine-2,4-dione;
(5Z)-5-({2-[(3R)-3-aminopiperidin-1-yl]-3-ethoxyphenyl}methylidene)-1,3-thiazolidine-2,4-dione;
(5Z)-5-({2-[(3R)-3-aminopiperidin-1-yl]-3-(2-methylpropoxy)phenyl}methylidene)-1,3-thiazolidine-2,4-dione;
(5Z)-5-({2-[(3R)-3-aminopiperidin-1-yl]-3-(cyclohexylmethoxy)phenyl}methylidene)-1,3-thiazolidine-2,4-dione;
(5Z)-5-({2-[(3R)-3-aminopiperidin-1-yl]-3-(cyclohexyloxy)phenyl}methylidene)-1,3-thiazolidine-2,4-dione;
(5Z)-5-({2-[(3R,4R)-3-amino-4-hydroxypiperidin-1-yl]-3-chlorophenyl}methylidene)-1,3-thiazolidine-2,4-dione;
(5Z)-5-{[3-chloro-2-(1,4-diazepan-1-yl)phenyl]methylidene}-1,3-thiazolidine-2,4-dione;
(5Z)-5-({2-[(3R)-3-aminopiperidin-1-yl]-3-(1-methylethoxy)phenyl}methylidene)-1,3-thiazolidine-2,4-dione;
(5Z)-5-({2-[(3S)-3-aminopyrrolidin-1-yl]-3-(1-methylethoxy)phenyl}methylidene)-1,3-thiazolidine-2,4-dione;
(5Z)-5-({2-[(3S)-3-aminopyrrolidin-1-yl]-3-ethoxyphenyl}methylidene)-1,3-thiazolidine-2,4-dione;
(5Z)-5-({2-[(3R)-3-{[4-(aminomethyl)benzyl]amino}piperidin-1-yl]-3-chlorophenyl}methylidene)-1,3-thiazolidine-2,4-dione;
(5Z)-5-({3-chloro-2-[(3R)-3-{[2-(methylamino)ethyl]amino}piperidin-1-yl]phenyl}methylidene)-1,3-thiazolidine-2,4-dione;
(5Z)-5-({2-[(3S,4S)-3-amino-4-hydroxypyrrolidin-1-yl]-3-chlorophenyl}methylidene)-1,3-thiazolidine-2,4-dione;
(5Z)-5-({3-chloro-2-[4-methyl-3-(methylamino)piperidin-1-yl]phenyl}methylidene)-1,3-thiazolidine-2,4-dione;
(5Z)-5-{[2-(3-amino-4-methylpiperidin-1-yl)-3-chlorophenyl]methylidene}-1,3-thiazolidine-2,4-dione;
(5Z)-5-({2-[(3R)-3-aminopiperidin-1-yl]phenyl}methylidene)-1,3-thiazolidine-2,4-dione;
(5Z)-5-({2-[(3S)-3-aminopyrrolidin-1-yl]phenyl}methylidene)-1,3-thiazolidine-2,4-dione;
(5Z)-5-({2-[(3R)-3-aminopiperidin-1-yl]-3-(2,2,2-trifluoroethoxy)phenyl}methylidene)-1,3-thiazolidine-2,4-dione;
(5Z)-5-({2-[(3S)-3-aminopyrrolidin-1-yl]-3-(2,2,2-trifluoroethoxy)phenyl}methylidene)-1,3-thiazolidine-2,4-dione;
(5Z)-5-({2-[(3R)-3-aminopiperidin-1-yl]-3-(2-methoxyethoxy)phenyl}methylidene)-1,3-thiazolidine-2,4-dione;
(5Z)-5-({2-[(3S)-3-aminopyrrolidin-1-yl]-3-(2-methoxyethoxy)phenyl}methylidene)-1,3-thiazolidine-2,4-dione;
(5Z)-5-({2-[(3R)-3-aminopiperidin-1-yl]-3-(cyclopentyloxy)phenyl}methylidene)-1,3-thiazolidine-2,4-dione;
(5Z)-5-({2-[(3R)-3-aminopiperidin-1-yl]-3-(cyclobutyloxy)phenyl}methylidene)-1,3-thiazolidine-2,4-dione;
4-[(3R)-3-aminopiperidin-1-yl]-3-[(Z)-(2,4-dioxo-1,3-thiazolidin-5-ylidene)methyl]benzamide;
4-[(3S)-3-aminopiperidin-1-yl]-3-[(Z)-(2,4-dioxo-1,3-thiazolidin-5-ylidene)methyl]benzamide;
4-[(3R)-3-aminopiperidin-1-yl]-3-[(Z)-(2,4-dioxo-1,3-thiazolidin-5-ylidene)methyl]benzoic acid;
4-[(3S)-3-aminopyrrolidin-1-yl]-3-[(Z)-(2,4-dioxo-1,3-thiazolidin-5-ylidene)methyl]benzoic acid;
(5Z)-5-({2-[(3R)-3-aminopiperidin-1-yl]biphenyl-3-yl}methylidene)-1,3-thiazolidine-2,4-dione;
5-{[2-(3-aminopropoxy)-5-methoxyphenyl]methylidene}-1,3-thiazolidine-2,4-dione;
N-{4-[3-(dimethylamino)pyrrolidin-1-yl]-3-[(Z)-(2,4-dioxo-1,3-thiazolidin-5-ylidene)methyl]phenyl}acetamide;
(5Z)-5-[(3-chloro-2-{(3R)-3-[(2-hydroxyethyl)amino]piperidin-1-yl}phenyl)methylidene]-1,3-thiazolidine-2,4-dione;
(5Z)-5-[(3-chloro-2-{(3R)-3-[(3-hydroxypropyl)amino]piperidin-1-yl}phenyl)methylidene]-1,3-thiazolidine-2,4-dione;
N-[(3S)-1-{2-chloro-6-[(Z)-(2,4-dioxo-1,3-thiazolidin-5-ylidene)methyl]phenyl}pyrrolidin-3-yl]-1-methyl-1H-imidazole-2-carboxamide;
N-[(3S)-1-{2-chloro-6-[(Z)-(2,4-dioxo-1,3-thiazolidin-5-ylidene)methyl]phenyl}pyrrolidin-3-yl]-2-methoxyacetamide;
N-[(3S)-1-{2-chloro-6-[(Z)-(2,4-dioxo-1,3-thiazolidin-5-ylidene)methyl]phenyl}pyrrolidin-3-yl]-1-methyl-1H-pyrazole-3-carboxamide;
$N^2$-carbamoyl-N-[(3S)-1-{2-chloro-6-[(Z)-(2,4-dioxo-1,3-thiazolidin-5-ylidene)methyl]phenyl}pyrrolidin-3-yl]glycinamide;
N-[(3S)-1-{2-chloro-6-[(Z)-(2,4-dioxo-1,3-thiazolidin-5-ylidene)methyl]phenyl}pyrrolidin-3-yl]-2-pyridin-3-ylacetamide;
N-[(3S)-1-{2-chloro-6-[(Z)-(2,4-dioxo-1,3-thiazolidin-5-ylidene)methyl]phenyl}pyrrolidin-3-yl]-2-pyridin-4-ylacetamide;

N-[(3S)-1-{2-chloro-6-[(Z)-(2,4-dioxo-1,3-thiazolidin-5-ylidene)methyl]phenyl}pyrrolidin-3-yl]-1-methyl-1H-pyrazole-4-carboxamide;

N-[(3S)-1-{2-chloro-6-[(Z)-(2,4-dioxo-1,3-thiazolidin-5-ylidene)methyl]phenyl}pyrrolidin-3-yl]-2-(1-oxidothiomorpholin-4-yl)acetamide;

N-[(3S)-1-{2-chloro-6-[(Z)-(2,4-dioxo-1,3-thiazolidin-5-ylidene)methyl]phenyl}pyrrolidin-3-yl]-4-sulfamoylbutanamide;

N'-[(3S)-1-{2-chloro-6-[(Z)-(2,4-dioxo-1,3-thiazolidin-5-ylidene)methyl]phenyl}pyrrolidin-3-yl]-N,N-dimethylbutanediamide;

N-[(3S)-1-{2-chloro-6-[(Z)-(2,4-dioxo-1,3-thiazolidin-5-ylidene)methyl]phenyl}pyrrolidin-3-yl]-N~2~,N~2~-dimethylglycinamide;

N-[(3S)-1-{2-chloro-6-[(Z)-(2,4-dioxo-1,3-thiazolidin-5-ylidene)methyl]phenyl}pyrrolidin-3-yl]-2-cyanoacetamide;

$N^2$-acetyl-N-[(3S)-1-{2-chloro-6-[(Z)-(2,4-dioxo-1,3-thiazolidin-5-ylidene)methyl]phenyl}pyrrolidin-3-yl]glycinamide;

(5Z)-5-({3-chloro-2-[(3R)-3-(dipropylamino)piperidin-1-yl]phenyl}methylidene)-1,3-thiazolidine-2,4-dione;

(5Z)-5-[(3-chloro-2-{(3R)-3-[(3,3,3-trifluoropropyl)amino]piperidin-1-yl}phenyl)methylidene]-1,3-thiazolidine-2,4-dione;

5-[(5-methoxy-2-{3-[(1-methylethyl)amino]propoxy}phenyl)methylidene]-1,3-thiazolidine-2,4-dione;

(5Z)-5-({5-amino-2-[3-(dimethylamino)pyrrolidin-1-yl]phenyl}methylidene)-1,3-thiazolidine-2,4-dione; and 5-[(2-amino-4,5-dimethoxyphenyl)methylidene]-1,3-thiazolidine-2,4-dione, or salts thereof.

In some embodiments, the invention relates to any of the compounds disclosed herein that are in the (Z) isomer.

In some embodiments, the invention relates to any of the compounds disclosed herein that are in the (E) isomer.

In some embodiments, the invention relates to compositions comprising a mixture of the (Z) and (E) isomers.

In some embodiments, the invention relates to a pharmaceutical composition comprising a substituted 5-(3-halo-2-[piperidin-1-yl]phenylmethylidene)-1,3-thiazolidine-2,4-dione functioning to inhibit a PIM kinase.

In further embodiments, the invention relates to a pharmaceutical composition comprising a compound of formula I, IA, IB, IC, ID, or IX or a pharmaceutically acceptable salt thereof.

In further embodiments, the invention relates to a method of inhibiting a PIM kinase comprising, providing a compound of formula I, IA, IB, IC, ID, or IX, as defined herein, and mixing a PIM kinase and said compound under conditions such that PIM kinase phosphorylation is inhibited.

In further embodiments, said method is an in vitro method.

In further embodiments, said method is an in vivo method.

In further embodiments, the invention relates to a method of inhibiting a PIM kinase in a subject comprising administering to the subject a therapeutically effective amount of a compound of any of the formula disclosed herein or a pharmaceutically acceptable salt thereof.

In further embodiments, said PIM kinase is selected from PIM-1, PIM-2, and PIM-3.

In further embodiments, the invention relates to the use of a compound of the formula I, IA, IB, IC, ID, or IX, or a pharmaceutically acceptable salt thereof, as defined herein, for the manufacture of a medicament for the production of a PIM kinase inhibitory effect in a subject.

In further embodiments, the invention relates to the use of a compound of the formula I, IA, IB, IC, ID, or IX, or a pharmaceutically acceptable salt thereof, as disclosed herein, for the manufacture of a medicament for the production of an anti-cancer effect in a subject.

In some embodiments, the invention relates to a method of making a compound of formula IA as defined herein,

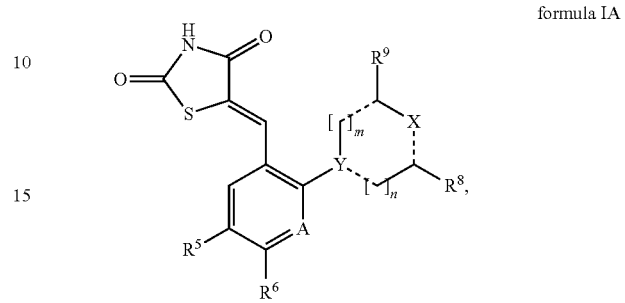

formula IA or salt thereof, comprising
a) mixing a compound of formula XI, formula XI or salt thereof, wherein E is a halogen, and $R^5$, $R^6$, and A are defined herein, with a compound of formula XII, formula XII or salt thereof, wherein
---, $R^8$, $R^9$, n, m, Y and X are defined herein,
if Y is N, then $R^{21}$ is hydrogen,
if Y is C, then $R^{21}$ is selected from boronic acid and a boronic ester, and
if Y is CH, then $R^{21}$ is selected from a metal halide,
under conditions such that composition comprising a compound of formula XIII, formula XIII or salt thereof, is formed; and
b) mixing the compound of formula XIII and thiazolidine-2,4-dione under conditions such that a compound of formula IA is formed.

In further embodiments, said metal halide is selected from lithium chloride and magnesium bromide.

In further embodiments, said boronic ester is a dialkyl boronic ester, such as diethyl boronic ester, or a cyclic boronic ester, such as the boronic ester of 1,2-alkyldiols, such as 1,3,2-dioxaborolane, or cycloalkyldiols which may be optionally substituted.

In further embodiments, the invention relates to a method of making a compound of formula ID, or salt thereof comprising a) mixing a compound of formula II,

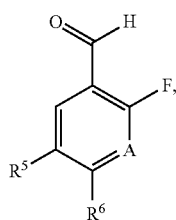

formula II or salt thereof, wherein $R^5$, $R^6$, and A are defined herein, with a compound of formula III,

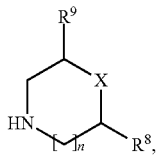

formula III or salt thereof, wherein $R^8$, $R^9$, n, and X are defined herein, under conditions such that composition comprising a compound of formula IV,

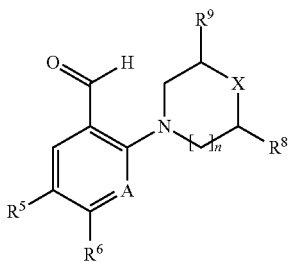

formula IV or salt thereof, is formed; and
b) mixing the compound of formula IV and thiazolidine-2,4-dione under conditions such that a compound of formula ID is formed.

In further embodiments, the invention relates to a method of making a compound of formula IC, or salt thereof comprising a) mixing a compound of formula V,

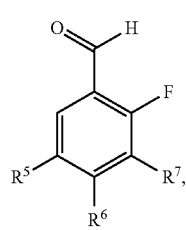

formula V or salt thereof, wherein $R^5$, $R^6$, and $R^7$ are defined herein, with a compound of formula VI,

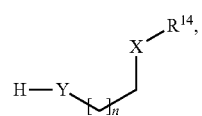

formula VII or salt thereof, wherein $R^{14}$, n, X and Y are defined herein, under conditions such that a composition comprising a compound of formula VIII,

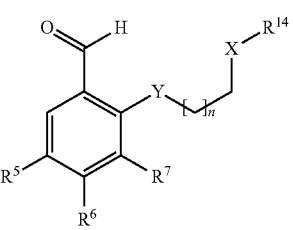

or salt thereof, is formed; and
b) mixing the compound of formula VIII and thiazolidine-2, 4-dione under conditions such that a compound of formula IC is formed.

In some embodiments, the invention relates to compounds of formula I, IA, IB, IC, ID, or IX provided that they are not selected from 5-((2-dipropylamino-5-nitrophenyl)methylene)-2,4-thiazolidinedione;
5-((5-nitro-2-(1-piperidinyl)phenyl)methylene)-2,4-thiazolidinedione;
5-((2-(4-morpholinyl)-5-nitrophenyl)methylene)-2,4-thiazolidinedione;
5-[[2-(4-methyl-1-piperazinyl)phenyl]methylene]-2,4-thiazolidinedione;
5-[[2-[(2,6-dichloro-3-methylphenyl)amino]phenyl]methylene]-2,4-thiazolidinedione;
[2S-[2α(Z),4α]]-1-([1,1'-biphenyl]-4-ylsulfonyl)-N-[2-[(2, 4-dioxo-5-thiazolidinylidene)methyl]phenyl]-4-(methylthio)-2-pyrrolidinemethanamine;
1,1-dimethylethyl ester [[2S-[2α(Z),4α]]-3-[[[1-([1,1'-biphenyl]-4-ylsulfonyl)-4-(methylthio)-2-pyrrolidinyl]methyl]amino]-4-[(2,4-dioxo-5-thiazolidinylidene)methyl] phenyl]carbamic acid; and
[2S-[2α(Z),4α]]-N-[5-amino-2-[(2,4-dioxo-5-thiazolidinylidene)methyl]phenyl]-1-([1,1'-biphenyl]-4-ylsulfonyl)-4-(methylthio)-2-pyrrolidinemethanamine.

It is the Applicants understanding that WO 2001002377 discloses 5-((2-dipropylamino-5-nitrophenyl)methylene)-2, 4-thiazolidinedione, 5-((5-nitro-2-(1-piperidinyl)phenyl) methylene)-2,4-thiazolidinedione, and 5-((2-(4-morpholinyl)-5-nitrophenyl)methylene)-2,4-thiazolidinedione.

It is the Applicants understanding that WO 9814433 discloses 5-[[2-(4-methyl-1-piperazinyl)phenyl]methylene]-2, 4-thiazolidinedione.

It is the Applicants understanding that U.S. Pat. No. 6,211, 209 discloses, 5-[[2-[(2,6-dichloro-3-methylphenyl)amino] phenyl]methylene]-2,4-thiazolidinedione.

It is the Applicants understanding that WO 9705135 discloses, [2S-[2α(Z),4α]]-1-([1,1'-biphenyl]-4-ylsulfonyl)-N-[2-[(2,4-dioxo-5-thiazolidinylidene)methyl]phenyl]-4-(methylthio)-2-pyrrolidinemethanamine, 1,1-dimethylethyl ester [[2S-[2α(Z),4α]]-3-[[[1-([1,1'-biphenyl]-4-ylsulfonyl)-4-(methylthio)-2-pyrrolidinyl]methyl]amino]-4-[(2,4-dioxo- 5-thiazolidinylidene)methyl]phenyl]-carbamic acid, and [2S-[2α(Z),4α]]-N-[5-amino-2-[(2,4-dioxo-5-thiazolidinylidene)methyl]phenyl]-1-([1,1'-biphenyl]-4-ylsulfonyl)-4-(methylthio)-2-pyrrolidinemethanamine.

The preceding understandings are not intended to be admissions.

In some embodiments, compounds disclosed herein could be used in the clinic either as a single agent by itself or in combination with other clinically relevant agents. This compound could also prevent the potential cancer resistance mechanisms that may arise due to mutations in a set of genes.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon (ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as:
N-(3-chloro-4-fluorophenyl)-7-methoxy-6-(3-morpholinopropoxy)quinazolin-4-a mine (gefitinib, AZD1839),
N-(3-ethynylphenyl)-6,7-bis(2-methoxyethoxy)quinazolin-4-amine (erlotinib, OSI-774), and
6-acrylamido-N-(3-chloro-4-fluorophenyl)-7-(3-morpholinopropoxy)quinazolin-4-amine (CI 1033),
for example inhibitors of the platelet-derived growth factor family and for example inhibitors of the hepatocyte growth factor family, for example inhibitors or phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (Abl) tyrosine kinase family such as AZD0530 and dasatinib (BMS-354825) and imatinib mesylate (Gleevec™); and any agents that modify STAT signaling.

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically-active agent within its approved dosage range.

The invention relates to phosphorylation inhibitors of PIM kinases. In still further embodiments, the invention relates to pharmaceutical composition comprising compounds disclosed herein and their use in the prevention and treatment of cancer.

It is understood the compositions disclosed herein may exist in solid and solution form tautomers. For example, imidazole and imidazole containing heterocycles may be drawn in a formula such that one or the other of the nitrogens contain a hydrogen atom. However, as provided herein, embodiments of such a formula are considered to encompass alternative tautomeric forms.

As used herein, "alkyl" means a noncyclic straight chain or branched, unsaturated or saturated hydrocarbon such as those containing from 1 to 10 carbon atoms, while the term "lower alkyl" or "$C_{1-6}$alkyl" has the same meaning as alkyl but contains from 1 to 6 carbon atoms. The term "higher alkyl" has the same meaning as alkyl but contains from 7 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

A "halogenated alkyl" refers to an alkyl group where one or more or all of the hydrogen(s) are substituted with halogen(s). A representative halogenated alkyl includes trifluoromethyl (i.e., —$CF_3$).

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, aryls and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—$CH_3$).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above with the indicated number of carbon atoms attached through an amino bridge. An example of an alkylamino is methylamino, (i.e., —NH—$CH_3$).

"Alkanoyl" refers to an alkyl as defined above with the indicated number of carbon atoms attached through a carbonyl bride (i.e., —(C=O)alkyl).

"Alkylsulfonyl" refers to an alkyl as defined above with the indicated number of carbon atoms attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfamoyl" refers to an alkyl as defined above with the indicated number of carbon atoms attached through a sulfamoyl bridge (i.e., —NHS(=O)$_2$alkyl), and an "Arylsulfamoyl" refers to an alkyl attached through a sulfamoyl bridge (i.e., (i.e., —NHS(=O)$_2$aryl).

"Alkylsulfinyl" refers to an alkyl as defined above with the indicated number of carbon atoms attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —$NR_aR_b$, —$NR_aC(=O)R_b$, —$NR_aC(=O)NR_aNR_b$, —$NR_aC(=O)OR_b$, —$NR_aSO_2R_b$, —C(=O)$R_a$, —C(=O)$OR_a$, —C(=O)$NR_aR_b$, —OC(=O)$NR_aR_b$, —$OR_a$, —$SR_a$, —$SOR_a$, —S(=O)$_2R_a$, —OS(=O)$_2R_a$ and —S(=O)$_2OR_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, the terms "prevent" and "preventing" include the prevention of the recurrence, spread or onset. It is not intended that the present invention be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present invention also contemplate treatment that merely reduces symptoms, and/or delays disease progression.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional non-toxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

"Subject" means any animal, preferably a human patient, livestock, or domestic pet.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, her2 for breast cancer, or others.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use.

Administration may be topical, i.e., substance is applied directly where its action is desired, enteral or oral, i.e., substance is given via the digestive tract, parenteral, i.e., substance is given by other routes than the digestive tract such as by injection.

In a preferred embodiment, the active compound and optionally another therapeutic or prophylactic agent are formulated in accordance with routine procedures as pharmaceutical compositions adapted for intravenous administration to human beings. Typically, the active compound for intravenous administration are solutions in sterile isotonic aqueous buffer. Where necessary, the compositions can also include a solubilizing agent. Compositions for intravenous administration can optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule. Where the active compound is to be administered by infusion, it can be dispensed, for example, with an infusion bottle containing sterile pharmaceutical grade water or saline. Where the active compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. A time delay material such as glycerol monostearate or glycerol stearate can also be used. Oral compositions can include standard vehicles such as mannitol, lactose, starch, magnesium stearate, sodium saccharine, cellulose, magnesium carbonate, and the like. Such vehicles are preferably of pharmaceutical grade.

Compositions for use in accordance with the present invention can be formulated in conventional manner using one or more physiologically acceptable carriers or excipients. Thus, the compound and optionally another therapeutic or prophylactic agent and their physiologically acceptable salts and solvates can be formulated into pharmaceutical compositions for administration by inhalation or insufflation (either through the mouth or the nose) or oral, parenteral or mucosol (such as buccal, vaginal, rectal, sublingual) administration. In one embodiment, local or systemic parenteral administration is used.

For oral administration, the compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

EXPERIMENTAL

The following is intended to provide examples on methods of making and using embodiments of the invention. It is not intended to limit the scope.

Example 1

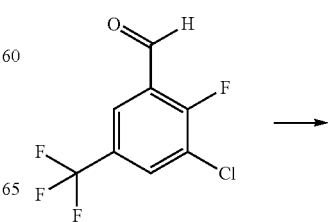

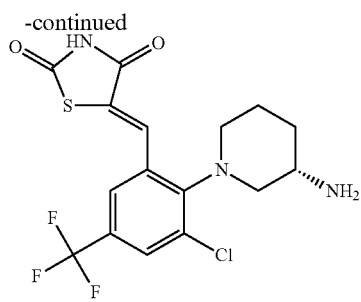

(S,Z)-5-(2-(3-aminopiperidin-1-yl)-3-chloro-5-(trifluoromethyl)benzylidene)thiazolidine-2,4-dione trifluoroacetate A 40 mL vial was charged with a magentic stir bar, 3-chloro-2-fluoro-5-(trifluoromethyl)benzaldehyde (0.134 ml, 1.10 mmol), acetonitrile (2.76 ml), (S)-tert-butyl piperidin-3-ylcarbamate (0.221 g, 1.10 mmol), and K₂CO₃ (0.229 g, 1.66 mmol). The vial was heated to 70° C. with stiffing for 2 h. The vessel was cooled to rt and the mixture was diluted with DCM and filtered. The filtrate was conc. in vacuo to afford the substituted aldehyde which was dissolved in EtOH (2.76 ml). Thiazolidine-2,4-dione (0.155 g, 1.32 mmol) and piperidine (9.40 mg, 0.11 mmol) were then added. The mixture was heated to reflux for 4 h before being allowed to cool to rt and the mixture was conc. in vacuo. The product was dissolved DCM (2 mL) and TFA (1 mL) and stirred at rt for 1 h before being conc. in vacuo. The residue was dissolved in DMSO (~2 mL) and purified via reverse phase HPLC to afford (S,Z)-5-(2-(3-aminopiperidin-1-yl)-3-chloro-5-(trifluoromethyl)benzylidene)thiazolidine-2,4-dione trifluoroacetate (0.214 g, 37.3%). ¹H NMR (300 MHz, DMSO-D6) δ ppm 12.78 (s, 1 H) 7.95 (m, 3 H) 7.79 (s, 1 H) 7.62 (s, 1 H) 3.40-3.20 (s, 5 H) 2.12-2.06 (m, 1 H) 1.79-1.70 (m 1H) 1.65-1.60 (m, 1 H) 1.52-1.41 (m, 1 H); m/z 406.

The following examples were prepared by the procedure of Example 1, using the appropriate starting materials. The following parent compounds obtained after chromatography may be converted to their corresponding hydrochloride salts using the procedure in Example 6, or a similar procedure.

| Ex. | Compound | ¹H NMR (300 MHz) | m/z | SM |
|---|---|---|---|---|
| 2 | (R,Z)-5-(2-(3-aminopiperidin-1-yl)-3-chloro-5-(trifluoromethyl)benzylidene)thiazolidine-2,4-dione trifluoroacetate | 12.79 (s, 1 H) 7.98 (s, 2 H) 7.95 (s, 1 H) 7.79 (s, 1 H) 7.62 (s, 1 H) 3.31-3.20 (m, 5 H) 2.12-2.09 (m, 1 H) 1.85-1.77 (m, 1 H) 1.66-1.63 (m, 1 H) 1.45-1.40 (m, 1 H) | 406 | (R)-tert-butyl piperidin-3-ylcarbamate |
| 3 | (Z)-5-(2-(4-aminopiperidin-1-yl)-3-chloro-5-(trifluoromethyl)benzylidene)thiazolidine-2,4-dione trifluoroacetate | 12.76 (s, 1 H) 7.99 (s, 1 H) 7.91 (s, 2 H) 7.78 (s, 1 H) 7.60 (s, 1 H) 3.33-3.18 (m, 5 H) 1.94 (d, 2 H) 1.71-1.60 (m, 2 H) | 406 | tert-butyl piperidin-4-ylcarbamate |

-continued

| Ex. | Compound | ¹H NMR (300 MHz) | m/z | SM |
|---|---|---|---|---|
| 4 | (Z)-5-(2-(3-(aminomethyl)piperidin-1-yl)-3-chloro-5-(trifluoromethyl)benzylidene)thiazolidine-2,4-dione trifluoroacetate | 12.78 (s, 1 H) 7.93 (s, 1 H) 7.84 (s, 1 H) 7.75 (s, 1 H) 7.61 (s, 1 H) 3.31-3.05 (m, 6 H) 2.79-2.71 (m, 1 H) 1.95-1.89 (m, 2 H) 1.72-1.55 (m, 2 H) 1.29-1.10 (m, 1 H) | 421 | tert-butyl piperidin-3-ylmethylcarbamate |
| 5A | (Z)-5-(3-chloro-2-(1,4-diazepan-1-yl)-5-(trifluoromethyl)benzylidene)thiazolidine-2,4-dione hydrochloride | 12.83 (brs, 1 H) 9.20 (brs, 2 H) 8.05 (d, 1 H) 7.90 (s, 1 H) 7.66 (d, 1 H) 3.51 (brs, 2 H) 3.35 (d, 2 H) 3.26-3.03 (m, 4 H) 2.27-1.99 (m, 2 H) | 405 | tert-butyl 1,4-diazepane-1-carboxylate |
| 5B | (S,Z)-5-(2-(3-aminopyrrolidin-1-yl)-3-chloro-5-(trifluoromethyl)benzylidene)thiazolidine-2,4-dione | 12.73 (brs, 1 H) 8.29 (brs, 3 H) 7.93 (s, 1 H) 7.83 (s, 1 H) 7.66 (s, 1 H) 3.88 (brs, 1 H) 3.66 (dd, 1 H), 3.52-3.27 (m, 3 H) 2.42-2.19 (m, 1 H) 2.12-1.88 (m, 1 H) | 392 | tert-butyl (3S)-pyrrolidin-3-ylcarbamate |

Example 6

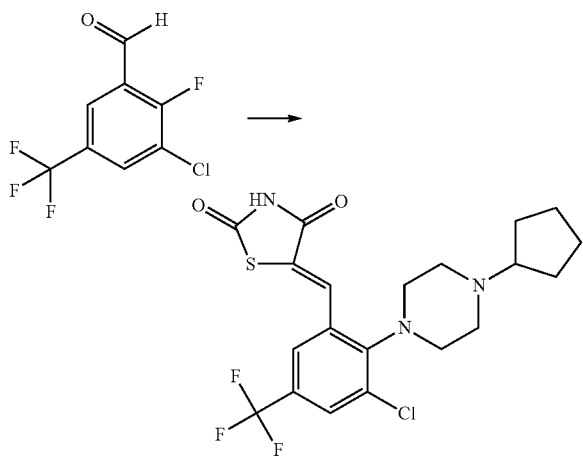

(Z)-5-(3-chloro-2-(4-cyclopentylpiperazin-1-yl)-5 (trifluoromethyl)benzylidene)thiazolidine-2,4-dione hydrochloride A 40 mL vial was charged with a magnetic stir bar, 3-chloro-2-fluoro-5-(trifluoromethyl)benzaldehyde (0.134 ml, 1.10 mmol), acetonitrile (2.76 ml), 1-cyclopentylpiperazine (0.213 g, 1.38 mmol), and $K_2CO_3$ (0.229 g, 1.66 mmol). The vial was heated to 70° C. with stirring for 2 h. The vessel was then cooled to rt and the mixture was diluted with DCM and filtered. The filtrate was conc. in vacuo to afford the substituted aldehyde which was dissolved in EtOH (2.76 ml). Thiazolidine-2,4-dione (0.155 g, 1.32 mmol) and piperidine (9.40 mg, 0.11 mmol) were then added and the mixture was heated to reflux for 4 h before being allowed to cool to rt. The mixture was then conc. in vacuo to afford the product which was dissolved in DMSO (~2 mL) and purified via reverse phase HPLC to afford fractions that were conc. in vacuo, suspended in methanol (~5 mL) and 1N HCl in diethyl ether (~2 mL). This mixture was conc. in vacuo to afford (Z)-5-(3-chloro-2-(4-cyclopentylpiperazin-1-yl)-5-(trifluoromethyl) benzylidene)thiazolidine-2,4-dione hydrochloride (0.215 g, 39.3%). $^1$H NMR (300 MHz, DMSO-D6) δ ppm 12.78 (s, 1 H) 7.96 (s, 1 H) 7.83 (s, 1 H) 7.63 (s, 1 H) 3.77-3.50 (m, 5 H) 3.30-3.22 (m, 2 H) 3.08-2.99 (m, 2 H) 2.03-1.99 (m, 2 H) 1.84-1.61 (m, 4 H) 1.60-1.50 (m, 2 H); m/z 461.

The following examples were prepared by the procedure of Example 6, using the appropriate starting materials. The following parent compounds obtained after chromatography may be converted to their corresponding hydrochloride salt in a manner similar as described in example 6.

| Ex. | Compound | $^1$H NMR | m/z | SM |
|---|---|---|---|---|
| 7 | (Z)-5-(3-chloro-2-(4-(4-fluorophenyl)piperazin-1-yl)-5-(trifluoromethyl)benzylidene)thiazolidine-2,4-dione | 12.74 (s, 1 H) 7.89-8.01 (m, 2 H) 7.62 (s, 1 H) 6.99-7.13 (m, 4 H) 3.34-3.23 (m, 8 H) | 486 | 1-(4-fluorophenyl)piperazine |
| 8 | (Z)-5-(2-(4-(benzo[d][1,3]dioxol-5-ylmethyl)piperazin-1-yl)-3-chloro-5-(trifluoromethyl)benzylidene)thiazolidine-2,4-dione trifluoroacetate | 12.77 (s, 1 H) 7.97 (d, 1 H) 7.97 (s, 1 H) 7.77 (s, 1 H) 7.63 (s, 1 H) 7.10 (s, 1 H) 7.02 (s, 2 H) 6.08 (s, 2 H) 4.34 (s, 2 H) 3.58-3.11 (m, 8 H) | 526 | 1-(benzo[d][1,3]dioxol-5-ylmethyl)piperazine |

-continued

| Ex. | Compound | ¹H NMR | m/z | SM |
|---|---|---|---|---|
| 9 | (Z)-5-(3-chloro-2-(4-(3-methyl-1,2,4-oxadiazol-5-yl)piperidin-1-yl)-5-(trifluoromethyl)benzylidene)thiazolidine-2,4-dione | 12.72 (s, 1 H) 7.91 (s, 1 H) 7.84 (s, 1 H) 7.61 (s, 1 H) 3.33-3.18 (m, 4 H) 2.79-2.71 (m, 1 H) 2.33 (s, 3 H) 2.06 (d, 2 H) 1.98-1.80 (m, 2 H) | 473 | 3-methyl-5-(piperidin-4-yl)-1,2,4-oxadiazole |
| 10 | (Z)-5-(3-chloro-2-(4-pyrrolidin-1-yl)piperidin-1-yl)-5-(trifluoromethyl)benzylidene)thiazolidine-2,4-dione hydrochloride | 12.78 (s, 1 H) 7.92 (s, 1 H) 7.79 (s, 1 H) 7.60 (s, 1 H) 3.33-3.20 (m, 5 H) 3.12-3.03 (m, 4 H) 2.09 (d, 2 H) 1.97-1.78 (m, 6 H) | 461 | 4-(pyrrolidin-1-yl)piperidine |
| 11 | (Z)-5-(3-chloro-2-(4-isopropylpiperazin-1-yl)-5-(trifluoromethyl)benzylidene)thiazolidine-2,4-dione hydrochloride | 12.80 (s, 1 H) 7.96 (s, 1 H) 7.82 (s, 1 H) 7.62 (s, 1 H) 3.85 (t, 2 H) 3.55-3.52 (m, 1 H) 3.41 (d, 2 H) 3.26 (d, 2 H) 3.10-3.06 (m, 2 H) 1.32 (d, 6 H) | 434 | 1-isopropylpiperazine |

| Ex. | Compound | ¹H NMR | m/z | SM |
|---|---|---|---|---|
| 12 | (Z)-5-(3-chloro-2-(4-isobutylpiperazin-1-yl)-5-(trifluoromethyl)benzylidene)thiazolidine-2,4-dione hydrochloride | 12.80 (s, 1 H) 7.96 (d, 1 H) 7.80 (s, 1 H) 7.63 (s, 1 H) 3.87 (brs, 2 H) 3.52 (d, 2 H) 3.27 (brs, 2 H) 3.11-3.00 (m, 4 H) 2.10 (qq, 1 H) 1.00 (d, 6 H) | 450 | 1-isobutylpiperazine |
| 13 | (Z)-5-(3-chloro-2-(4-(2-hydroxyethyl)piperidin-1-yl)-5-(trifluoromethyl)benzylidene)thiazolidine-2,4-dione | 12.73 (s, 1 H) 7.87 (s, 1 H) 7.83 (s, 1 H) 7.59 (s, 1 H) 3.46 (t, 2 H) 3.23 (t, 2 H) 3.07 (brs, 2 H) 1.70 (d, 2 H) 1.61-1.52 (m, 1 H) 1.42 (q, 2 H) 1.33-1.20 (m, 2 H) | 437 | 2-(piperidin-4-yl)ethanol |
| 14 | (S,Z)-5-(3-chloro-2-(3-(dimethylamino)pyrrolidin-1-yl)-5-(trifluoromethyl)benzylidene)thiazolidine-2,4-dione hydrochloride | 12.65 (s, 1 H) 7.82 (s, 1 H) 7.72 (s, 1 H) 7.53 (s, 1 H) 3.59-3.50 (m, 1 H) 3.38-3.30 (m, 4 H) 2.56 (s, 6 H) 2.31-2.28 (m, 1 H) 2.09-2.01 (m, 1 H) | 421 | (S)-N,N-dimethylpyrrolidin-3-amine |

-continued

| Ex. | Compound | ¹H NMR | m/z | SM |
|---|---|---|---|---|
| 15 | (Z)-5-(3-chloro-2-(4-(4-chloro-2-fluorophenyl)piperazin-1-yl)-5-(trifluoromethyl)benzylidene)thiazolidine-2,4-dione hydrochloride | 12.75 (brs, 1 H) 8.06-7.90 (m, 2 H) 7.64 (d, 1 H) 7.38 (dd, 1 H) 7.23 (dd, 1 H) 7.11 (t, 1 H) 3.42 (m, 4 H) 3.15 (d, 4 H) | 520 | 1-(4-chloro-2-fluorophenyl)piperazine |
| 16 | (Z)-5-(3-chloro-2-(3-(3-methyl-1,2,4-oxadiazol-5-yl)piperidin-1-yl)-5-(trifluoromethyl)benzylidene)thiazolidine-2,4-dione hydrochloride |  | 471 | 3-methyl-5-(piperidin-3-yl)-1,2,4-oxadiazole |

| Ex. | Compound | ¹H NMR | m/z | SM |
|---|---|---|---|---|
| 17 | (Z)-5-(3-chloro-2-(4-(pyridin-4-ylmethyl)piperazin-1-yl)-5-(trifluoromethyl)benzylidene)thiazolidine-2,4-dione hydrochloride | 12.75 (brs, 1H) 8.78 (d, 2 H) 7.98 (s, 1 H) 7.74 (brs, 1 H) 7.71 (s, 1 H) 7.64 (s, 1 H) 4.44 (brs, 2 H) 3.44 (brs, 4 H) 3.17 (s, 4 H) | 483 | 1-(pyridin-4-ylmethyl)piperazine |
| 18 | (Z)-5-(3-chloro-2-(4-(2-chlorobenzyl)piperazin-1-yl)-5-(trifluoromethyl)benzylidene)thiazolidine-2,4-dione hydrochloride | 7.98 (d, 1 H) 7.73 (dd, 1 H) 7.68-7.59 (m, 2 H) 7.58-7.42 (m, 3 H) 4.53 (brs, 2 H) 3.75-3.30 (m, 8 H) | 517 | 1-(2-chlorobenzyl)piperazine |

| Ex. | Compound | ¹H NMR | m/z | SM |
|---|---|---|---|---|
| 19 | (Z)-5-(3-chloro-2-(4-(1-methylpiperidin-4-yl)piperazin-1-yl)-5-(trifluoromethyl)benzylidene)thiazolidine-2,4-dione hydrochloride | 10.68 (brs, 1 H) 7.92 (d, 1 H) 7.78 (brs, 1 H) 7.58 (s, 1 H) 3.73-3.63 (m, 1 H) 3.61-3.41 (m, 6 H) 3.10 (brs, 3 H) 2.93 (brs, 3 H) 2.67 (s, 3 H) 2.39-2.18 (m, 2 H) 2.07 (brs, 2 H) | 489 | 1-(1-methylpiperidin-4-yl)piperazine |
| 20 | (Z)-5-(3-chloro-2-(4-(2-morpholinoethyl)piperazin-1-yl)-5-(trifluoromethyl)benzylidene)thiazolidine-2,4-dione hydrochloride | 11.12 (brs, 1 H) 7.91 (d, 1 H) 7.79 (brs, 1 H) 7.59 (s, 1 H) 3.80-2.81 (m, 20 H) | 505 | 4-(2-(piperazin-1-yl)ethyl)morpholine |

| Ex. | Compound | ¹H NMR | m/z | SM |
|---|---|---|---|---|
| 21 | (Z)-5-(3-chloro-2-(4-(cyclopropylmethyl)piperazin-1-yl)-5-(trifluoromethyl)benzylidene)thiazolidine-2,4-dione hydrochloride | 12.59 (brs, 1 H) 7.76 (d, 1 H) 7.61 (brs, 1 H) 7.43 (s, 1 H) 3.62 (brs, 2 H) 3.44-3.24 (m, 2 H) 3.10 (brs, 2 H) 2.87 (d, 4 H) 0.94 (brs, 1 H) 0.54-0.31 (m, 2 H) 0.32-0.08 (m, 2 H) | 447 | 1-(cyclopropylmethyl)piperazine |
| 22 | (Z)-5-(3-chloro-2-(4-morpholinopiperidin-1-yl)-5-(trifluoromethyl)benzylidene)thiazolidine-2,4-dione hydrochloride | 12.92 (brs, 1 H) 8.08 (d, 1 H) 7.95 (brs, 1 H) 7.76 (s, 1 H) 4.14 (brs, 3 H) 3.98 (brs, 2 H) 3.58 (brs, 3 H) 3.53-3.34 (m, 3 H) 3.28 (brs, 2 H) 2.32 (brs, 2 H) 1.92 (d, 2 H) | 476 | 4-(piperidin-4-yl)morpholine |

-continued

| Ex. | Compound | ¹H NMR | m/z | SM |
|---|---|---|---|---|
| 23 | (Z)-5-(3-chloro-2-(4-(3-hydroxypropyl)piperazin-1-yl)-5-(trifluoromethyl)benzylidene)thiazolidine-2,4-dione hydrochloride | 12.90 (brs, 1 H) 10.52 (brs, 1 H) 7.98 (d, 1 H) 7.84 (brs, 1 H) 7.65 (s, 1 H) 3.90-3.65 (m, 2 H) 3.57-3.41 (m, 5 H) 3.30-3.06 (m, 5 H) 1.96-1.73 (m, 2 H) | 450 | 3-(piperazin-1-yl)propan-1-ol |
| 24 | (Z)-5-(3-chloro-2-(4-(dimethylamino)piperidin-1-yl)-5-(trifluoromethyl)benzylidene)thiazolidine-2,4-dione hydrochloride | 12.79 (brs, 1 H) 7.94 (d, 1 H) 7.82 (s, 1 H) 7.61 (s, 1 H) 3.84 (brs, 1 H) 3.46-3.18 (m, 4 H) 2.75 (d, 6 H) 2.10 (d, 2 H) 1.74 (dd, 2 H) | 434 | N,N-dimethylpiperidin-4-amine |
| 25 | (Z)-5-(3-chloro-2-((3-(dimethylamino)propyl)(methyl)amino)-5-(trifluoromethyl)benzylidene)thiazolidine-2,4-dione hydrochloride | 12.81 (brs, 1 H) 7.98 (d, 1 H) 7.81 (s, 1 H) 7.65 (d, 1 H) 3.15 (t, 2 H) 3.02 (brs, 2 H) 2.89 (s, 3 H) 2.72 (d, 6 H) 1.99-1.74 (m, 2 H) | 422 | N1,N1,N3-trimethylpropane-1,3-diamine |

| Ex. | Compound | ¹H NMR | m/z | SM |
|---|---|---|---|---|
| 26 | (Z)-5-(3-chloro-2-(4-(2-hydroxyethyl)-1,4-diazepan-1-yl)-5-(trifluoromethyl)benzyl-idene)thiazolidine-2,4-dione hydrochloride | 8.04 (brs, 1 H) 7.79 (d, 1 H) 7.63 (s, 1 H) 3.83 (t, 3 H) 3.71 (m, 2 H) 3.56 (m, 3 H) 3.33 (m, 6 H) 2.21 (m, 2 H) | 451 | 2-(1,4-diazepan-1-yl)ethanol |
| 27 | (Z)-5-(2-(4-butyl-1,4-diazepan-1-yl)-3-chloro-5-(trifluoromethyl)benzyl-idene)thiazolidine-2,4-dione hydrochloride | 10.76 (brs, 1 H) 8.06 (d, 1 H) 7.91 (brs, 1 H) 7.66 (d, 1 H) 3.69 (m, 3 H) 3.57 (brs, 1 H) 3.46 (m, 3 H) 3.14 (m, 3 H) 2.34 (brs, 1 H) 2.16 (brs, 1 H) 1.73 (d, 2 H) 1.32 (m, 2 H) 0.93 (t, 3 H) | 463 | 1-butyl-1,4-diazepane |
| 28 | (Z)-5-(3-chloro-2-(4-(2-hydroxyethyl)piperazin-1-yl)-5-(trifluoromethyl)benzyl-idene)thiazolidine-2,4-dione hydrochloride | 7.98 (d, 1 H) 7.82 (brs, 1 H) 7.64 (d, 1 H) 5.40 (brs, 1 H) 3.74 (m, 4 H) 3.56 (m, 3 H) 3.27 (m, 3 H) 3.18 (brs, 1 H) 3.11 (brs, 1 H) | 436 | 2-(piperazin-1-yl)ethanol |

| Ex. | Compound | ¹H NMR | m/z | SM |
|---|---|---|---|---|
| 29 | (Z)-5-(3-chloro-2-morpholino-5-(trifluoromethyl)benzylidene)thiazolidine-2,4-dione  | 12.76 (brs, 1 H) 7.94 (m, 2 H) 7.63 (d, 1 H) 3.71 (t, 4 H) 3.20 (brs, 4 H) | 394 | morpholine |
| 30 | (Z)-5-(2-(4-tert-butylpiperazin-1-yl)-3-chloro-5-(trifluoromethyl)benzylidene)thiazolidine-2,4-dione hydrochloride | 12.80 (brs, 1 H) 8.00 (d, 1 H) 7.85 (brs, 1 H) 7.65 (d, 1 H) 3.82 (m, 2 H) 3.56 (d, 2 H) 3.29 (dd, 2 H) 3.04 (m, 2 H) 1.39 (s, 9 H) | 449 | 1-tert-butylpiperazine |
| 31 | (Z)-5-(2-(1,4'-butylpiperidin-1'-yl)-3-chloro-5-(trifluoromethyl)benzylidene)thiazolidine-2,4-dione hydrochloride | 9.75 (brs, 1 H) 7.94 (d, 1 H) 7.81 (brs, 1 H) 7.62 (s, 1 H) 3.29 (m, 7 H) 2.96 (m, 2 H) 2.14 (d, 2 H) 1.78 (m, 7 H) 1.44 (brs, 1 H) | 474 | 1,4'-bipiperidine |

-continued

| Ex. | Compound | ¹H NMR | m/z | SM |
|---|---|---|---|---|
| 32 | (Z)-5-(3-chloro-2-(4-methylpiperazin-1-yl)-5-(trifluoromethyl)benzylidene)thiazolidine-2,4-dione hydrochloride 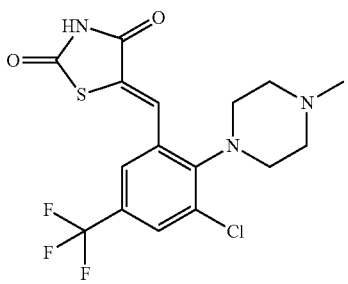 | 7.94 (brs, 1 H) 7.75 (d, 1 H) 7.63 (s, 1 H) 3.56-3.38 (m, 3 H) 3.31-3.21 (m, 5 H) 2.92 (s, 3 H) | 406 | 1-methylpiperazine |

Example 33

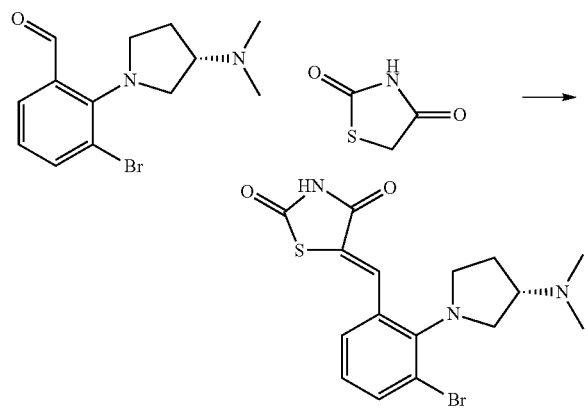

(S,Z)-5-(3-bromo-2-(3-(dimethylamino)pyrrolidin-1-yl)benzylidene)thiazolidine-2,4-dione hydrochloride A 100 mL round bottom flask was charged with a magnetic stir bar, (S)-3-bromo-2-(3-(dimethylamino)pyrrolidin-1-yl) benzaldehyde (Method 1) (0.370 g, 1.24 mmol), thiazolidine-2,4-dione (0.146 g, 1.24 mmol), and ethanol (4.15 ml). Piperidine (0.012 ml, 0.12 mmol) was then added and the reaction was heated to reflux for 2 h. Once the reaction was judged to be complete by LCMS, it was allowed to cool to rt and was conc. in vacuo to afford the product which was purified on 40 g of silica gel using ethyl acetate/methanol (3:1) as eluent to afford the free base which was suspended in methanol (~5 mL) and 1N HCl in diethyl ether (2 mL) and conc. in vacuo to afford (S,Z)-5-(3-bromo-2-(3-(dimethylamino)pyrrolidin-1-yl)benzylidene)thiazolidine-2,4-dione hydrochloride (0.141 g, 26.2%). ¹H NMR (300 MHz, DMSO-D6) δ ppm 12.68 (s, 1 H) 7.91 (s, 1 H) 7.77 (d, 1 H) 7.48 (d, 1 H) 7.33 (t, 1 H) 4.10-4.02 (m, 1 H) 3.62 (t, 2 H) 3.50-3.45 (m, 2 H) 2.81 (s, 6 H) 2.42-2.38 (m, 1 H) 2.31-2.21 (m, 1 H); m/z 398.

The following examples were prepared by the procedure of Example 33, using the appropriate starting materials. The following parent compounds obtained after chromatography (normal or reverse phase) may be converted to its corresponding hydrochloride salt as described in example 33, or similar procedure.

| Ex. | Compound | ¹H NMR | m/z | SM |
|---|---|---|---|---|
| 34 | (Z)-5-(2-((3S,5R)-3,5-dimethylpiperazin-1-yl)-5-(trifluoromethyl)benzylidene)thiazolidine-2,4-dione hydrochloride 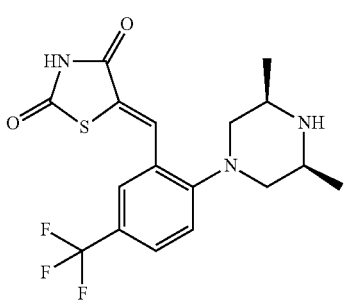 [SMILES: C[C@@H]1CN(c2ccc(C(F)(F)F)cc2/C=C2\SC(=O)NC2=O)C[C@H](C)N1] | 12.63 (s, 1 H) 8.99-8.94 (m, 1 H) 7.77 (d, 1 H) 7.72 (s, 2 H) 7.40 (d, 1 H) 3.49-3.43 (m, 2 H) 3.32 (d, 2 H) 2.92 (t, 2 H) 1.25 (d, 6 H) | 387 | 2-((3S,5R)-3,5-dimethylpiperazin-1-yl)-5-(trifluoromethyl)benzaldehyde Method 2 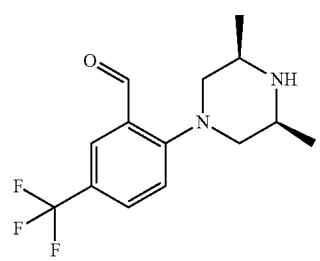 |

-continued

| Ex. | Compound | ¹H NMR | m/z | SM |
|---|---|---|---|---|
| 35 | (Z)-5-(2-((3S,5R)-3,5-dimethylpiperazin-1-yl)-3-methoxybenzylidene)thiazolidine-2,4-dione | 7.87 (brs, 1 H) 7.24 (t, 1 H) 7.20-7.10 (m, 1 H) 7.02 (d, 1 H) 3.81 (s, 3 H) 3.48-3.23 (m, 2 H) 3.17 (t, 2 H) 2.89 (d, 2 H) 1.30-1.09 (m, 6 H) | 348 | 2-((3S,5R)-3,5-dimethylpiperazin-1-yl)-3-methoxybenzaldehyde Method 3 |
| 36 | (S,Z)-5-(2-(3-(dimethylamino)pyrrolidin-1-yl)-3-methoxybenzylidene)thiazolidine-2,4-dione | 7.89 (s, 1 H) 7.26 (m, 1 H) 7.10 (m, 2 H) 3.84 (s, 3 H) 3.41-3.29 (m, 7 H) 3.24-3.13 (m, 4 H) 2.18 (m, 1 H) 1.99 (m, 1 H) | 348 | (S)-2-(3-(dimethylamino)pyrrolidin-1-yl)-3-methoxybenzaldehyde Method 4 |
| 37 | (Z)-5-(3-chloro-2-((3S,5R)-3,5-dimethylpiperazin-1-yl)benzylidene)thiazolidine-2,4-dione | 7.80 (s, 1 H) 7.50 (brs, 1 H) 7.38 (d, 1 H) 7.30 (brs, 1 H) 3.34-3.02 (m, 6 H) 1.26-1.09 (m, 6 H) | 352 | 3-chloro-2-((3S,5R)-3,5-dimethylpiperazin-1-yl)benzaldehyde Method 5 |
| 38 | (S,Z)-5-(3-chloro-2-(3-(dimethylamino)pyrrolidin-1-yl)benzylidene)thiazolidine-2,4-dione | 7.73 (s, 1 H) 7.52-7.47 (m, 2 H) 7.47 (s, 1 H) 7.33-7.31 (m, 1 H) 3.58-3.52 (m, 1 H) 3.48 (m, 1 H) 3.37-3.27 (m, 3 H) 2.56 (s, 6 H) 2.26-2.35 (m, 1 H) 2.08 (m, 1 H) | 352 | (S)-3-chloro-2-(3-(dimethylamino)pyrrolidin-1-yl)benzaldehyde Method 6 |

-continued

| Ex. | Compound | ¹H NMR | m/z | SM |
|---|---|---|---|---|
| 39 | (R,Z)-5-(2-(3-(dimethylamino)pyrrrolidin-1-yl)-4,5-dimethoxybenzylidene)thiazolidine-2,4-dione | 7.75 (s, 1 H) 6.98 (s, 1 H) 6.68 (s, 1 H) 3.83 (s, 3 H) 3.72 (s, 3 H) 3.24-3.06 (m, 4 H) 2.50 (m, 1 H) 2.32 (s, 6 H) 2.12 (m, 1 H) 1.84 (m, 1 H) | 378 | (R)-2-(3-(dimethylamino)pyrrolidin-1-yl)-4,5-dimethoxybenzaldehyde Method 7 |
| 40 | (S,Z)-5-(2-(3-(dimethylamino)pyrrolidin-1-yl)-4,5-dimethoxybenzylidene)thiazolidine-2,4-dione | 7.76 (s, 1 H) 6.98 (s, 1 H) 6.68 (s, 1 H) 3.83 (s, 3 H) 3.72 (s, 3 H) 3.26-3.01 (m, 5 H) 2.32 (s, 6 H) 2.15-2.09 (m, 1 H) 1.90-1.81 (m, 1 H) | 378 | (S)-2-(3-(dimethylamino)pyrrolidin-1-yl)-4,5-dimethoxybenzaldehyde Method 8 |
| 41 | (5Z)-5-{2-[4-(hydroxymethyl)piperidin-1-yl]-4,5-dimethoxybenzylidene}-1-,3-thiazolidine-2,4-dione | 12.44 (brs, 1 H) 7.94 (s, 1 H) 7.05-6.87 (m, 1 H) 6.80 (s, 1 H) 4.54 (t, 1 H) 3.85 (s, 3 H) 3.76 (s, 3 H) 3.17 (d, 1 H) 3.03 (d, 2 H) 2.71 (t, 2 H) 1.75 (brs, 2 H) 1.56-1.26 (m, 3 H) | 379 | 2-(4-(hydroxymethyl)piperidin-1-yl)-4,5-dimethoxybenzaldehyde Method 9 |

| Ex. | Compound | ¹H NMR | m/z | SM |
|---|---|---|---|---|
| 42 | (5Z)-5-[2-(4-hydroxypiperidine-1-yl)-4,5-dimethoxybenzylidene]-1,3-thiazolidine-2,4-dione | 12.50 (brs, 1 H) 8.02 (s, 1 H) 6.99 (s, 1 H) 6.92-6.82 (m, 1 H) 4.79 (d, 1 H) 3.90 (s, 3 H) 3.82 (s, 3 H) 3.74-3.58 (m, 1 H) 3.13-2.96 (m, 2 H) 2.88-2.71 (m, 2 H) 2.01-1.81 (m, 2 H) 1.78-1.58 (m, 2 H) | 365 | 2-(4-hydroxypiperidin-1-yl)-4,5-dimethoxybenzaldehyde Method 10 |
| 43 | (5Z)-5-{2-[3-(dimethylamino)pyrrolidin-1-yl]-5-methoxybenzylidene}-1,3-thiazolidine-2,4-dione | 7.51 (s, 1 H) 7.03 (d, 1 H) 6.99 (d, 1 H) 6.84 (dd, 1 H) 3.72 (s, 3 H) 3.09-3.21 (m, 1 H) 2.82-3.09 (m, 4 H) 2.23 (s, 6 H) 2.06 (d, 1 H) 1.73-1.85 (m, 1 H) | 348 | 2-(3-(dimethylamino)pyrrolidin-1-yl)-5-methoxybenzaldehyde Method 11 |
| 44 | (5Z)-5-{2-[4-(dimethylamino)piperidin-1-yl]-5-methoxybenzylidene}-1,3-thiazolidine-2,4-dione | 7.59 (s, 1 H) 7.11-6.99 (m, 2 H) 6.85 (dd, 1 H) 3.75 (s, 3 H) 3.03 (m, 2 H) 2.64-2.54 (m, 2 H) 2.44-2.33 (m, 7 H) 1.91 (s, 2 H) 1.62 (dd, 2 H) | 362 | 2-(4-(dimethylamino)piperidin-1-yl)-5-methoxybenzaldehyde Method 12 |

-continued

| Ex. | Compound | ¹H NMR | m/z | SM |
|---|---|---|---|---|
| 45 | (5Z)-5-[2-(3-hydroxypyrrolidin-1-yl)-4,5-dimethoxybenzylidene]-1,3-thiazolidine-2,4-dione | 12.32 (brs, 1 H) 7.88 (s, 1 H) 6.93 (s, 1 H) 6.66 (s, 1 H) 4.34 (brs, 1 H) 3.83 (s, 3 H) 3.72 (s, 3 H) 3.55-3.29 (m, 3 H) 3.22 (brs, 1 H) 2.90 (d, 1 H) 2.16-1.94 (m, 1 H) 1.84 (d, 1 H) | 351 | 2-(3-hydroxypyrrolidin-1-yl)-4,5-diemethoxybenzaldehyde Method 13 |
| 46 | (5Z)-5-(4,5-dimethoxy-2-pyrrolidin-1-ylbenzylidene)-1,3-thiazolidine-2,4-dione | 12.21 (brs, 1 H) 7.86 (s, 1 H) 6.94 (s, 1 H) 6.65 (s, 1 H) 3.83 (s, 3 H) 3.72 (s, 3 H) 3.12 (brs, 4 H) 1.90 (brs, 4 H) | 335 | 4,5-dimethoxy-2-(pyrrolidin-1-yl)benzaldehyde Method 14 |
| 47 | (5Z)-5-{2-[[2-(dimethylamino)ethyl](methyl)amino]benzylidene}-1,3-thiazolidine-2,4-dione | 7.62 (s, 1 H) 7.48 (d, 1 H) 7.32 (t, 1 H) 7.17 (d, 1 H) 7.10 (t, 1 H) 3.06 (t, 2 H) 2.86-2.62 (m, 5 H) 2.36 (s, 6 H) | 306 | 2-((2-(dimethylamino)ethyl)(methyl)amino)benzaldehyde Method 15 |

| Ex. | Compound | ¹H NMR | m/z | SM |
|---|---|---|---|---|
| 48 | (5Z)-5-{2-[3-(dimethylamino)pyrrolidin-1-yl]benzylidene}-1,3-thiazolidine-2,4-dione | 7.52 (s, 1 H) 7.27-7.21 (m, 1 H) 7.14-7.05 (m, 1 H) 6.84 (d, 1 H) 6.77 (t, 1 H) 3.17 (s, 1 H) 3.16-3.09 (m, 1 H) 3.06-2.94 (m, 2 H) 2.86-2.77 (m, 1 H) 2.16-2.11 (m, 6 H) 2.03-1.92 (m, 1 H) 1.66 (dd, 1 H) | 318 | 2-(3-(dimethylamino)pyrrolidin-1-yl)benzaldehyde Method 16 |
| 49 | (5Z)-5-{2-[4-(dimethylamino)piperidin-1-yl]benzylidene}-1,3-thiazolidine-2,4-dione | 7.64 (s, 1 H) 7.50 (d, 1 H) 7.35-7.27 (m, 1 H) 7.12 (t, 2 H) 3.22 (m, 2 H) 2.88 (m, 1 H) 2.68 (t, 2 H) 2.63 (s, 6 H) 2.04 (s, 2 H) 1.73 (td, 2 H) | 332 | 2-(4-(dimethylamino)piperidin-1-yl)benzaldehyde Method 17 |
| 50 | (5Z)-5-[2-(4-isopropylpiperazin-1-yl)benzylidene]-1,3-thiazolidine-2,4-dione | 7.80 (s, 1 H) 7.49-7.43 (m, 1 H) 7.43-7.39 (m, 1 H) 7.22-7.13 (m, 2 H) 2.99-2.98 (m, 5 H) 2.80 (s, 4 H) 1.13-1.04 (m, 6 H) | 332 | 2-(4-isopropylpiperazin-1-yl)benzaldehyde Method 18 |

-continued

| Ex. | Compound | ¹H NMR | m/z | SM |
|---|---|---|---|---|
| 51 | (5Z)-5-{2-[[2-(dimethylamino)ethyl](methyl)amino]-4,5-dimethoxybenzylidene}-1,3-thiazolidine-2,4-dione | 7.78 (s, 1 H) 7.02 (s, 1 H) 6.85 (s, 1 H) 3.83 (s, 3 H) 3.76 (s, 3 H) 3.11-2.98 (m, 2 H) 2.76-2.65 (m, 5 H) 2.37 (s, 6 H) | 364 | 2-((2-(dimethylamino)ethyl)(methyl)amino)-4,5-dimethoxybenzaldehyde Method 19 |
| 52 | (5Z)-5-{2-[4-(dimethylamino)pyrrolidin-1-yl]-4,5-dimethoxybenzylidene}-1,3-thiazolidine-2,4-dione | 7.76 (s, 1 H) 6.98 (s, 1 H), 6.68 (s, 1 H), 3.83 (s, 3 H), 3.72 (s, 3 H) 3.25 (m, 1 H), 3.13 (m, 2 H), 3.06 (m, 2 H), 2.32 (s, 6 H), 2.15-2.09 (m, 1 H) 1.90-1.81 (m, 1 H) | 378 | 2-(3-(dimethylamino)pyrrolidin-1-yl)-4,5-dimethoxybenzaldehyde Method 20 |
| 53 | (5Z)-5-{2-(4-isopropylpiperazin-1-yl)-4,5-dimethoxybenzylidene}-thiazolidine-2,4-dione | 7.86 (s, 1 H) 6.95 (s, 1 H) 6.77 (s, 1 H) 3.81 (s, 3 H) 3.76-3.67 (m, 3 H) 2.91-2.79 (m, 5 H) 2.71 (s, 4 H) 1.08-1.00 (m, 6 H) | 392 | 2-(4-isopropylpiperazin-1-yl)-4,5-dimethoxybenzaldehyde Method 21 |

-continued

| Ex. | Compound | ¹H NMR | m/z | SM |
|---|---|---|---|---|
| 54 | (5Z)-5-{2-(4-(dimethylamino)piperidin-1-yl)-4,5-dimethoxybenzylidene}-thiazolidine-2,4-dione | 7.48 (s, 1 H) 6.82 (s, 1 H) 6.51 (s, 1 H) 3.58 (s, 3 H) 3.51 (s, 3 H) 2.87 (d, 2 H) 2.47 (m, 3 H) 2.35 (s, 6 H) 1.79 (d, 2 H) 1.49 (d, 2 H) | 392 | 2-(4-(dimethylamino)piperidin-1-yl)-4,5-dimethoxybenzaldehyde Method 22 |
| 55 | (Z)-tert-butyl 4-(2-((2,4-dioxothiazolidin-5-ylidene)methyl)-4-(trifluoromethyl)phenyl)piperazine-1-carboxylate | 12.65 (s, 1 H) 7.82 (s, 1 H) 7.72 (s, 1 H) 7.53 (s, 1 H) 3.59-3.50 (m, 1 H) 3.38-3.30 (m, 4 H) 2.56 (s, 6 H) 2.31-2.28 (m, 1 H) 2.09-2.01 (m, 1 H) | 458 | tert-butyl 4-(2-formyl-4-(trifluoromethyl)phenyl)piperazine-1-carboxylate Method 23 |
| 56 | (Z)-5-(2-(3-(dimethylamino)pyrrolidin-1-yl)-5-nitrobenzylidene)thiazolidine-2,4-dione hydrochloride | 12.64 (s, 1 H) 8.22 (d, 1 H) 8.12 (d, 1 H) 7.95 (d, 1 H) 7.04 (d, 1 H) 3.95-3.90 (m, 1 H) 3.70-3.65 (m, 2 H) 3.56-3.51 (m, 2 H) 2.79 (s, 6 H) 2.41-2.35 (m, 1 H) 2.34-2.22 (m, 1 H) | 363 | 2-(3-(dimethylamino)pyrrolidin-1-yl)-5-nitrobenzaldehyde Method 24 |

-continued

| Ex. | Compound | ¹H NMR | m/z | SM |
|---|---|---|---|---|
| 57 | (Z)-4-(3-(dimethylamino)pyrrolidin-1-yl)-3-((2,4-dioxothiazolidin-5-ylidene)methyl)benzamide hydrochloride | 12.47 (s, 1 H) 7.92-7.84 (m, 4 H) 7.23 (s, 1 H) 7.03 (d, 1 H) 3.98-3.91 (m, 1 H) 3.53-3.49 (m, 2 H) 3.46-3.39 (m, 2 H) 2.79 (s, 6 H) 2.34-2.19 (m, 2 H) | 361 | 4-(3-(dimethylamino)pyrrolidin-1-yl)-3-formylbenzamide Method 25 |
| 58 | (Z)-tert-butyl 4-(2-((2,4-dioxothiazolidin-5-ylidene)methyl)phenyl)piperazine-1-carboxylate | 12.55 (s, 1 H) 7.92 (s, 1 H) 7.46-7.44 (m, 2 H) 7.21-7.18 (m, 2 H) 3.48 (brs, 4 H) 2.86 (brs, 4 H) 1.43 (s, 9 H) | 389 | tert-butyl 4-(2-formylphenyl)piperazine-1-carboxylate Method 26 |
| 59 | (Z)-5-(3-methoxy-4-(2-(piperidin-1-yl)ethoxy)benzylidene)thiazolidine-2,4-dione | 7.78 (s, 1 H) 7.27 (s, 1 H) 7.21 (s, 2 H) 4.47 (t, 2 H) 3.84 (s, 3 H) 3.49 (t, 4 H) 3.04 (brs, 2 H) 1.80 (d, 4 H) 1.64 (brs, 1 H) 1.43 (brs, 1 H) | 363 | 3-methoxy-4-(2-(piperidin-1-yl)ethoxy)benzaldehyde Commercial |

-continued

| Ex. | Compound | ¹H NMR | m/z | SM |
|---|---|---|---|---|
| 60 | (Z)-5-(2-(2-hydroxyethoxy)benzylidene)thiazolidine-2,4-dione | 12.58 (brs, 1 H) 8.06 (s, 1 H) 7.57-7.32 (m, 2 H) 7.26-7.03 (m, 2 H) 4.95 (brs, 1 H) 4.13 (t, 2 H) 3.77 (brs, 2 H) | 266 | 2-(2-hydroxyethoxy)benzaldehyde Commercial |
| 61 | (Z)-5-(5-methoxy-2-(2-(piperidin-1-yl)ethoxy)benzylidene)thiazolidine-2,4-dione | 7.80 (s, 1 H) 7.10 (d, 1 H) 7.04-6.95 (m, 2 H) 4.22 (t, 2 H) 3.75 (s, 3 H) 3.07 (t, 2 H) 2.84 (s, 4 H) 1.62 (dq, 4 H) 1.46 (d, 2 H) | 363 | 5-methoxy-2-(2-(piperidin-1-yl)ethoxy)benzaldehyde Method 27 |
| 62 | (Z)-5-(5-methoxy-2-(2-morpholinoethoxy)benzylidene)thiazolidine-2,4-dione | 7.99 (s, 1 H) 7.22-7.10 (m, 1 H) 7.09-6.97 (m, 1 H) 6.91 (d, 1 H) 4.17 (t, 2 H) 3.76 (s, 3 H) 3.64-3.51 (m, 4 H) 2.75 (t, 2 H) 2.51-2.62 (m, 4 H) | 365 | 5-methoxy-2-(2-morpholinoethoxy)benzaldehyde Method 28 |

| Ex. | Compound | $^1$H NMR | m/z | SM |
|---|---|---|---|---|
| 63 | (Z)-5-(2-(2-(diethylamino)ethoxy)-5-methoxybenzylidene)thiazolidine-2,4-dione | 7.77 (s, 1 H) 7.08-7.05 (m, 1 H) 7.03-6.95 (m, 2 H) 4.19 (t, 2 H) 3.75 (s, 3 H) 3.25-3.14 (m, 2 H) 2.95 (q, 4 H) 1.17-1.08 (m, 6 H) | 352 | 2-(2-(diethylamino)ethoxy)-5-methoxybenzaldehyde Method 29 |
| 64 | (Z)-5-(2-(2-(diethylamino)ethoxy)benzylidene)thiazolidine-2,4-dione | 7.84 (s, 1 H) 7.47 (d, 1 H) 7.43-7.35 (m, 1 H) 7.14-7.04 (m, 2 H) 4.24 (t, 2 H) 3.20 (m, 2 H) 2.90 (q, 4 H) 1.13 (t, 6 H) | 321 | 2-(2-(diethylamino)ethoxy)benzaldehyde Method 30 |
| 65 | (Z)-5-(4,5-dimethoxy-2-(pyridin-3-yl)benzylidene)thiazolidine-2,4-dione | 12.55 (brs, 1 H) 8.73-8.61 (m, 1 H) 8.58 (brs, 1 H) 7.81 (dd, 1 H) 7.53 (dd, 1 H) 7.46 (s, 1 H) 7.13 (d, 2 H) 3.89 (d, 6 H) | 343 | 4,5-dimethoxy-2-(pyridin-3-yl)benzaldehyde Method 31 |

-continued

| Ex. | Compound | ¹H NMR | m/z | SM |
|---|---|---|---|---|
| 66 | (Z)-5-(4,5-dimethoxy-2-(pyridin-4-yl)benzylidene)thiazolidine-2,4-dione | 12.58 (brs, 1 H) 8.67 (d, 2 H) 7.48 (d, 1 H) 7.41 (d, 2 H) 7.12 (d, 2 H) 3.89 (s, 6 H) | 343 | 4,5-dimethoxy-2-(pyridin-4-yl)benzaldehyde Method 32 |
| 67 | (Z)-5-((1H-indol-3-yl)methylene)thiazolidine-2,4-dione | 7.21 (dddd, 2 H) 7.50 (d, 1 H) 7.71 (d, 1 H) 7.87 (d, 1 H) 7.99 (s, 1 H) 12.07 (brs, 2 H) | 245 | 1H-indole-3-carbaldehyde Commercial |
| 68 | (Z)-5-((1H-indazol-3-yl)methylene)thiazolidine-2,4-dione | 7.28 (t, 1 H) 7.52-7.39 (m, 1 H) 7.64 (d, 1 H) 8.22-8.03 (m, 2 H) 12.41 (d, 1 H) 13.96 (s, 1 H) | 246 | 1H-indazole-3-carbaldehyde Commercial |
| 69 | (Z)-5-((6-oxo-1,6-dihydropyridin-3-yl)methylene)thiazolidine-2,4-dione | 11.99 (brs, 1 H) 7.74 (brs, 1 H) 7.69-7.58 (m, 1 H) 7.27 (s, 1 H) 6.43 (d, 1 H) | 223 | 6-oxo-1,6-dihydropyridine-3-carbaldehyde Commercial |

-continued

| Ex. | Compound | ¹H NMR | m/z | SM |
|---|---|---|---|---|
| 70 | (Z)-5-((2-oxo-1,2-dihydropyridin-3-yl)methylene)thiazolidine-2,4-dione | 12.43 (brs, 1 H) 12.16 (brs, 1 H) 7.73 (s, 1 H) 7.69 (dd, 1 H) 7.57 (d, 1 H) 6.38 (t, 1 H) | 223 | 2-oxo-1,2-dihydropyridin-3-carbaldehyde Commercial |
| 71 | (Z)-5-((1H-pyrazol-4-yl)methylene)thiazolidine-2,4-dione | 13.51 (brs, 1 H) 12.37 (brs, 1 H) 8.20 (s, 1 H) 7.82 (s, 1 H) 7.74 (s, 1 H) | 196 | 1H-pyrazole-4-carbaldehyde Commercial |
| 72 | (Z)-5-(pyridin-4-ylmethylene)thiazolidine-2,4-dione | 12.61 (brs, 1 H) 8.71 (d, 2 H) 7.74 (s, 1 H) 7.53 (d, 2 H) | 207 | 4-pyridinecarboxaldehyde Commercial |
| 73 | (5Z)-5-[(1-methyl-1H-1,2,3-benzotriazol-5-yl)methylene]-1,3-thiazolidine-2,4-dione | 12.65 (brs, 1 H) 8.28 (s, 1 H) 8.00-7.98 (m, 2 H) 7.76 (d, 1 H) 4.33 (s, 3 H) | 259 | 1-methyl-1H-benzo[d][1,2,3]triazole-5-carbaldehyde Commercial |
| 74 | (5Z)-5-(3,4-dimethoxybenzylidene)-1,3-thiazolidine-2,4-dione | 12.51 (brs, 1 H) 7.74 (s, 1 H) 7.19-7.09 (m, 3 H) 3.82 (s, 3 H) 3.80 (s, 3 H) | 266 | 3,4-dimethoxybenzaldehyde Commercial |

-continued

| Ex. | Compound | ¹H NMR | m/z | SM |
|---|---|---|---|---|
| 75 | (5Z)-5-[(1-methyl-1H-indol-6-yl)methylene]-1,3-thiazolidine-2,4-dione | 12.49 (brs, 1 H) 7.92 (s, 1 H) 7.68 (d, 1 H) 7.54 (s 1 H) 7.25 (d, 1 H) 6.50 (s, 1 H) 3.84 (s, 3 H) | | 1-methyl-1H-indole-6-carbaldehyde Commercial |
| 76 | (5Z)-5-[(1-methyl-1H-indol-5-yl)methylene]-1,3-thiazolidine-2,4-dione | 12.45 (brs, 1 H) 7.90 (s, 1 H) 7.84 (d, 1 H) 7.59 (d, 1 H) 7.44 (d, 1 H) 7.38 (d 1 H) 6.57 (d, 1 H) 3.82 (s, 3 H) | 259 | 1-methyl-1H-indole-5-carbaldehyde Commercial |
| 77 | (5Z)-5-(quinolin-6-ylmethylene)-1,3-thiazolidine-2,4-dione trifluoroacetate | 12.70 (brs, 1 H) 8.97 (d, 1 H) 8.51 (d, 1 H) 8.24 (s, 1 H) 8.12 (d, 1 H) 7.96-7.93 (m, 2 H) 7.64-7.61 (m, 1 H) | 257 | quinoline-6-carbaldehyde Commercial |
| 78 | (5Z)-5-(1H-indol-5-ylmethylene)-1,3-thiazolidine-2,4-dione | 12.43 (brs, 1 H) 11.44 (brs, 1 H) 7.85 (d, 1 H) 7.53-7.51 (m, 2 H) 7.45-7.44 (m, 1 H) 7.33 (d, 1 H) 6.56 (s, 1 H) | 245 | 1H-indole-5-carbaldehyde Commercial |
| 79 | (5Z)-5-(1H-indol-6-ylmethylene)-1,3-thiazolidine-2,4-dione trifluoroacetate | 12.47 (brs, 1 H) 11.48 (brs, 1 H) 7.90 (s, 1 H) 7.69-7.66 (m, 2 H) 7.55-7.52 (m, 1 H) 7.23 (d, 1 H) 6.51 (s, 1 H) | 245 | 1H-indole-6-carbaldehyde Commercial |

-continued

| Ex. | Compound | ¹H NMR | m/z | SM |
|---|---|---|---|---|
| 80 | (5Z)-5-(1H-pyrrolo[2,3-b]pyridin-5-ylmethylene)-1,3-thiazolidine-2,4-dione | 12.02 (brs, 1 H) 8.49 (d, 1 H) 8.15 (d, 1 H) 7.92 (s, 1 H) 7.58 (t, 1 H) 6.59 (brs, 1 H) | 246 | 1H-pyrrolo[2,3-b]pyridine-5-carbaldehyde Commercial |
| 81 | (5Z)-5-{2-[3-(dimethylamino)propoxy]benzylidene}-1,3-thiazolidine-2,4-dione | 8.16 (s, 1 H) 7.76 (s, 1 H) 7.48 (d, 1 H) 7.34 (s, 1 H) 7.08 (d, 1 H) 4.11 (t, 2 H) 2.86 (t, 2 H) 2.53 (s, 6 H) 2.10-1.98 (m, 2 H) | 307 | 2-[3-(dimethylamino)propoxy]benzaldehyde Commercial |
| 82 | (5Z)-5-(2-morpholin-4-ylbenzylidene)-1,3-thiazolidine-2,4-dione | 7.89 (s, 1 H) 7.46 (d, 1 H) 7.45-7.41 (m, 1 H) 7.22-7.14 (m, 2 H) 3.80-3.69 (m, 4 H) 2.93-2.82 (m, 4 H) | 291 | 2-morpholin-4-ylbenzaldehyde Commercial |
| 83 | (5Z)-5-(3-morpholin-4-ylbenzylidene)-1,3-thiazolidine-2,4-dione trifluoroacetate | 12.58 (brs, 1 H) 7.74 (s, 1 H) 7.37 (t, 1 H) 7.12 (s, 1 H) 7.07 (dd, 1 H) 7.00 (d, 1 H) 3.79-3.69 (m, 4 H) 3.20-3.09 (m, 4 H) | 290 | 3-morpholin-4-ylbenzaldehyde Commercial |

-continued

| Ex. | Compound | ¹H NMR | m/z | SM |
|---|---|---|---|---|
| 84A | (5Z)-5-[2-(4-methylpiperazin-1-yl)benzylidene]-1,3-thiazolidine-2,4-dione | 7.78 (s, 1 H) 7.46 (d, 1 H) 7.42-7.35 (m, 1 H) 7.19-7.11 (m, 2 H) 2.94 (t, 4 H) 2.70 (brs, 4 H) 2.40 (s, 3 H) | 304 | 2-(4-methylpiperazin-1-yl)benzaldehyde Commercial |
| 84B | (Z)-5-(3-(3-(4-methylpiperazin-1-yl)propoxy)benzylidene)thiazolidine-2,4-dione | 11.37 (brs, 1 H) 7.54 (s, 1 H) 7.38 (t, 1 H) 7.12 (m, 2 H), 6.96 (m, 1 H) 4.58 (s, 3 H) 4.05 (t, 2 H) 3.00-2.55 (m, 10 H) 1.93 (m, 2 H) | 362 | 3-(3-(4-methylpiperazin-1-yl)propoxy)benzaldehyde hydrochloride |
| 84C | (Z)-2-(3-((2,4-dioxothiazolidin-5-ylidene)methyl)phenoxy)acetamide | 12.62 (s, 1 H) 7.73 (s, 1 H) 7.60 (s, 1 H) 7.44 (t, 1 H) 7.41 (s, 1 H) 7.19 (d, 1 H) 7.14 (m, 1 H) 7.05 (dd, 1 H) 4.48 (s, 2 H) | 279 | 2-(3-formylphenoxy)acetamide |

-continued

| Ex. | Compound | ¹H NMR | m/z | SM |
|---|---|---|---|---|
| 84D | (Z)-5-(3-(3-(piperidin-1-yl)propoxy)benzylidene)thiazolidine-2,4-dione | 7.30 (t, 1 H) 7.24 (s, 1 H) 7.08 (m, 2 H) 6.85 (dd, 1 H) 4.01 (t, 2 H) 2.45 (t, 2 H) 2.40 (m, 4 H) 1.88 (m, 2 H) 1.50 (m, 4 H) 1.38 (m, 2 H) | 347 | 3-(3-(piperidin-1-yl)propoxy)benzaldehyde hydrochloride |
| 84E | (Z)-5-(3-((4-methylpiperazin-1-yl)methyl)benzylidene)thiazolidine-2,4-dione | 7.59 (s, 1 H) 7.51 (s, 1H) 7.46 (m, 2 H) 7.34 (m, 1 H) 3.59 (s, 2 H) 2.96 (m, 4 H) 2.59 (m, 4 H) 2.58 (s, 3 H) | 318 | 3-((4-methylpiperazin-1-yl)methyl)benzaldehyde |
| 84F | (Z)-N-(2-(dimethylamino)ethyl)-2'-((2,4-dioxothiazolidin-5-ylidene)methyl)-N-methylbiphenyl-4-sulfonamide | 7.90 (d, 2 H) 7.69 (d, 1 H) 7.65-7.49 (m, 4 H) 7.49-7.40 (m, 1 H) 7.31 (s, 1 H) 3.24 (t, 2 H) 2.83 (t, 2 H) 2.78 (s, 3 H) 2.48 (s, 6 H) | 445 | N-(2-(dimethylamino)ethyl)-2'-formyl-N-methylbiphenyl-4-sulfonamide Method 32B |

| Ex. | Compound | ¹H NMR | m/z | SM |
|---|---|---|---|---|
| 84G | (S)-5-(2-(3-(dimethylamino)pyrrolidin-1-yl)-5-methoxybenzylidene)thiazolidine-2,4-dione | | 348 | (S)-2-(3-(dimethylamino)pyrrolidin-1-yl)-5-methoxybenzaldehyde Method 104 |
| 84H | (S)-5-(2-(3-(dimethylamino)pyrrolidin-1-yl)-5-(trifluoromethyl)benzylidene)thiazolidine-2,4-dione | 12.55 (s, 1 H) 11.25 (brs, 1 H) 7.95 (s, 1 H) 7.78 (s, 1 H) 7.60 (m, 1 H), 7.15 (m, 1 H) 4.00 (m, 1 H) 3.65 (m, 2 H) 3.40 (m, 1 H) 3.32 (m, 1 H) 2.80 (s, 6 H) 2.35 (m, 1 H) 2.20 (m, 1 H) | 386 | (S)-2-(3-(dimethylamino)pyrrolidin-1-yl)-5-(trifluoromethyl)benzaldehyde Method 105 |
| 84I | (S)-5-(5-chloro-2-(3-(dimethylamino)pyrrolidin-1-yl)benzylidene)thiazolidine-2,4-dione | 12.55 (s, 1H) 7.81 (s, 1H), 7.93 (m, 2H), 7.12 (m, 1 H), 3.90(m, 1H), 3.45-3.30 (m, 2H), 3.29 (m, 1H), 3.15 (m, 1H), 2.80 (s, 6 H), 2.35 (m, 1H), 2.20 (m, 1H) | 352 | (S)-5-chloro-2-(3-(dimethylamino)pyrrolidin-1-yl)benzaldehyde Method 106 |

| Ex. | Compound | ¹H NMR | m/z | SM |
|---|---|---|---|---|
| 84J | (S)-5-(2-(3-(dimethylamino)pyrrolidin-1-yl)-4-methylbenzylidene)thiazolidine-2,4-dione | | 332 | (S)-2-(3-(dimethylamino)pyrrolidin-1-yl)-4-methylbenzaldehyde Method 107 |
| 84K | (S)-5-(2-(3-(dimethylamino)pyrrolidin-1-yl)-5-fluorobenzylidene)thiazolidine-2,4-dione | 12.55 (s, 1 H) 11.40 (s, 1 H) 7.80 (s, 1 H) 7.30-7.15 (m, 3 H) 3.92 (m, 1 H) 3.45 (m, 1 H) 3.35 (m, 1 H) 3.18 (m, 1 H) 3.15 (m, 1 H) 3.80 (d, 6 H) 2.30 (m, 1 H), 2.20 (m, 1H) | 336 | (S)-2-(3-(dimethylamino)pyrrolidin-1-yl)-5-fluorobenzaldehyde Method 108 |
| 84L | (S)-5-(2-(3-(dimethylamino)pyrrolidin-1-yl)-5-methylbenzylidene)thiazolidine-2,4-dione | | 332 | (S)-2-(3-(dimethylamino)pyrrolidin-1-yl)-5-methylbenzaldehyde Method 109 |

-continued

| Ex. | Compound | ¹H NMR | m/z | SM |
|---|---|---|---|---|
| 84M | (S)-5-(5-bromo-2-(3-(dimethylamino)pyrrolidin-1-yl)benzylidene)thiazolidine-2,4-dione | | 397 | (S)-5-bromo-2-(3-(dimethylamino)pyrrolidin-1-yl)benzaldehyde Method 110 |
| 84N | (S)-5-(2-(3-(dimethylamino)pyrrolidin-1-yl)-3-fluorobenzylidene)thiazolidine-2,4-dione | 12.55 (s, 1 H) 10.34 (s, 1 H) 7.87 (d, 1H) 7.33-7.21 (m, 3 H) 3.93 (m, 1 H) 3.40 (m, 2 H) 3.25 (m, 1 H) 3.18 (m, 1 H) 2.79 (s, 6 H) 2.26 (m, 1H) 2.12 (m, 1H) | 336 | (S)-2-(3-(dimethylamino)pyrrolidin-1-yl)-3-fluorobenzaldehyde Method 111 |
| 84O | (S)-5-(2-chloro-6-(3-(dimethylamino)pyrrolidin-1-yl)benzylidene)thiazolidine-2,4-dione | | 352 | (S)-2-chloro-6-(3-(dimethylamino)pyrrolidin-1-yl)benzaldehyde Method 112 |

Example 85

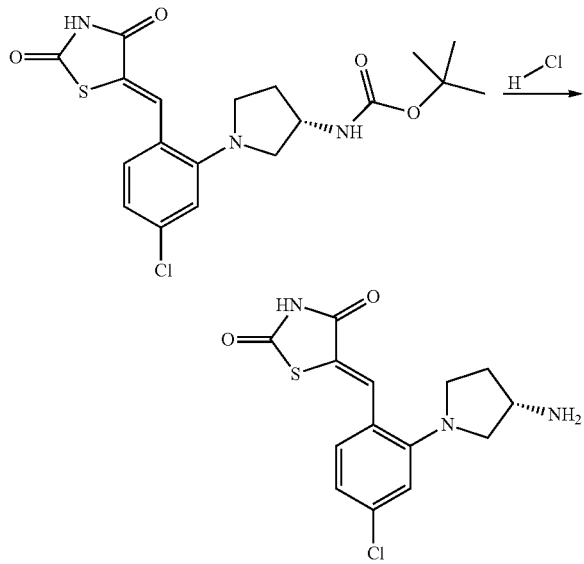

(S,Z)-5-(2-(3-aminopyrrolidin-1-yl)-4-chlorobenzylidene)thiazolidine-2,4-dione hydrochloride A 100 mL round bottom flask was charged with a magnetic stir bar, (S,Z)-tert-butyl1-(5-chloro-2-((2,4-dioxothiazolidin-5-ylidene)methyl)phenyl)pyrrolidin-3-ylcarbamate (Method 33) (1.300 g, 3.07 mmol), MeOH (10.22 ml), and a 1N sol'n of HCl in diethyl ether (2.294 ml, 46.00 mmol). The reaction mixture was allowed to stir overnight at rt before being conc. in vacuo to afford the product as its hydrochloride salt. This material was dissolved in DMSO and purified via reverse phase HPLC to afford fractions that were conc. in vacuo, suspended in methanol (~5 mL) and 1N HCl in diethyl ether (~2 mL). This mixture was conc. in vacuo to afford (S,Z)-5-(2-(3-aminopyrrolidin-1-yl)-4-chlorobenzylidene)thiazolidine-2,4-dione hydrochloride (0.710 g, 64.3%). $^1$H NMR (300 MHz, DMSO-D6) δ ppm 12.51 (s, 1 H) 8.36 (s, 2 H) 7.85 (s, 1 H) 7.35 (d, 1 H) 6.96 (dd, 2 H) 3.90-3.75 (m, 1 H) 3.55-3.47 (m, 1 H) 3.40 (dd, 1 H) 3.31-3.21 (m, 1 H) 3.18-3.10 (m, 1 H) 2.29-2.18 (m, 1 H) 2.10-1.96 (m, 1 H); m/z 325.

The following examples were prepared by the procedure of Example 85, using the appropriate starting materials. The following parent compounds obtained after chromatography may be converted to their corresponding hydrochloride salt in a manner similar as described in example 85, or similar procedure.

| Ex. | Compound | 1H NMR | m/z | SM |
|---|---|---|---|---|
| 86 | (S,Z)-5-(2-(3-aminopyrrolidin-1-yl)-3-chlorobenzylidene)thiazolidine-2,4-dione hydrochloride | 12.69 (s, 1 H) 8.35 (brs, 2 H) 7.94 (s 1 H) 7.57 (d, 1 H) 7.41-7.35 (m, 2 H) 3.95-3.88 (m, 1 H) 3.53-3.26 (m, 4 H) 2.37-2.31 (m, 1 H) 2.08-2.01 (m, 1 H) | 324 | (S,Z)-tert-butyl 1-(2-chloro-6-((2,4-dioxothiazolidin-5-ylidene)methyl)phenyl)pyrrolidin-3-ylcarbamate Method 34 |
| 87 | (Z)-5-(2-(piperazin-1-yl)-5-(trifluoromethyl)benzylidene)thiazolidine-2,4-dione hydrochloride | 12.69 (s, 1 H) 9.32 (brs, 2 H) 7.79 (d, 1 H) 7.71 (d, 2 H) 7.37 (d, 1 H) 3.23 (s, 8 H) | 358 | (Z)-tert-butyl 4-(2-((2,4-dioxothiazolidin-5-ylidene)methyl)-4-(trifluoromethyl)phenyl)piperazine-1-carboxylate Method 35 |

-continued

| Ex. | Compound | ¹H NMR | m/z | SM |
|---|---|---|---|---|
| 88 | (S,Z)-5-(2-(3-aminopyrrolidin-1-yl)-5-(trifluoromethyl)benzylidene)thiazolidine-2,4-dione hydrochloride | 12.53 (s, 1 H) 8.17 (brs, 2 H) 7.95 (s, 1 H) 7.65 (s, 1 H) 7.59 (d, 1 H) 7.05 (d, 1 H) 3.90-3.81 (m, 1 H) 3.56 (q, 1 H) 3.47-3.35 (m, 2 H) 3.18 (dd, 1 H) 2.33-2.18 (m, 1 H) 2.09-1.99 (m, 1 H) | 358 | (S,Z)-tert-butyl 1-(2-((2,4-dioxothiazolidin-5-ylidene)methyl)-4-(trifluoromethyl)phenyl)pyrrolidin-3-ylcarbamate Method 36 |
| 89 | (Z)-5-(2-(piperazin-1-yl)pyridin-3-ylmethylene)thiazolidine-2,4-dione hydrochloride | 12.65 (s, 1 H) 8.39 (s, 1 H) 8.33 (d, 1 H) 7.83 (d, 1 H) 7.63 (s, 1 H) 7.15 (dd, 1 H) 3.41 (brs, 4 H) 3.17 (brs, 4 H) | 291 | (Z)-tert-butyl 4-(3-((2,4-dioxothiazolidin-5-ylidene)methyl)pyridin-2-yl)piperazine-1-carboxylate Method 37 |

-continued

| Ex. | Compound | ¹H NMR | m/z | SM |
|---|---|---|---|---|
| 90 | (Z)-5-((2-(4-(3-aminopropanoyl)piperazin-1-yl)pyridin-3-yl)methylene)thiazolidine-2,4-dione trifluoroacetate | 12.60 (s, 1 H) 8.32 (d, 1 H) 7.82 (s, 1 H) 7.68 (s, 1 H) 7.63 (brs, 2 H) 7.12 (dd, 1 H) 3.57 (d, 4 H) 3.17 (d, 4 H) 3.00 (q, 2 H) 2.70 (t, 2 H) | 362 | (Z)-tert-butyl 3-(4-(3-((2,4-dioxothiazolidin-5-ylidene)methyl)pyridin-2-yl)piperazin-1-yl)-3-oxopropylcarbamate Method 38 |
| 91 | (Z)-5-(2-(4-(piperidine-4-carbonyl)piperazin-1-yl)benzylidene)thiazolidine-2,4-dione | 9.00 (brs, 1 H) 8.67 (brs, 1 H) 8.18 (s, 1 H) 7.57-7.52 (m, 1 H) 7.30-7.16 (m, 1 H) 3.71 (s, 1 H) 3.63 (s, 1 H) 3.34 (s, 3 H) 3.31-3.22 (m, 2 H) 3.13 (s, 3 H) 3.01-2.87 (m, 5 H) 1.85-1.77 (m, 4 H) | 401 | (Z)-tert-butyl 4-(4-(2-((2,4-dioxothiazolidin-5-ylidene)methyl)phenyl)piperazine-1-carbonyl)piperidine-1-carboxylate Method 39 |

| Ex. | Compound | 1H NMR | m/z | SM |
|---|---|---|---|---|
| 92 | (Z)-5-(2-(4-(piperidine-3-carbonyl)piperazin-1-yl)-5-(trifluoromethyl)benzylidene)thiazolidine-2,4-dione hydrochloride | 12.68 (s, 1 H) 8.87 (s, 1 H) 7.78-7.69 (m, 3 H) 7.32 (d, 1 H) 3.68-3.64 (m, 8 H) 3.38 (tt, 1 H) 3.13-2.98 (m, 4 H) 1.75-1.56 (m, 4 H) | 469 | (Z)-tert-butyl 3-(4-(2-((2,4-dioxothiazolidin-5-ylidene)methyl)-4-(trifluoromethyl)phenyl)piperazine-1-carbonyl)piperidine-1-carboxylate Method 40 |
| 93 | (Z)-5-(2-(4-(3-aminopropanoyl)piperazin-1-yl)-5-(trifluoromethyl)benzylidene)thiazolidine-2,4-dione | 12.67 (s, 1 H) 7.93 (brs, 2 H) 7.78-7.68 (m, 3 H) 7.32 (d, 1 H) 3.69-3.59 (m, 8 H) 3.00-2.74 (m, 4 H) | 429 | (Z)-tert-butyl 3-(4-(2-((2,4-dioxothiazolidin-5-ylidene)methyl)-4-(trifluoromethyl)phenyl)piperazin-1-yl)-3-oxopropylcarbamate Method 41 |

| Ex. | Compound | 1H NMR | m/z | SM |
|---|---|---|---|---|
| 94 | (Z)-5-(2-(4-(3-aminopropanoyl)piperazin-1-yl)-3-methoxybenzylidene)thiazolidine-2,4-dione hydrochloride 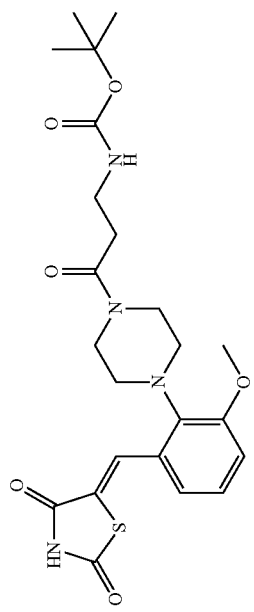 | 12.53 (brs, 1 H) 8.21 (s, 1 H), 7.58 (brs, 3 H) 7.24 (t, 1 H) 7.11 (d, 1 H) 7.00 (d, 1 H) 3.75 (s, 3 H) 3.35 (brs, 4 H) 3.09-2.85 (m, 4 H) 2.65 (brs, 2 H) | 391 | (Z)-tert-butyl 3-(4-(2-(2,4-dioxothiazolidin-5-ylidene)methyl)-6-methoxyphenyl)piperazin-1-yl)-3-oxopropylcarbamate Method 42 |
| 95 | (Z)-5-(2-(4-(3-aminopropanoyl)piperazin-1-yl)-3-chlorobenzylidene)thiazolidine-2,4-dione hydrochloride 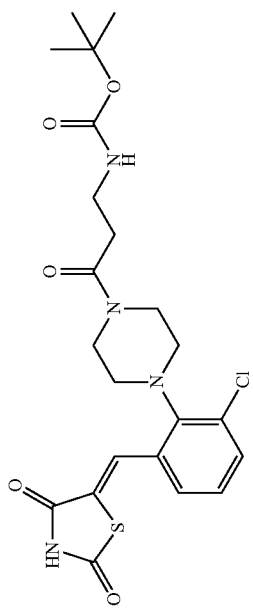 | 12.69 (brs, 1 H) 8.12 (s, 1 H) 7.67 (brs, 2 H) 7.55 (dd, 1 H) 7.49-7.40 (m, 1 H) 7.35 (t, 1 H) 4.17 (brs, 1 H) 3.75 (brs, 3 H) 3.13-3.35 (brs, 3 H) 2.84 (m, 5 H) 2.74 (brs, 2 H) | 395 | (Z)-tert-butyl 3-(4-(2-chloro-6-((2,4-dioxothiazolidin-5-ylidene)methyl)phenyl)piperazin-1-yl)-3-oxopropylcarbamate Method 43 |

| Ex. | Compound | ¹H NMR | m/z | SM |
|---|---|---|---|---|
| 96 | (S,Z)-5-(2-(3-aminopyrrolidin-1-yl)-3-methoxybenzylidene)thiazolidine-2,4-dione hydrochloride | 12.43 (s, 1 H) 7.94 (s, 1 H) 7.86 (brs, 1 H) 7.16 (t, 1 H) 7.05 (d, 1 H) 6.91 (d, 1 H) 3.71 (s, 3 H) 3.30 (dd, 1 H) 3.17-3.08 (m, 1 H) 3.08-2.91 (m, 2 H) 2.23-2.06 (m, 2 H), 1.80-1.75 (m, 1 H) | 320 | (S,X)-tert-butyl 1-(2-((2,4-dioxothiazolidin-5-ylidene)methyl)-6-methoxyphenyl)pyrrolidin-3-ylcarbamate Method 44 |
| 97 | (Z)-5-(3-methoxy-2-(piperazin-1-yl)benzylidene)thiazolidine-2,4-dione hydrochloride | 12.45 (brs, 1 H) 8.59 (brs, 1 H) 7.99 (s, 1 H) 7.15 (t, 1 H) 7.02 (d, 1 H) 6.89 (d, 1 H) 3.67 (s, 3 H) 3.17-2.99 (m, 8 H) | 320 | (Z)-tert-butyl 4-(2-((2,4-dioxothiazolidin-5-ylidene)methyl)-6-methoxyphenyl)piperazine-1-carboxylate Method 45 |

| Ex. | Compound | ¹H NMR | m/z | SM |
|---|---|---|---|---|
| 98 | (Z)-5-(3-chloro-2-(piperazin-1-yl)benzylidene)thiazolidine-2,4-dione hydrochloride | 12.72 (brs, 1 H) 9.19 (brs, 1 H) 8.01 (s, 1 H) 7.57 (dd, 1 H) 7.50-7.40 (m, 1 H) 7.36 (t, 1 H) 3.60 (brs, 2 H), 3.51-3.29 (m, 1 H) 3.29-3.12 (m, 2 H) 3.06 (brs, 3 H) | 324 | (Z)-tert-butyl 4-(2-chloro-6-((2,4-dioxothiazolidin-5-ylidene)methyl)phenyl)piperazine-1-carboxylate Method 46 |
| 99 | (Z)-5-(2-(3-(aminomethyl)pyrrolidin-1-yl)-4,5-dimethoxybenzylidene)thiazolidine-2,4-dione hydrochloride | 12.40 (s, 1 H) 9.25 (s, 1 H) 7.88 (s, 1 H) 6.97 (s, 1 H) 6.73 (s, 1 H) 3.85 (s, 3 H) 3.74 (s, 3 H) 3.81 (m, 1 H) 3.40-3.31 (m, 2 H) 3.25-3.13 (m, 2 H) 2.59 (t, 3 H) 2.31 (dd, 1 H) 2.08 (d, 1 H) | 364 | (Z)-tert-butyl (1-(2-((2,4-dioxothiazolidin-5-ylidene)methyl)-4,5-dimethoxyphenyl)pyrrolidin-3-yl)methylcarbamate Method 47 |

| Ex. | Compound | ¹H NMR | m/z | SM |
|---|---|---|---|---|
| 100 | (R,Z)-5-(2-(3-aminopyrrolidin-1-yl)-4,5-dimethoxybenzylidene)thiazolidine-2,4-dione hydrochloride | 12.39 (s, 1 H) 8.06 (s, 2 H) 7.89 (s, 1 H) 6.65 (s, 1 H) 3.84 (s, 4 H) 3.73 (s, 3 H) 3.35 (d, 2 H) 3.20 (s, 1 H) 3.07 (d, 1 H) 2.28 (s, 1 H) 1.97 (s, 1 H) | 350 | (R,Z)-tert-butyl 1-(2-((2,4-dioxothiazolidin-5-ylidene)methyl)-4,5-dimethoxyphenyl)pyrrolidin-3-ylcarbamate Method 48 |
| 101 | (S,Z)-5-(2-(3-aminopyrrolidin-1-yl)-4,5-dimethoxybenzylidene)thiazolidine-2,4-dione hydrochloride | 12.39 (s, 1 H) 8.08 (s, 2 H) 7.89 (s, 1 H) 6.65 (s, 1 H) 3.84 (s, 4 H) 3.73 (s, 3 H) 3.45-3.30 (m, 2 H) 3.24-3.14 (m, 1 H) 3.12-3.00 (m, 1 H) 2.28 (s,1 H) 1.98 (s, 1 H) | 350 | (S,Z)-tert-butyl 1-(2-((2,4-dioxothiazolidin-5-ylidene)methyl)-4,5-dimethoxyphenyl)pyrrolidin-3-ylcarbamate Method 49 |

| Ex. | Compound | ¹H NMR | m/z | SM |
|---|---|---|---|---|
| 102 | (Z)-5-(2-(4-(piperidine-3-carbonyl)-1,4-diazepan-1-yl)benzylidene)thiazolidine-2,4-dione hydrochloride | 12.49 (s, 1 H) 8.47 (s, 1 H) 7.82 (d, 1 H) 7.39-7.30 (m, 2 H) 7.16 (dd, 1 H) 7.06 (td, 1 H) 3.63-3.54 (m, 4 H) 3.29-3.06 (m, 9 H) 1.88-1.48 (m, 6 H) | 415 | (Z)-tert-butyl 3-(4-(2-((2,4-dioxothiazolidin-5-ylidene)methyl)phenyl)-1,4-diazepane-1-carbonyl)piperidine-1-carboxylate Method 50 |
| 103 | (Z)-5-(2-(4-(5-aminopentanoyl)-1,4-diazepan-1-yl)benzylidene)thiazolidine-2,4-dione hydrochloride | 12.57 (s, 1 H) 7.90 (d, 1 H) 7.76 (s, 2 H) 7.47-7.36 (m, 2 H) 7.22 (t, 1 H) 7.12 (d, 1 H) 3.63 (d, 4 H) 3.22 (s, 1 H) 3.17 (s, 1 H) 3.05 (s, 2 H) 2.80 (s, 2 H) 2.41 (s, 1 H) 2.34 (s, 1 H) 1.91 (s, 1 H) 1.85 (s, 1 H) 1.57 (d, 4 H) | 403 | (Z)-tert-butyl 5-(4-(2-((2,4-dioxothiazolidin-5-ylidene)methyl)phenyl)-1,4-diazepan-1-yl)-5-oxopentylcarbamate Method 51 |

| Ex. | Compound | ¹H NMR | m/z | SM |
|---|---|---|---|---|
| 104 | (Z)-5-(2-(4-(4-aminobutanoyl)-1,4-diazepan-1-yl)benzylidene)thiazolidine-2,4-dione hydrochloride | 12.49 (s, 1 H) 7.83 (d, 1 H) 7.65 (s, 2 H) 7.39-7.30 (m, 2 H) 7.20-7.12 (m, 1 H) 7.09-7.01 (m, 1 H) 3.61-3.50 (m, 4 H) 3.18-3.07 (m, 2 H) 2.98 (d, 2 H) 2.77 (ddd, 2 H) 2.37 (t, 2 H) 1.85-1.66 (m, 4 H). | 389 | (Z)-tert-butyl 4-(4-(2-((2,4-dioxothiazolidin-5-ylidene)methyl)phenyl)-1,4-diazepan-1-yl)-4-oxobutyl)carbamate Method 52 |
| 105 | (Z)-5-(2-(4-(3-aminopropanoyl)-1,4-diazepan-1-yl)benzylidene)thiazolidine-2,4-dione hydrochloride | 12.50 (s, 1 H) 7.83 (s, 1 H) 7.63 (s, 2 H) 7.31 (m, 2 H) 7.16 (dd, 1 H) 7.10-7.01 (m, 1 H) 3.64-3.52 (m, 4 H) 3.20-3.09 (m, 2 H) 2.97 (dt, 4 H) 2.65 (dt, 2 H) 1.87-1.81 (m, 2 H) | 375 | (Z)-tert-butyl 3-(4-(2-((2,4-dioxothiazolidin-5-ylidene)methyl)phenyl)-1,4-diazepan-1-yl)-3-oxopropyl)carbamate Method 53 |

| Ex. | Compound | ¹H NMR | m/z | SM |
|---|---|---|---|---|
| 106 | (Z)-5-(2-(1,4-diazepan-1-yl)benzylidene)thiazolidine-2,4-dione hydrochloride | 12.57 (s, 1 H) 9.31 (s, 1 H) 7.91 (s, 1 H) 7.46-7.40 (m, 2 H) 7.26 (d, 1 H) 7.18-7.09 (m, 1 H) 3.36 (d, 2 H) 3.27 (d, 4 H) 3.19 (dd, 2 H) 2.10-2.01 (m, 2 H) | 304 | (Z)-tert-butyl 4-(2-((2,4-dioxothiazolidin-5-ylidene)methyl)phenyl)-1,4-diazepane-1-carboxylate Method 54 |
| 107 | (Z)-5-(2-(4-(4-aminobutanoyl)piperazin-1-yl)benzylidene)thiazolidine-2,4-dione hydrochloride | 12.60 (s, 1 H) 7.95 (s, 4 H) 7.53-7.44 (m, 2 H) 7.26-7.17 (m, 2 H) 3.66-3.57 (m, 5 H) 2.89 (m, 4 H) 2.85-2.76 (m, 3 H) 1.85-1.76 (m, 2 H) | 375 | (Z)-tert-butyl 4-(4-(4-(2-((2,4-dioxothiazolidin-5-ylidene)methyl)phenyl)piperazin-1-yl)-4-oxobutyl)carbamate Method 55 |

| Ex. | Compound | ¹H NMR | m/z | SM |
|---|---|---|---|---|
| 108 | (Z)-5-(2-(4-(5-aminopentanoyl)piperazin-1-yl)benzylidene)thiazolidine-2,4-dione hydrochloride | 12.66 (s, 1 H) 8.10 (s, 2 H) 7.99 (s, 1 H) 7.52 (s, 1 H) 7.51-7.47 (m, 1 H) 7.25 (t, 2 H) 3.67 (s, 4 H) 2.92-2.81 (m, 6 H) 2.44 (t, 2 H) 1.62 (s, 4 H) | 389 | (Z)-tert-butyl 5-(4-(2-((2,4-dioxothiazolidin-5-ylidene)methyl)phenyl)piperazin-1-yl)-5-oxopentylcarbamate Method 56 |
| 109 | (Z)-5-(2-(4-(4-(piperazin-1-ylmethyl)benzoyl)piperazin-1-yl)benzylidene)thiazolidine-2,4-dione hydrochloride | 12.57 (brs, 1 H) 9.70 (brs, 1 H) 7.94 (s, 1 H) 7.75 (d, 2 H) 7.52 (m, 2 H) 7.49-7.41 (m, 2 H) 7.21 (t, 2 H) 4.45 (brs, 2 H) 3.81 (brs, 2 H) 3.54-3.35 (m, 8 H) 3.27 (brs, 2 H) 2.89 (brs, 4 H) | 492 | (Z)-tert-butyl 4-(4-(4-(2-((2,4-dioxothiazolidin-5-ylidene)methyl)phenyl)piperazine-1-carbonyl)benzyl)piperazine-1-carboxylate Method 57 |

| Ex. | Compound | ¹H NMR | m/z | SM |
|---|---|---|---|---|
| 110 | (Z)-5-(2-(4-(3-(aminomethyl)benzoyl)piperazin-1-yl)benzylidene)thiazolidine-2,4-dione hydrochloride | 12.56 (s, 1 H) 8.18 (brs, 2 H) 7.95 (s, 1 H) 7.64-7.38 (m, 6 H) 7.36-7.11 (m, 2H) 4.19-4.02 (m, 2H) 3.82 (brs, 2 H) 3.52 (brs, 2 H) 2.92 (brs, 4 H) | 423 | (Z)-tert-butyl 3-(4-(2-((2,4-dioxothiazolidin-5-ylidene)methyl)phenyl)piperazine-1-carbonyl)benzylcarbamate Method 58 |
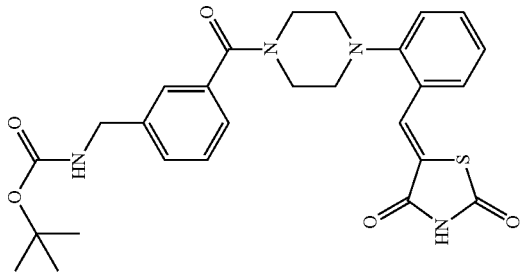

| Ex. | Compound | 1H NMR | m/z | SM |
|---|---|---|---|---|
| 111 | (Z)-5-(2-(3-(2-aminoethylamino)pyrrolidin-1-yl)-4,5-dimethoxybenzylidene)thiazolidine-2,4-dione hydrochloride | 12.38 (s, 1 H) 9.99 (s, 1 H) 8.44 (s, 2 H) 7.86 (s, 1 H) 6.96 (s,1H) 6.76 (s, 1 H) 3.93 (s, 1 H) 3.84 (s, 3 H) 3.73 (s, 3 H) 3.45-3.33 (m, 2 H) 3.28-3.16 (m, 6 H) 2.32 (s, 1 H) 2.15 (s,1 H) | 393 | (Z)-tert-butyl 2-(1-(2-((2,4-dioxothiazolidin-5-ylidene)methyl)-4,5-dimethoxyphenyl)pyrrolidin-3-ylamino)ethylcarbamate Method 59 |

| Ex. | Compound | ¹H NMR | m/z | SM |
|---|---|---|---|---|
| 112 | (Z)-5-(2-(4-(2-aminoethyl)piperazin-1-yl)benzylidine)thiazolidine-2,4-dione hydrochloride | 12.70 (s, 1 H) 11.43 (s, 1 H) 8.38 (s, 3 H) 7.86 (s, 1 H) 7.49 (m, 2 H) 7.25 (m, 2 H) 3.67 (m, 2 H) 3.42-3.30 (m, 8 H) | 333 | (Z)-tert-butyl 2-(4-(2-((2,4-dioxothiazolidin-5-ylidene)methyl)phenyl)piperazin-1-yl)ethylcarbamate Method 60 |

-continued
| Ex. | Compound | ¹H NMR | m/z | SM |
|---|---|---|---|---|
| 113 | (Z)-5-(4,5-dimethoxy-2-(3-(2-(methylamino)ethylamino)pyrrolidin-1-yl)benzylidene)thiazolidine-2,4-dione hydrochloride | 12.39 (s, 1 H) 9.93 (brs, 1 H) 9.42 (brs, 1 H) 7.87 (s, 1 H) 6.98 (s, 1 H) 6.77 (s, 1 H) 4.00-3.91 (m, 1 H) 3.85 (s, 3 H) 3.74 (s, 3 H) 3.44-3.16 (m, 8 H) 2.62 (s, 3 H) 2.40-2.31 (m, 1 H) 2.20-2.14 (m, 1 H) | 407 | (Z)-tert-butyl 2-(1-(2-((2,4-dioxothiazolidin-5-ylidene)methyl)-4,5-dimethoxyphenyl)pyrrolidin-3-ylamino)ethyl(methyl)carbamate Method 61 |
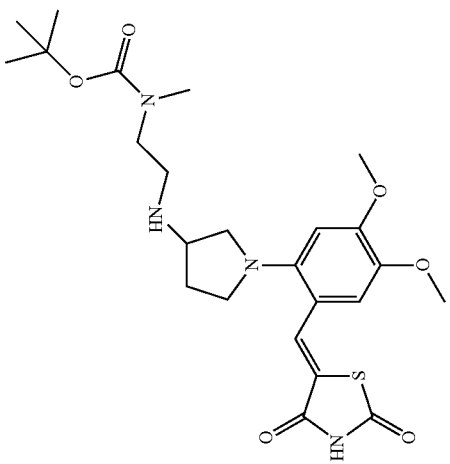

| Ex. | Compound | ¹H NMR | m/z | SM |
|---|---|---|---|---|
| 114 | (Z)-5-(2-(4-(2-(methylamino)ethyl)piperazin-1-yl)benzylidene)thiazolidine-2,4-dione hydrochloride | 12.62 (s, 1 H) 11.28 (s, 1 H) 9.28 (s, 1 H) 7.87 (s, 1 H) 7.50 (t, 1 H) 7.26 (t, 1 H) 3.71 (m, 4 H) 3.57 (m, 2 H) 3.45 (m, 2 H) 3.26 (m, 4 H) 2.62 (s, 3 H) | 347 | (Z)-tert-butyl 2-(4-(2-((2,4-dioxothiazolidin-5-ylidene)methyl)phenyl)piperazin-1-yl)ethyl(methyl)carbamate Method 62 |
| 115 | (5Z)-5-(2-piperazin-1-ylbenzylidene)-1,3-thiazolidine-2,4-dione hydrochloride | 12.61 (s, 1 H) 9.21 (s, 1 H) 7.86 (s, 1 H) 7.49 (t, 2 H) 7.24 (t, 2 H) 3.25 (s, 4 H) 3.12 (s, 4 H) | 290 | tert-butyl-4-{2-[(Z)-(2,4-dioxo-1,3-thiazolidin-5-ylidene)methyl]phenyl}piperazine-1-carboxylate Example 58 |

| Ex. | Compound | ¹H NMR | m/z | SM |
|---|---|---|---|---|
| 116 | 5-(2-(4-(piperidine-3-carbonyl)piperazin-1-yl)benzylidene)thiazolidine-2,4-dione hydrochloride | 12.60 (s, 1 H) 9.10 (s, 1 H) 8.90 (s, 1 H) 7.94 (s, 1 H) 7.51-7.43 (m, 1 H) 7.21 (t,2 H) 5.14 (m, 4 H) 3.67 (m, 3 H) 3.17 (m, 2 H) 2.91-2.88 (m, 4 H) 1.86 (s, 1H) 1.81-1.71 (m, 2 H) 1.57 (d, 1 H) | 401 | tert-butyl 3-(4-(2-((2,4-dioxothiazolidin-5-ylidene)methyl)phenyl)piperazine-1-carbonyl)piperidine-1-carboxylate Method 63 |
| 117 | (5Z)-5-{2-[4-(azetidin-3-ylcarbonyl)piperazin-1-yl]benzylidene}-1,3-thiazolidine-2,4-dione hydrochloride | 12.59 (s, 1 H) 9.15 (s, 1 H) 8.86 (s, 1 H) 7.93 (s, 1 H) 7.47 (ddd, 2 H) 7.25-7.16 (m, 4 H) 4.15-4.05 (m, 4 H) 4.01-3.91 (m, 1 H) 3.71 (m, 2 H) 3.42 (s, 2 H) 2.89 (d, 4 H) | 373 | tert-butyl 3-(4-(2-((2,4-dioxothiazolidin-5-ylidene)methyl)phenyl)piperazine-1-carbonyl)azetidine-1-carboxylate Method 64 |

| Ex. | Compound | ¹H NMR | m/z | SM |
|---|---|---|---|---|
| 118 | (5Z)-5-[2-(3-aminopyrrolidin-1-yl)-4,5-dimethoxybenzylidene]-1,3-thiazolidine-2,4-dione hydrochloride | 12.38 (s, 1 H) 8.34 (s, 2 H) 7.90 (s, 1 H) 6.96 (s, 1 H) 6.68 (s, 1 H) 3.89-3.80 (m, 4 H) 3.73 (s, 3 H) 3.46-3.34 (m, 2 H) 3.23-3.13 (m, 1 H) 3.10 (dd, 1 H) 2.28 (dd, 1 H) 2.01 (d, 1 H) | 351 | tert-butyl 1-(2-((2,4-dioxothiazolidin-5-ylidene)methyl)-4,5-dimethoxyphenyl)pyrrolidin-3-ylcarbamate Method 65 |
| 119 | (R,Z)-5-amino-N-(1-(2-((2,4-dioxothiazolidin-5-ylidene)methyl)-4,5-dimethoxyphenyl)pyrrolidin-3-yl)pentanamide hydrochloride | 12.24 (s, 1 H) 8.07 (d, 1 H) 7.79 (s, 1 H) 7.60 (brs, 2 H) 6.88 (s, 1 H) 6.55 (s, 1 H) 4.22 (d, 1 H) 3.76 (s, 3 H) 3.65 (s, 3 H) 3.30-3.15 (m, 2 H) 3.15-2.98 (m, 1 H) 2.86 (dd, 1 H) 2.70 (d, 2 H) 2.17-1.92 (m, 3 H) 1.76 (brs, 1 H) 1.52-1.25 (m, 4 H) | 449 | (R,Z)-tert-butyl 5-(1-(2-((2,4-dioxothiazolidin-5-ylidene)methyl)-4,5-dimethoxyphenyl)pyrrolidin-3-ylamino)-5-oxopentylcarbamate Method 66 |

| Ex. | Compound | ¹H NMR | m/z | SM |
|---|---|---|---|---|
| 120 | (S,Z)-5-amino-N-(1-(2-((2,4-dioxothiazolidin-5-ylidene)methyl)-4,5-dimethoxyphenyl)pyrrolidin-3-yl)pentanamide hydrochloride | 12.24 (s, 1 H) 8.07 (d, 1 H) 7.79 (s, 1 H) 7.60 (brs, 2 H) 6.88 (s, 1 H) 6.55 (s, 1 H) 4.22 (d, 1 H) 3.76 (s, 3 H) 3.65 (s, 3 H) 3.30-3.15 (m, 2 H) 3.15-2.98 (m, 1 H) 2.86 (dd, 1 H) 2.70 (d, 2 H) 2.17-1.92 (m, 3 H) 1.76 (brs, 1 H) 1.52-1.25 (m, 4H) | 449 | (S,Z)-tert-butyl 5-(1-(2-((2,4-dioxothiazolidin-5-ylidene)methyl)-4,5-dimethoxyphenyl)pyrrolidin-4-ylamino)-5-oxopentylcarbamate Method 67 |

-continued
| Ex. | Compound | 1H NMR | m/z | SM |
|---|---|---|---|---|
| 121 | (S,Z)-5-(2-(3-(3-aminopropylamino)pyrrolidin-1-yl)-4,5-dimethoxybenzylidene)thiazolidine-2,4-dione hydrochloride | 12.50 (s, 1 H) 9.78 (s, 1 H) 7.92 (s, 1 H) 7.05 (s, 1 H) 6.85 (s, 1 H) 4.21–4.11 (m, 1 H) 3.93 (s, 3 H) 3.83 (s, 3 H) 3.42–3.25 (m, 8 H) 2.45 (m, 1 H) 2.20 (m, 1 H) 1.32 (m, 2 H) | 407 | (S,Z)-tert-butyl 3-(1-(2-((2,4-dioxothiazolidin-5-ylidene)methyl)-4,5-dimethoxyphenyl)pyrrolidin-3-ylamino)propylcarbamate Method 68 |
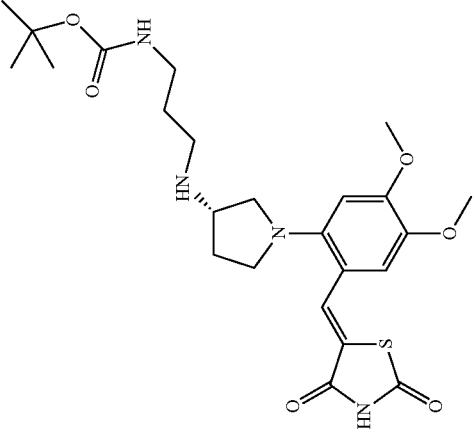

-continued

| Ex. | Compound | ¹H NMR | m/z | SM |
|---|---|---|---|---|
| 122A | (R,Z)-5-(2-(3-(3-aminopropylamino)pyrrolidin-1-yl)-4,5-dimethoxybenzylidene)thiazolidine-2,4-dione hydrochloride | 12.44 (s, 1 H) 9.78 (s, 1 H) 7.92 (s, 1 H) 7.05 (s, 1 H) 6.85 (s, 1 H) 4.21-4.11 (m, 1 H) 3.93 (s, 3 H) 3.83 (s, 3 H) 3.42-3.25 (m, 8 H) 2.45 (m, 1 H) 2.20 (m, 1 H) 1.32 (m, 2 H) | 407 | (R,Z)-tert-butyl 3-(1-(2-((2,4-dioxothiazolidin-5-ylidene)methyl)-4,5-dimethoxyphenyl)pyrrolidin-3-ylamino)propylcarbamate Method 69 |
| 122B | (R,Z)-5-(2-(3-(aminomethyl)pyrrolidin-1-yl)-3-chlorobenzylidene)thiazolidine-2,4-dione | (400 MHz, MeOD) ppm 8.08 (s, 1 H) 7.49 (dd, 2 H) 7.31 (t, 1 H) 3.56 (t, 1 H) 3.42-3.51 (m, 1 H) 3.38 (td, 1 H) 3.09-3.15 (m, 2 H) 2.71-2.78 (m, 1 H) 2.26-2.36 (m, 1 H) 1.86-1.96 (m, 1 H) 1.31 (dd, 1 H) | 338 | (R,Z)-tert-butyl (1-(2-chloro-6-((2,4-dioxothiazolidin-5-ylidene)methyl)phenyl)pyrrolidin-3-yl)methylcarbamate Method 132 |

| Ex. | Compound | ¹H NMR | m/z | SM |
|---|---|---|---|---|
| 122C | (S,Z)-5-(2-(3-(aminomethyl)pyrrolidin-1-yl)-3-chlorobenzylidene)thiazolidin-2,4-dione | (400 MHz, MeOD) ppm 8.07 (s, 1 H) 7.49 (dd, 2 H) 7.31 (t, 1 H) 3.56 (t, 1 H) 3.42-3.51 (m, 2 H) 3.38 (td, 1 H) 3.07-3.16 (m, 2 H) 2.67-2.79 (m, 1 H) 2.24-2.36 (m, 1 H) 1.90 (dd, 1 H) | 338 | (S,Z)-tert-butyl (1-(2-chloro-6-((2,4-dioxothiazolidin-5-ylidene)methyl)phenyl)pyrrolidin-3-yl)methylcarbamate Method 133 |
| 122D | (R,Z)-5-(2-(3-aminopiperidin-1-yl)-3-chlorobenzylidene)thiazolidin-2,4-dione hydrochloride | 12.70 (s, 1 H) 8.17 (brs, 3 H) 8.01 (s, 1 H) 7.52 (d, 1 H) 7.41-7.31 (m, 2 H) 3.40-3.10 (m, 4 H) 2.84-2.81 (m, 1 H) 2.12-2.10 (m, 1 H) 1.80-1.58 (m, 3 H) | 338 | (R,Z)-tert-butyl 1-(2-chloro-6-((2,4-dioxothiazolidin-5-ylidene)methyl)phenyl)piperidin-3-ylcarbamate Method 134 |

| Ex. | Compound | ¹H NMR | m/z | SM |
|---|---|---|---|---|
| 122E | (R,Z)-5-(2-(3-aminopiperidin-1-yl)-3-methoxybenzylidene)thiazolidine-2,4-dione hydrochloride | 12.60 (s, 1 H) 8.12 (s, 4 H) 7.28-7.02 (m, 3 H) 3.82 (s, 3 H) 3.18-2.87 (m, 5 H) 2.10-2.07 (m, 1 H) 1.75-1.38 (m, 3 H) | 334 | (R,Z)-tert-butyl 1-(2-((2,4-dioxothiazolidin-5-ylidene)methyl)-6-methoxyphenyl)piperidin-3-ylcarbamate Method 135 |
| 122F | (R,Z)-5-(2-(3-aminopiperidin-1-yl)-3-bromobenzylidene)thiazolidine-2,4-dione hydrochloride | 12.70 (s, 1 H) 8.15 (brs, 3 H) 8.01 (s, 1 H) 7.74-7.69 (m, 1 H) 7.46 (d, 1 H) 7.26 (t, 1 H) 3.27-2.99 (m, 4 H) 2.82-2.80 (m, 1 H) 2.12-2.10 (m, 1 H) 1.76-1.40 (m, 3 H) | 383 | (R,Z)-tert-butyl 1-(2-bromo-6-((2,4-dioxothiazolidin-5-ylidene)methyl)phenyl)piperidin-3-ylcarbamate Method 136 |

| Ex. | Compound | ¹H NMR | m/z | SM |
|---|---|---|---|---|
| 122G | (R,Z)-5-(2-(3-aminopyrrolidin-1-yl)-3-chlorobenzylidene)thiazolidine-2,4-dione hydrochloride | 12.67 (brs, 1 H) 8.30 (brs, 3 H) 7.93 (s, 1 H) 7.55 (d, 1 H) 7.41-7.31 (m, 2 H) 3.87 (brs, 1 H) 3.50-3.27 (m, 4 H) 2.40-2.28 (m, 1 H) 2.08-1.95 (m, 1 H) | 324 | (R,Z)-tert-butyl 1-(2-chloro-6-((2,4-dioxothiazolidin-5-ylidene)methyl)phenyl)pyrrolidin-3-ylcarbamate Method 137 |
| 122H | (S,Z)-5-(2-(3-aminopyrrolidin-1-yl)-3-bromobenzylidene)thiazolidine-2,4-dione hydrochloride | 12.68 (brs, 1 H) 8.31 (brs, 3 H) 7.90 (s, 1 H) 7.75 (d, 1 H) 7.46 (d, 1 H) 7.29 (t, 1 H) 3.75 (brs, 1 H) 3.55 (t, 1 H) 3.38-3.25 (m, 3 H) 2.40-2.32 (m, 1 H) 2.12-2.02 (m, 1 H) | 370 | (S,Z)-tert-butyl 1-(2-bromo-6-((2,4-dioxothiazolidin-5-ylidene)methyl)phenyl)pyrrolidin-3-ylcarbamate Method 138 |

| Ex. | Compound | ¹H NMR | m/z | SM |
|---|---|---|---|---|
| 122I | (R,Z)-5-(2-(3-aminopiperidin-1-yl)-3-ethoxybenzylidene)thiazolidine-2,4-dione hydrochloride | 12.58 (s, 1 H) 8.13-8.09 (m, 4 H) 7.26-7.14 (m, 1 H) 7.16-7.14 (m, 1 H) 7.03-7.01 (m, 1 H) 4.07 (q, 2 H) 3.78-3.67 (m, 2 H) 3.22-3.07 (m, 3 H) 2.10-2.07 (m, 1 H) 1.76-1.55 (m, 3 H) 1.38 (t, 3 H) | 348 | (R,Z)-tert-butyl 1-(2-((2,4-dioxothiazolidin-5-ylidene)methyl)-6-ethoxyphenyl)piperidin-3-ylcarbamate Method 139 |
| 122J | (R,Z)-tert-butyl 1-(2-((2,4-dioxothiazolidin-5-ylidene)methyl)-6-isobutoxyphenyl)piperidin-3-ylcarbamate hydrochloride | 12.60 (s, 1 H) 8.18 (brs, 3 H) 8.15 (s,1H) 7.26 (t, 1 H) 7.15 (d, 1 H) 7.02 (d, 1 H) 3.84-3.74 (m, 2 H) 3.20-3.02 (m, 4 H) 2.74 (d, 1 H) 2.14-2.07 (m, 2 H) 1.73-1.21 (m, 3 H) 1.03 (d, 6 H) | 376 | (R,Z)-tert-butyl 1-(2-((2,4-dioxothiazolidin-5-ylidene)methyl)-6-isobutoxyphenyl)piperidin-3-ylcarbamate Method 140 |

| Ex. | Compound | ¹H NMR | m/z | SM |
|---|---|---|---|---|
| 122K | (R,Z)-5-(2-(3-aminopiperidin-1-yl)-3-(cyclohexylmethoxy)benzylidene)thiazolidine-2,4-dione hydrochloride | 12.60 (s, 1 H) 8.14 (brs, 4 H) 7.25 (t, 1 H) 7.14 (d, 1 H) 7.00 (d, 1 H) 3.82 (brs, 2 H) 3.29-3.00 (m, 4 H) 2.75-2.72 (m, 1 H) 2.12-2.10 (m, 1 H) 1.86-1.50 (m, 8 H) 1.35-1.03 (m, 6 H) | 416 | (R,Z)-tert-butyl 1-(2-(cyclohexylmethoxy)-6-((2,4-dioxothiazolidin-5-ylidene)methyl)phenyl)piperidin-3-ylcarbamate Method 141 |
| 122L | (R,Z)-5-(2-(3-aminopiperidin-1-yl)-3-(cyclohexyl)benzylidene)thiazolidine-2,4-dione hydrochloride | | 402 | (R,Z)-tert-butyl 1-(2-(cyclohexyl)-6-((2,4-dioxothiazolidin-5-ylidene)methyl)phenyl)piperidin-3-ylcarbamate Method 142 |

| Ex. | Compound | ¹H NMR | m/z | SM |
|---|---|---|---|---|
| 122M | (±)-(Z)-5-(2,3-amino-4-hydroxypiperidin-1-yl)-3-chlorobenzylidene)thiazolidine-2,4-dione hydrochloride | 12.68 (s, 1 H) 8.01 (brs, 4 H) 7.53 (d, 1 H) 7.44-7.42 (m, 1 H) 7.35 (t, 1 H) 5.72-5.70 (m, 1 H) 3.32-3.22 (m, 2 H) 3.20-3.11 (m, 3 H) 1.96-1.94 (m, 1 H) 1.40-1.37 (m, 1 H) | 354 | (±)-tert-butyl-1-(2-chloro-6-((Z)-(2,4-dioxothiazolidin-5-ylidene)methyl)phenyl)-4-hydroxypiperidin-3-ylcarbamate Method 143 |
| 122N | (Z)-5-(3-chloro-2-(1,4-diazepan-1-yl)benzylidene)thiazolidine-2,4-dione hydrochloride | 12.73 (brs, 1 H), 9.18 (brs, 2 H), 8.04 (s, 1 H), 7.62 (d, 1 H), 7.41 (dt, 2 H), 3.65 (brs, 1 H), 3.34-3.30 (m, 5 H), 3.04 (brs, 2 H), 2.14 (brs, 2 H) | 338 | (Z)-tert-butyl 4-(2-chloro-6-((Z)-(2,4-dioxothiazolidin-5-ylidene)methyl)phenyl)-1,4-diazepane-1-carboxylate Method 144 |

| Ex. | Compound | ¹H NMR | m/z | SM |
|---|---|---|---|---|
| 122O | (R,Z)-5-(2-(3-aminopiperidin-1-yl)-3-isopropoxybenzylidene)thiazolidine-2,4-dione hydrochloride | 12.61 (brs, 1 H) 8.33 (brs, 3 H) 8.15 (brs, 1 H) 7.34-7.09 (m, 2 H) 6.99 (d, 1 H) 4.67 (ddd 1 H) 3.28 (brs, 1 H) 3.07 (brs, 3 H) 2.70 (brs, 1 H) 2.12 (brs, 1 H) 1.73 (brs, 1 H) 1.57 (brs, 1 H) 1.51-1.21 (m, 7 H) | 362 | (R,Z)-tert-butyl 1-(2-((2,4-dioxothiazolidin-5-ylidene)methyl)-6-isopropoxyphenyl)piperidin-3-ylcarbamate Method 145 |
| 122P | (S,Z)-5-(2-(3-aminopyrrolidin-1-yl)-3-isopropoxybenzylidene)thiazolidine-2,4-dione hydrochloride | 12.58 (brs, 1 H) 8.52 (brs, 3 H) 8.08 (s, 1 H) 7.39-7.10 (m, 2 H) 6.99 (d, 1 H) 4.70 (d, 1 H) 3.78 (brs, 1 H) 3.52-3.33 (m, 1 H) 3.33-3.03 (m, 3 H) 2.28 (brs, 1 H) 2.00 (d, 1 H) 1.32 (d, 6 H) | 348 | (S,Z)-tert-butyl 1-(2-((2,4-dioxothiazolidin-5-ylidene)methyl)-6-isopropoxyphenyl)pyrrolidin-3-ylcarbamate Method 146 |

-continued

| Ex. | Compound | ¹H NMR | m/z | SM |
|---|---|---|---|---|
| 122Q | (S,Z)-5-(2-(3-aminopyrrolidin-1-yl)-3-ethoxybenzylidene)thiazolidine-2,4-dione hydrochloride | 12.58 (brs, 1 H) 8.48 (brs, 3 H) 8.09 (s, 1 H) 7.26 (t, 1 H) 7.16 (d, 1 H) 7.02 (d, 1 H) 4.09 (q, 2 H) 3.80 (d, 1 H) 3.47 (dd, 1 H) 3.28 (m, 1 H) 3.21 (dd, 1 H) 2.29 (d, 1 H) 2.01 (dd, 1 H) 1.40 (t, 3 H) | 334 | (S,Z)-tert-butyl 1-(2-((2,4-dioxothiazolidin-5-ylidene)methyl)-6-ethoxyphenyl)pyrrolidin-3-ylcarbamate Method 147 |
| 122R | (R,Z)-5-(2-(4-(aminomethyl)benzylamino)piperidin-1-yl)-3-chlorobenzylidene)thiazolidine-2,4-dione hydrochloride | 9.62 (brs, 1 H) 8.46 (brs, 3 H) 7.66-7.49 (m, 5 H) 7.47-7.34 (m, 2 H) 4.26-4.12 (m, 2 H) 4.09-3.94 (m, 2 H) 3.42-3.25 (m, 4 H) 2.83 (brs, 1 H) 2.36 (s, 1 H) 1.85 (m, 1 H) 1.62 (d, 2 H) | 457 | (R,Z)-tert-butyl 4-((1-(2-chloro-6-((2,4-dioxothiazolidin-5-ylidene)methyl)phenyl)piperidin-3-ylamino)methyl)benzylcarbamate Example 167 |

| Ex. | Compound | ¹H NMR | m/z | SM |
|---|---|---|---|---|
| 122S | (R,Z)-5-(3-chloro-2-(3-(2-(methylamino)ethylamino)piperidin-1-yl)benzylidene)thiazolidine-2,4-dione hydrochloride | 12.68 (brs, 1 H) 9.68 (brs, 2 H) 9.21 (brs, 2 H) 8.05 (s, 1 H) 7.56 (d, 1 H) 7.50-7.42 (m, 1 H) 7.37 (t, 1 H) 3.75-3.65 (m, 5 H) 3.63-3.57 (m, 2 H) 3.16 (d, 1 H) 2.82 (brs, 1 H) 2.60 (brs, 3 H) 2.37-2.28 (m, 1 H) 1.80 (d, 1 H) 1.65 (m, 1 H) 1.54 (brs, 1 H) | 395 | (R,Z)-tert-butyl 2-(1-(2-chloro-6-((2,4-dioxothiazolidin-5-ylidene)methyl)phenyl)piperidin-3-ylamino)ethyl(methyl)carbamate Example 168 |
| 122T | (Z)-5-(2-((3S,4S)-3-amino-4-hydroxypyrrolidin-1-yl)-3-chlorobenzylidene)thiazolidine-2,4-dione hydrochloride | 12.68 (brs, 1 H) 8.50 (brs, 3 H) 8.10-7.81 (m, 1 H) 7.58 (dd, 1 H) 7.51-7.27 (m, 2 H) 4.56-4.28 (m, 1 H) 3.84 (brs, 1 H) 3.66-3.40 (m, 4 H) 3.39-3.23 (m, 1 H) | 339 | tert-butyl (3S,4S)-1-(2-chloro-6-((Z)-(2,4-dioxothiazolidin-5-ylidene)methyl)phenyl)-4-hydroxypyrrolidin-3-ylcarbamate Method 151 |

-continued

| Ex. | Compound | ¹H NMR | m/z | SM |
|---|---|---|---|---|
| 122U | (Z)-5-(3-chloro-2-(4-methyl-3-(methylamino)piperidin-1-yl)benzylidene)thiazolidine-2,4-dione hydrochloride | 12.69 (brs, 1 H) 8.63 (brs, 2 H) 8.02 (s, 1 H) 7.57 (d, 1 H) 7.47-7.31 (m, 2 H) 3.58 (m, 1 H) 3.07 (m, 1 H) 2.67 (brs, 1 H) 2.58 (brs, 3 H) 2.40 (m, 1 H) 1.87 (m, 1 H) 1.68 (m, 1 H) 1.29 (m, 1 H) 1.07 (d, 3 H) 0.87 (d, 1 H) | 365 | (Z)-tert-butyl 1-(2-chloro-6-((2,4-dioxothiazolidin-5-ylidene)methyl)phenyl)-4-methylpiperidin-3-yl(methyl)carbamate Method 152 |
| 122V | (Z)-5-(2-(3-amino-4-mmethylpiperidin-1-yl)-3-chlorobenzylidene)thiazolidine-2,4-dione hydrochloride | | 351 | (Z)-tert-butyl 1-(2-chloro-6-((2,4-dioxothiaozlidin-5-ylidene)methyl)phenyl)-4-methylpiperidin-3-ylcarbamate Method 153 |

| Ex. | Compound | ¹H NMR | m/z | SM |
|---|---|---|---|---|
| 122W | (R,Z)-5-(2-(3-aminopiperidin-1-yl)benzylidene)thiazolidine-2,4-dione hydrochloride | 12.58 (s, 1 H) 8.44 (brs, 3 H) 7.89 (s, 1 H) 7.54-7.34 (m, 2 H) 7.27-7.05 (m, 2 H) 3.26 (d, 2 H) 2.94 (d, 1 H) 2.87-2.61 (m, 2 H) 2.05 (brs, 1 H) 1.85 (brs, 1 H) 1.75-1.47 (m, 2 H) | 304 | (R,Z)-tert-butyl 1-(2-((2,4-dioxothiazolidin-5-ylidene)methyl)phenyl)piperidin-3-ylcarbamate Method 154 |
| 122X | (S,Z)-5-(2-(3-aminopyrrolidin-1-yl)benzylidene)thiazolidine-2,4-dione hydrochloride | 12.49 (s, 1 H) 8.50 (brs, 3 H) 7.91 (s, 1 H) 7.44-7.22 (m, 2 H) 7.07-6.79 (m, 2 H) 3.83 (d, 1 H) 3.51-3.29 (m, 2 H) 3.28-3.17 (m, 2 H) 2.27 (dd, 1 H), 2.11-1.94 (m, 1 H) | 290 | (S,Z)-tert-butyl 1-(2-((2,4-dioxothiazolidin-5-ylidene)methyl)phenyl)pyrrolidin-3-ylcarbamate Method 155 |

| Ex. | Compound | ¹H NMR | m/z | SM |
|---|---|---|---|---|
| 122Y | (R,Z)-5-(2-(3-aminopiperidin-1-yl)-3-(2,2,2-trifluoroethoxy)benzylidene)thiazolidine-2,4-dione hydrochloride | 12.57 (brs, 1 H) 8.03 (brs, 1 H) 7.90 (brs, 3 H) 7.36-7.13 (m, 2 H) 7.07 (d, 1 H) 4.85-4.55 (m, 2 H) 2.98 (brs, 4 H) 2.74 (brs, 1 H) 2.02 (d, 1 H) 1.69 (d, 1 H) 1.54 (d, 1 H) 1.30 (brs, 1 H) | 402 | (R,Z)-tert-butyl 1-(2-((2,4-dioxothiazolidin-5-ylidene)methyl)-6-(2,2,2-trifluoroethoxy)phenyl)piperidin-3-ylcarbamate Method 156 |
| 122Z | (S,Z)-5-(2-(3-aminopyrrolidin-1-yl)-3-(2,2,2-trifluoroethoxy)benzylidene)thiazolidine-2,4-dione hydrochloride | 12.52 (brs, 1 H) 8.21-7.91 (m, 4 H) 7.34-7.14 (m, 2 H) 7.07 (d, 1 H) 4.88-4.72 (m, 2 H) 3.74 (d, 1 H) 3.40 (dd, 1 H) 3.22 (td, 1 H) 3.18-3.10 (m, 1 H) 3.06 (dd, 1 H) 2.30-2.10 (m, 1 H) 1.90 (dd, 1 H) | 388 | (S,Z)-tert-butyl 1-(2-((2,4-dioxothiazolidin-5-ylidene)methyl)-6-(2,2,2-trifluoroethoxy)phenyl)pyrrolidin-3-ylcarbamate Method 157 |

-continued

| Ex. | Compound | ¹H NMR | m/z | SM |
|---|---|---|---|---|
| 122AA | (R,Z)-5-(2-(3-aminopiperidin-1-yl)-3-(2-methoxyethoxy)benzylidene)thiazolidine-2,4-dione hydrochloride | 12.67 (brs, 1 H) 8.30 (brs, 3 H) 8.20 (brs, 1 H) 7.33 (brs, 1 H) 7.25 (brs, 1 H) 7.10 (d, 1 H) 4.68 (brs, 3 H) 4.22 (t, 2 H) 3.91-3.65 (m, 2 H) 3.42 (s, 3 H) 3.29 (brs, 1 H) 2.80 (brs, 1 H) 2.18 (brs, 1 H) 1.81 (brs, 1 H) 1.68 (brs, 1 H) 1.48 (brs, 1 H) | 378 | (R,Z)-tert-butyl 1-(2-((2,4-dioxothiazolidin-5-ylidene)methyl)-6-(2-methoxyethoxy)phenyl)piperidin-3-ylcarbamate Method 158 |
| 122AB | (S,Z)-5-(2-(3-aminopyrrolidin-1-yl)-3-(2-methoxyethoxy)benzylidene)thiazolidine-2,4-dione hydrochloride | 12.58 (brs, 1 H) 8.42 (brs, 3 H) 8.10 (s, 1 H) 7.28 (t, 1 H) 7.23-7.11 (m, 1 H) 7.04 (d, 1 H) 4.27-3.97 (m, 2 H) 3.85 (d, 1 H) 3.78-3.63 (m, 2 H) 3.49 (dd, 1 H) 3.34 (s, 3 H) 3.27 (td, 1 H) 3.22-3.06 (m, 2 H) 2.30 (dd, 1 H) 2.02 (dd, 1 H) | 364 | (S,Z)-tert-butyl 1-(2-((2,4-dioxothiazolidin-5-ylidene)methyl)-6-(2-methoxyethoxy)phenyl)pyrrolidin-3-ylcarbamate Method 159 |

-continued

| Ex. | Compound | ¹H NMR | m/z | SM |
|---|---|---|---|---|
| 122AC | (R,Z)-5-(2-(3-aminopiperidin-1-yl)-3-(cyclopentyloxy)benzylidene)thiazolidine-2,4-dione hydrochloride | 12.37 (brs, 1 H) 8.00 (brs, 3 H) 7.93 (s, 1 H) 7.02 (d, 1 H) 6.91 (d, 1 H) 6.77 (d, 1 H) 3.02-2.91 (m, 1 H) 2.82 (d, 3 H) 2.48 (brs, 1 H) 1.89-1.40 (m, 12 H) 1.16 (brs, 1 H) | 388 | (R,Z)-tert-butyl 1-(2-(cyclopentyloxy)-6-((2,4-dioxothiazolidin-5-ylidene)methyl)phenyl)piperidin-3-ylcarbamate Method 160 |
| 122AD | (R,Z)-5-(2-(3-aminopiperidin-1-yl)-3-cyclobutoxybenzylidene)thiazolidine-2,4-dione hydrochloride | 12.60 (brs, 1 H) 8.14 (brs, 4 H) 7.23 (t, 1 H) 7.00 (d, 2 H) 4.86-4.67 (m, 1 H) 3.25 (m, 1H) 3.05 (m, 2H) 2.74 (brs, 1 H) 2.49-2.35 (m, 2 H) 2.21-1.95 (m, 3 H) 1.93-1.76 (m, 2 H) 1.67 (td, 3 H) 1.42 (brs, 1 H) | 374 | (R,Z)-tert-butyl 1-(2-cyclobutoxy-6-((2,4-dioxothiazolidin-5-ylidene)methyl)phenyl)piperidin-3-ylcarbamate Method 161 |

-continued

| Ex. | Compound | ¹H NMR | m/z | SM |
|---|---|---|---|---|
| 122AE | (R,Z)-4-(3-aminopiperidin-1-yl)-3-((2,4-dioxothiazolidin-5-ylidene)methyl)benzamide hydrochloride | | 347 | (R,Z)-tert-butyl 1-(4-carbamoyl-2-((2,4-dioxothiazolidin-5-ylidene)methyl)phenyl)piperidin-3-ylcarbamate Method 162 |
| 122AF | (S,Z)-4-(3-aminopiperidin-1-yl)-3-((2,4-dioxothiazolidin-5-ylidene)methyl)benzamide hydrochloride | | 347 | (S,Z)-tert-butyl 1-(4-carbamoyl-2-((2,4-dioxothiazolidin-5-ylidene)methyl)phenyl)piperidin-3-ylcarbamate Method 163 |

| Ex. | Compound | ¹H NMR | m/z | SM |
|---|---|---|---|---|
| 122AG | (R,Z)-4-(3-aminopiperidin-1-yl)-3-((2,4-dioxothiazolidin-5-ylidene)methyl)benzoic acid hydrochloride | | 348 | (R,Z)-4-(3-(tert-butoxycarbonylamino)piperidin-1-yl)-3-((2,4-dioxothiazolidin-5-ylidene)methyl)benzoic acid Method 164 |
| 122AH | (S,Z)-4-(3-aminopyrrolidin-1-yl)-3-((2,4-dioxothiazolidin-5-ylidene)methyl)benzoic acid | | 333 | (S,Z)-4-(3-(tert-butoxycarbonylamino)pyrrolidin-1-yl)-3-((2,4-dioxothiaozlidin-5-ylidene)methyl)benzoic acid Method 165 |

| Ex. | Compound | ¹H NMR | m/z | SM |
|---|---|---|---|---|
| 122AI | (R,Z)-5-((2-(3-aminopiperidin-1-yl)biphenyl-3-yl)methylene)thiaozlidine-2,4-dione | 12.64 (brs, 1 H) 8.09 (brs, 3 H) 7.92 (s, 1 H) 7.56-7.36 (m, 4 H) 7.36-7.16 (m, 4 H) 3.06 (brs, 1 H) 3.00 (brs, 1 H) 2.72 (d, 1 H) 2.35 (brs, 2 H) 2.05 (brs, 1 H) 1.58 (brs, 2 H) 1.32-1.15 (m, 1 H) | 380 | (R,Z)-tert-butyl 1-(3-((2,4-dioxothiazolidin-5-ylidene)methyl)biphenyl-2-yl)piperidin-3-ylcarbamate Method 166 |

Example 123

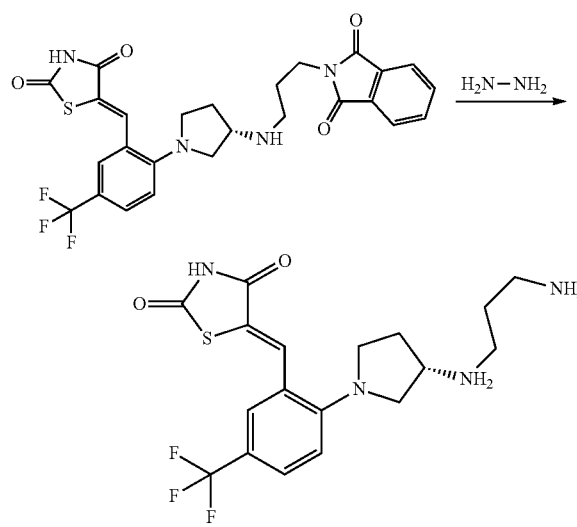

(S,Z)-5-(2-(3-(3-aminopropylamino)pyrrolidin-1-yl)-5-(trifluoromethyl)benzylidene)thiazolidine-2,4-dione hydrochloride A 25 mL round bottom flask was charged with a magnetic stir bar, (S,Z)-5-(2-(3-(3-(1,3-dioxoisoindolin-2-yl)propylamino)pyrrolidin-1-yl)-5-(trifluoromethyl)benzylidene)thiazolidine-2,4-dione (Method 70) (0.271 g, 0.50 mmol), EtOH (2.488 ml), and hydrazine (0.023 ml, 0.75 mmol). The reaction was stirred at rt for 30 min and then filtered through a bed of Celite. The filtrate was conc. in vacuo and purified via reverse phase HPLC (MeCN/water) to afford fractions that were conc. in vacuo, suspended in methanol (~5 mL) and 1N HCl in diethyl ether (~2 mL) and conc. in vacuo to afford (S,Z)-5-(2-(3-(3-aminopropylamino)pyrrolidin-1-yl)-5-(trifluoromethyl)benzylidene)thiazolidine-2,4-dione hydrochloride (0.071 g, 29.3%). $^1$H NMR (300 MHz, DMSO-D6) δ ppm 12.52 (s, 1 H) 9.49 (s, 1 H) 8.08 (brs, 2 H) 7.93 (s, 1 H) 7.67 (s, 1 H) 7.61 (d, 1 H) 7.08 (d, 1 H) 3.88-3.81 (m, 1 H) 3.53-3.33 (m, 4 H) 3.08-3.05 (m, 2 H) 2.92-2.89 (m, 2 H) 2.33-2.19 (m, 2 H) 2.04-1.96 (m, 2 H); m/z 415.

The following examples were prepared by the procedure of Example 123, using the appropriate starting materials. The following parent compounds obtained after chromatography may be converted to their corresponding hydrochloride salt in a manner similar as described in example 123.

| Ex. | Compound | $^1$H NMR | m/z | SM |
|---|---|---|---|---|
| 124 | (S,Z)-5-(2-(3-(3-aminopropylamino)pyrrolidin-1-yl)-3-methoxybenzylidene)thiazolidine-2,4-dione hydrochloride | 12.59 (brs, 1 H) 9.30 (brs, 1 H) 8.09 (s, 1 H) 8.07 (brs, 1 H) 7.32 (t, 1 H) 7.21 (d, 1 H) 7.08 (d, 1 H) 3.87 (s, 3 H) 3.46-3.44 (m, 1 H) 3.39-3.25 (m, 2 H) 3.17-2.99 (m, 4 H) 2.96-2.91 (m 2 H) 2.08-1.99 (m, 2 H) | 377 | (S,Z)-5-(2-(3-(3-(1,3-dioxoisoindolin-2-yl)propylamino)pyrrolidin-1-yl)-3-methoxybenzylidene)thiazolidine-2,4-dione Method 71 |
| 125 | (S,Z)-5-(2-(3-(3-aminopropylamino)pyrrolidin-1-yl)-3-chlorobenzylidene)thiazolidine-2,4-dione hydrochloride | 12.72 (brs, 1 H) 9.50 (brs, 1 H) 8.10 (brs, 2 H) 7.96 (s, 1 H) 7.60 (d, 1 H) 7.46-7.39 (m 2 H) 3.95-3.91 (m, 1 H) 3.51-3.20 (m, 4 H) 2.99-2.92 (m, 2 H) 2.44-2.38 (m, 2 H) 2.21-2.11 (m, 2 H) 2.08-1.99 (m, 2 H) | 382 | (S,Z)-5-(3-chloro-2-(3-(3-(1,3-dioxoisoindolin-2-yl)propylamino)pyrrolidin-1-yl)benzylidene)thiazolidine-2,4-dione Method 72 |

-continued

| Ex. | Compound | ¹H NMR | m/z | SM |
|---|---|---|---|---|
| 126 | (Z)-5-(2-(3-(3-aminopropylamino)pyrrolidin-1-yl)-4,5-dimethoxybenzylidene)thiazolidine-2,4-dione | 12.40 (s, 1 H) 9.78 (s, 1 H) 7.92 (s, 1 H) 7.05 (s, 1 H) 6.85 (s, 1 H) 4.21-4.11 (m, 1 H) 3.93 (s, 3 H) 3.83 (s, 3 H) 3.42-3.25 (m, 8 H) 2.45 (m, 1 H) 2.20 (m, 1 H) 1.32 (m, 2 H) | 407 | (Z)-5-(2-(3-(3-(1,3-dioxothiazolidin-2-yl)propylamino)pyrrolidin-1-yl)-4,5-dimethoxybenzylidene)thiazolidine-2,4-dione Method 73 |
| 127 | (Z)-5-(2-(4-(3-aminopropyl)piperazin-1-yl)benzylidene)thiazolidine-2,4-dione hydrochloride | 12.64 (s, 1 H) 11.50 (s, 1 H) 8.27 (s, 1 H) 7.85 (s, 1 H) 7.49 (t, 2 H) 7.24 (t, 2 H) 3.55 (d, 2 H) 3.32-3.16 (m, 8 H) 2.93 (d, 2 H) 2.18-2.07 (m, 2 H) | 347 | (Z)-5-(2-(4-(3-(1,3-dioxoisoindolin-2-yl)propyl)piperazin-1-yl)benzylidene)thiazolidine-2,4-dione Method 74 |

-continued

| Ex. | Compound | $^1$H NMR | m/z | SM |
|---|---|---|---|---|
| 128 | (Z)-3-amino-N-(1-(2-((2,4-dioxothiazolidin-5-ylidene)methyl)-4,5-dimethoxyphenyl)pyrrolidin-3-yl)propanamide hydrochloride | 12.34 (s, 1 H) 8.46 (d, 1 H) 7.86 (s, 3 H) 6.95 (s, 1 H) 6.63 (s, 1 H) 4.36-4.26 (m, 1 H) 3.84 (s, 3 H) 3.72 (s, 3 H), 3.32-3.21 (m, 3 H) 3.02-2.93 (m, 3 H) 2.18 (dd, 2 H) 1.86 (dd, 1 H) | 421 | (Z)-3-(1,3-dioxoisoindolin-2-yl)-N-(1-(2-((2,4-dioxothiazolidin-5-ylidene)methyl)-4,5-dimethoxyphenyl)pyrrolidin-3-yl)propanamide Method 75 |
| 129A | (5Z)-5-{2-[4-(3-aminopropanoyl)piperazin-1-yl]benzylidene}-1,3-thiazolidine-2,4-dione hydrochloride | 12.59 (s, 1 H) 7.94 (s, 1 H) 7.82 (s, 2 H) 7.51-7.44 (m, 2 H) 7.26-7.17 (m, 2 H) 3.66 (m, 2 H) 3.59 (m, 2 H) 3.08-2.97 (m, 2 H) 2.96-2.86 (m, 4 H) 2.74 (m, 2 H) | 361 | (5Z)-(2-(4-(3-(1,3-dioxoisoindolin-2-yl)propanoyl)piperazin-1-yl)benzylidene)thiazolidine-2,4-dione Method 76 |

-continued

| Ex. | Compound | ¹H NMR | m/z | SM |
|---|---|---|---|---|
| 129B | (R,Z)-5-(2-(3-(3-aminopropylamino)piperidin-1-yl)-3-chlorobenzylidene)thiazolidine-2,4-dione | 12.69 (brs, 1 H) 9.31 (brs, 1 H) 8.05 (s, 3 H) 7.56 (d, 1 H) 7.49-7.41 (m, 1 H) 7.37 (t, 1 H) 3.76-3.65 (m, 3 H) 3.16 (brs, 1 H) 3.04 (brs, 2 H) 2.94-2.75 (m, 3 H) 2.33 (brs, 1 H) 2.04-1.92 (m, 2 H) 1.78 (d, 1 H) 1.65 (m, 1 H), 1.50 (m, 1 H) | 395 | (R,Z)-5-(3-chloro-2-(3-(3-(1,3-dioxoisoindolin-2-yl)propylamino)piperidin-1-yl)benzylidene)thiazolidine-2,4-dione Method 171 |
| 129C | 5-(2-(3-aminopropoxy)-5-methoxybenzylidene)thiazolidine-2,4-dione | 12.64 (brs, 1 H) 7.94 (brs, 4 H) 7.11 (m, 2 H) 6.93 (s, 1 H) 4.13 (m, 2 H) 3.77 (s, 3 H) 2.97 (m, 2 H) 2.06 (m, 2 H) | 309 | 5-(2-(3-(1,3-dioxoisoindolin-2-yl)propoxy)-5-methoxybenzylidene)thiazolidine-2,4-dione Method 148 |

Example 130

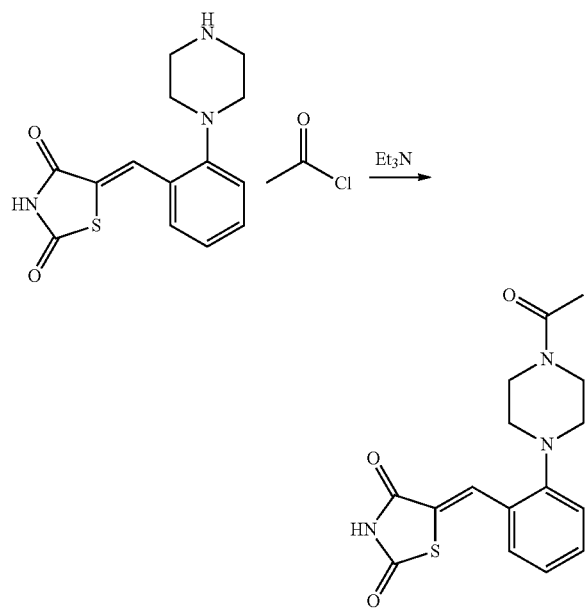

(5Z)-5-[2-(4-acetylpiperazin-1-yl)benzylidene]-1,3-thiazolidine-2,4-dione: To a mixture of (5Z)-5-(2-piperazin-1-ylbenzylidene)-1,3-thiazolidine-2,4-dione (Example 115) and acetyl chloride (36.1 mg, 0.46 mmol) was added triethylamine (93 mg, 0.92 mmol) at room temperature. The reaction mixture was stirred at room temperature overnight and was then treated with sat'd aqueous NaHCO$_3$ (~25 mL). This mixture was allowed to stir at room temperature for 10 min, and was then extracted with DCM (3×25 mL). The combined organic extract was dried over anhydrous Na$_2$SO$_4$, filtered through a bed of Celite, and the filtrate was conc. in vacuo to afford the product which was purified via reverse phase HPLC (acetonitrile:water: 0.1% TFA=5% to 70%) to afford the title compound as a pale yellow solid (40.0 mg, 35.4%). $^1$H NMR (300 MHz, DMSO-D6) δ ppm 12.58 (brs, 1 H) 7.94 (s, 1 H) 7.47 (d, 2 H) 7.30-7.07 (m, 2 H) 3.60 (brs, 4 H) 2.90 (brs, 2 H) 2.85 (brs, 2 H) 2.04 (s, 3 H); m/z 331.

The following examples were prepared by the procedure of Example 130, using the appropriate starting materials.

| Ex. | Compound | $^1$H NMR | m/z | SM |
|---|---|---|---|---|
| 131A | N-(1-{2-[(Z)-(2,4-dioxo-1,3-thiazolidin-5-ylidene)methyl]-4,5-dimethoxyphenyl} pyrrolidin-3-yl)acetamide | 12.29 (brs, 1 H) 8.13 (d, 1 H) 7.85 (s, 1 H) 6.94 (s, 1 H) 6.61 (s, 1 H) 4.27 (d, 1 H) 3.83 (s, 3 H) 3.72 (s, 3 H) 3.43-3.14 (m, 4 H) 2.94 (dd, 1 H) 2.30-2.05 (m, 1 H) 1.82 (s, 3 H) | 392 | (5Z)-5-[2-(3-aminopyrrolidin-1-yl) 4,5-dimethoxybenzylidene]-1,3-thiazolidine-2,4-dione Example 118 |

-continued

| Ex. | Compound | ¹H NMR | m/z | SM |
|---|---|---|---|---|
| 131B | (Z)-N-(4-(3-(dimethylamino)pyrrolidin-1-yl)-3-((2,4-dioxothiazolidin-5-ylidene)methyl)phenyl)acetamide 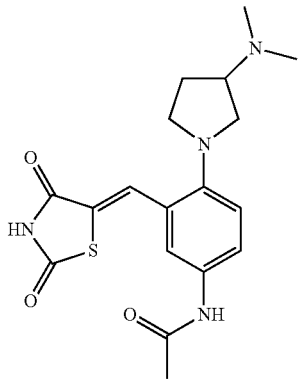 | 9.86 (s, 1 H) 7.68 (s, 1 H) 7.56 (s, 1 H) 7.49-7.47 (d, 1 H) 6.96-6.94 (d, 1 H) 3.23 (m, 1 H) 3.00 (m, 4 H) 2.51 (s, 6 H) 2.15 (m, 1 H) 2.01 (s, 3 H) 1.55 (m, 1 H) | 375 | (Z)-5-(5-amino-2-(3-(dimethylamino)pyrrolidin-1-yl)benzylidene)thiazolidine-2,4-dione Example 151 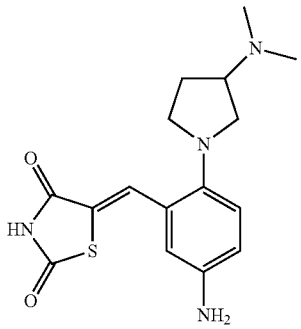 |

Example 132

(Z)-5-(2-(3-(2-hydroxyethylamino)pyrrolidin-1-yl)-4,5-dimethoxybenzylidene)thiazolidine-2,4-dione

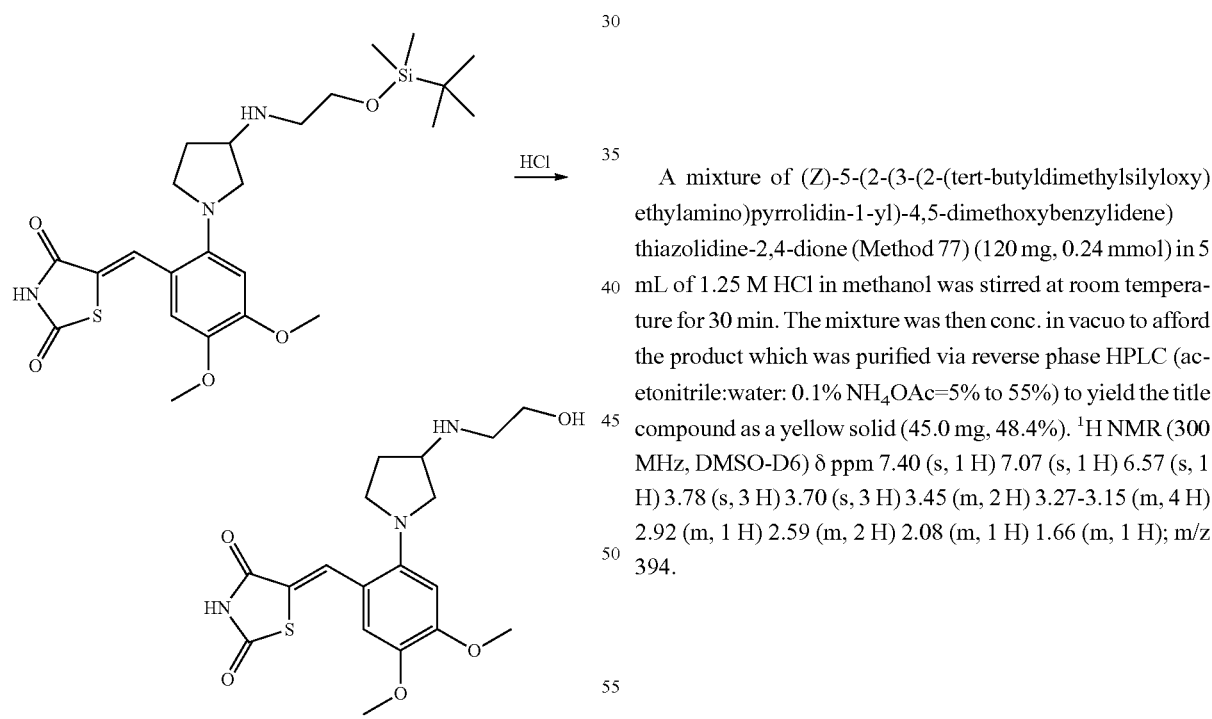

A mixture of (Z)-5-(2-(3-(2-(tert-butyldimethylsilyloxy)ethylamino)pyrrolidin-1-yl)-4,5-dimethoxybenzylidene)thiazolidine-2,4-dione (Method 77) (120 mg, 0.24 mmol) in 5 mL of 1.25 M HCl in methanol was stirred at room temperature for 30 min. The mixture was then conc. in vacuo to afford the product which was purified via reverse phase HPLC (acetonitrile:water: 0.1% $NH_4OAc$=5% to 55%) to yield the title compound as a yellow solid (45.0 mg, 48.4%). ¹H NMR (300 MHz, DMSO-D6) δ ppm 7.40 (s, 1 H) 7.07 (s, 1 H) 6.57 (s, 1 H) 3.78 (s, 3 H) 3.70 (s, 3 H) 3.45 (m, 2 H) 3.27-3.15 (m, 4 H) 2.92 (m, 1 H) 2.59 (m, 2 H) 2.08 (m, 1 H) 1.66 (m, 1 H); m/z 394.

The following examples were prepared by the procedure of Example 132 using the appropriate starting materials.

| | | | | |
|---|---|---|---|---|
| 133 | (R,Z)-5-(3-chloro-2-(3-(2-hydroxyethylamino)piperidin-1-yl)benzylidene)thiazolidine-2,4-dione 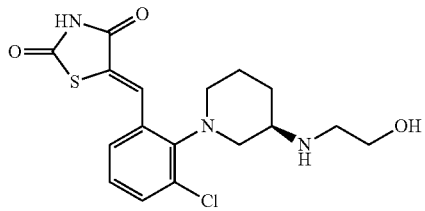 | 8.81 (brs, 2 H) 7.96 (s, 1 H) 7.48 (d, 1 H) 7.40-7.32 (m, 1 H) 7.31-7.25 (m, 1 H) 3.63-3.55 (m, 2 H) 3.46-3.38 (m, 2 H) 3.08 (brs, 2 H) 2.96 (d, 2 H) 2.75 (brs, 1 H) 2.20 (m, 1H) 1.72 (brs, 1 H) 1.56 (brs, 1 H) 1.44 (brs, 1 H) | 382 | (R,Z)-5-(2-(3-(2-(tert-butyldimethylsilyloxy)ethylamino)piperidin-1-yl)-3-chlorobenzylidene)thiazolidine-2,4-dione Method 169 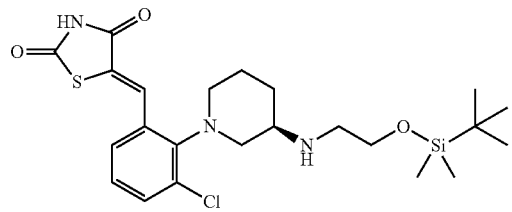 |
| 134 | (R,Z)-5-(3-chloro-2-(3-(3-hydroxypropylamino)piperidin-1-yl)benzylidene)thiazolidine-2,4-dione 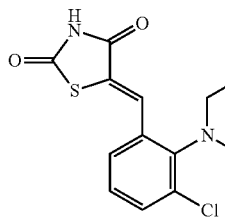 | 12.69 (brs, 1 H) 8.84 (brs, 1 H) 8.04 (s, 1 H) 7.56 (d, 1 H) 7.49-7.39 (m, 1 H) 7.36 (t, 1 H) 3.69 (dd, 2 H) 3.17 (brs, 2 H) 3.00 (brs, 2 H) 2.83 (brs, 1 H) 2.26 (brs, 1 H) 1.93-1.72 (m, 4 H) 1.66 (brs, 1 H) 1.50 (brs, 1 H) | | (R,Z)-5-(2-(3-(3-(tert-butyldimethylsilyloxy)propylamino)piperidin-1-yl)-3-chlorobenzylidene)thiazolidine-2,4-dione Method 170 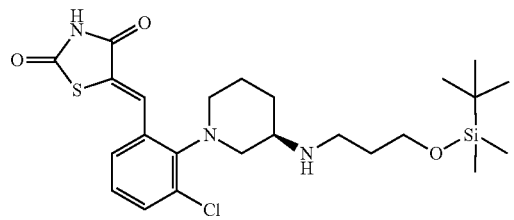 |

Example 135

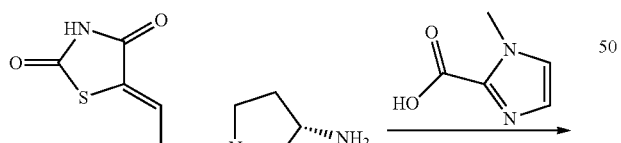

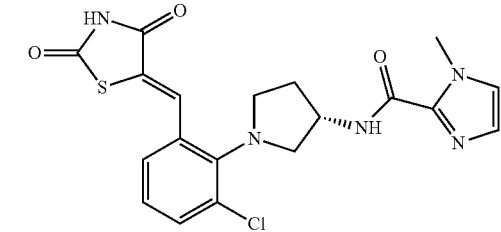

(S,Z)-N-(1-(2-chloro-6-((2,4-dioxothiazolidin-5-ylidene)methyl)phenyl)pyrrolidin-3-yl)-1-methyl-1H-imidazole-2-carboxamide To a 50 mL vial charged with a magnetic stir bar was added (S,Z)-5-(2-(3-aminopyrrolidin-1-yl)-3-chlorobenzylidene)thiazolidine-2,4-dione (75 mg, 0.23 mmol) (Example 86), 1-methyl-1H-imidazole-2-carboxylic acid (87 mg, 0.69 mmol), HATU (220 mg, 0.58 mmol) and dichloromethane (5 mL). Hunig's base (0.202 mL, 1.16 mmol) was then added and the mixture was stirred at rt for 4 h. The reaction was then diluted with dichloromethane and washed with water. The mixture was separated with a phase separator tube and the organic phase was evaporated to dryness. The residue was purified by reverse phase chromatography to afford the title compound as a yellow solid (21 mg, 21%). $^1$H NMR (400 MHz, DMSO-$d_6$) δ ppm 7.89 (s, 1 H) 7.51 (dd, 1 H) 7.41 (dd, 1 H) 7.18-7.27 (m, 2 H) 7.01 (s, 1 H) 4.67-4.77 (m, 1 H) 4.00 (s, 3 H) 3.63-3.75 (m, 2 H) 3.47-3.54 (m, 1 H) 3.36-3.47 (m, 1 H) 2.39-2.51 (m, 1 H) 2.14 (dd, 1 H); m/z 432.

The following examples were prepared by the procedure of 135 using the appropriate starting materials.

| | | | | | |
|---|---|---|---|---|---|
| 136 | (S,Z)-N-(1-(2-chloro-6-((2,4-dioxothiazolidin-5-ylidene)methyl)phenyl)pyrrolidin-3-yl)-2-methoxyacetamide 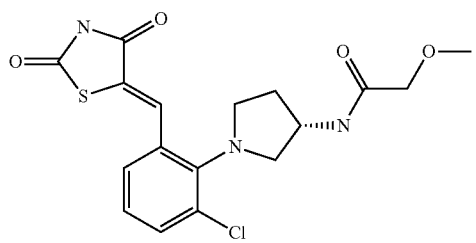 | 7.89 (s, 1 H) 7.52 (dd, 1 H) 7.41 (dd, 1 H) 7.25 (t, 1 H) 4.58-4.67 (m, 1 H) 3.93 (s, 2 H) 3.65 (dd, 1 H) 3.36-3.46 (m, 5 H) 3.13 (dd, 1 H) 2.38 (dd, 1 H) 2.01-2.13 (m, 1 H) | 396 | (S,Z)-5-(2-(3-aminopyrrolidin-1-yl)-3-chlorobenzylidene)thiazolidin-2,4-dione Example 86 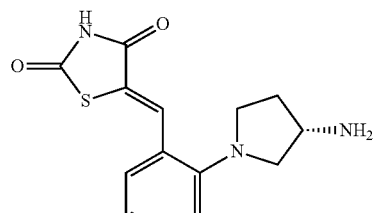 and 2-methoxyacetic acid 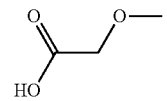 |
| 137 | (S,Z)-N-(1-(2-chloro-6-((2,4-dioxothiazolidin-5-ylidene)methyl)phenyl)pyrrolidin-3-yl)-1-methyl-1H-pyrazole-3-carboxamide 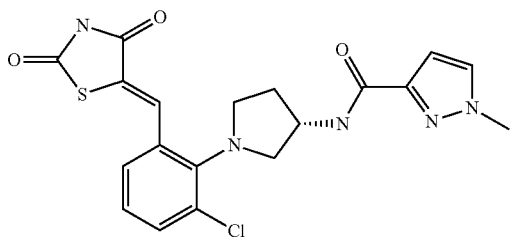 | 7.93 (s, 1 H) 7.61 (d, 1 H) 7.52 (dd, 1 H) 7.42 (dd, 1 H) 7.25 (t, 1 H) 6.73 (d, 1 H) 4.73-4.83 (m, 1 H) 3.92-3.99 (m, 3 H) 3.71 (dd, 1 H) 3.38-3.50 (m, 2 H) 3.23 (dd, 1 H) 2.38-2.50 (m, 1 H) 2.09-2.21 (m, 1 H) | 432 | (S,Z)-5-(2-(3-aminopyrrolidin-1-yl)-3-chlorobenzylidene)thiazolidine-2,4-dione Example 86 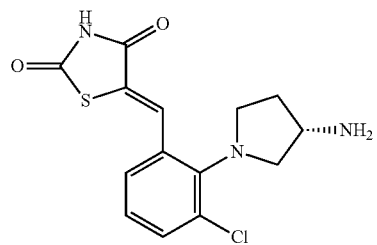 and 1-methyl-1H-pyrazole-3-carboxylic acid 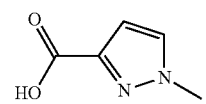 |

| | | | | |
|---|---|---|---|---|
| 138 | (S,Z)-N-(1-(2-chloro-6-((2,4-dioxothiazolidin-5-ylidene)methyl)phenyl)pyrrolidin-3-yl)-2-ureidoacetamide 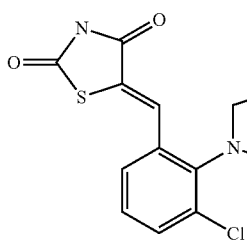 | 7.93 (s, 1 H) 7.52 (dd, 1 H) 7.41 (dd, 1 H) 7.25 (t, 1 H) 4.53 (ddd, 1 H) 3.83-3.92 (m, 2 H) 3.65-3.70 (m, 1 H) 3.42-3.49 (m, 1 H) 3.35-3.42 (m, 1 H) 3.07 (dd, 1 H) 2.37 (dt, 1 H) 1.98-2.10 (m, 1 H) | 424 | (S,Z)-5-(2-(3-aminopyrrolidin-1-yl)-3-chlorobenzylidene)thiazolidin-2,4-dione Example 86 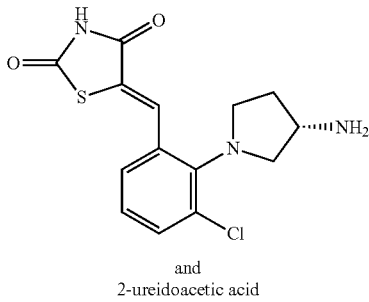 and 2-ureidoacetic acid 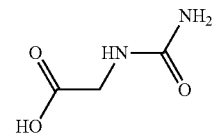 |
| 139 | (S,Z)-N-(1-(2-chloro-6-((2,4-dioxothiazolidin-5-ylidene)methyl)phenyl)pyrrolidin-3-yl)-2-(pyridin-3-yl)acetamide 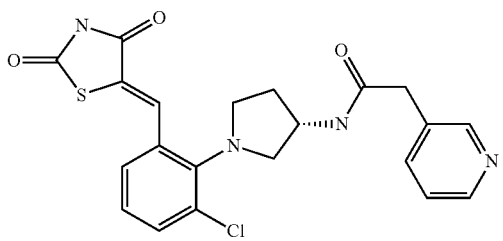 | 8.44 (br. S., 2 H) 8.02 (s, 1 H) 7.83 (d, 1 H) 7.50 (dd, 1 H) 7.34-7.46 (m, 3 H) 7.25 (t, 1 H) 4.51 (t, 1 H) 3.60-3.69 (m, 3 H) 3.37-3.48 (m, 2 H) 3.08 (dd, 1 H) 2.31-2.43 (m, 1 H) 2.03 (dd, 1 H) | 443 | (S,Z)-5-(2-(3-aminopyrrolidin-1-yl)-3-chlorobenzylidene)thiazolidine-2,4-dione Example 86 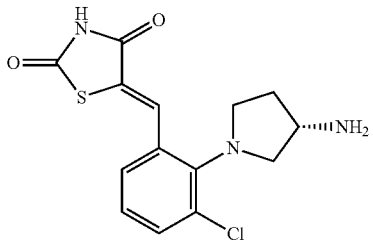 and 2-(pyridin-3-yl)acetic acid 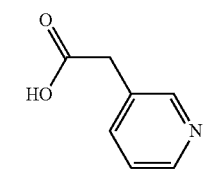 |

| | | | | |
|---|---|---|---|---|
| 140 | (S,Z)-N-(1-(2-chloro-6-((2,4-dioxothiazolidin-5-ylidene)methyl)phenyl)pyrrolidin-3-yl)-2-(pyridin-4-yl)acetamide 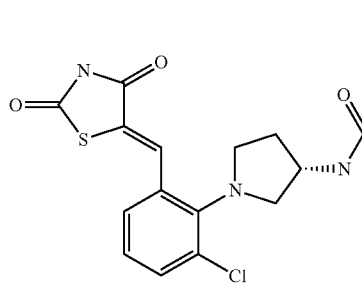 | 8.47 (br. S., 1 H) 7.98 (s, 1 H) 7.53 (dd, 1 H) 7.41 (dd, 3 H) 7.25 (t, 1 H) 4.53 (t, 1 H) 3.64-3.71 (m, 3 H) 3.39-3.48 (m, 2 H) 3.07 (dd, 1 H) 2.32-2.44 (m, 1 H) 2.03 (dd, 1 H) | 443 | (S,Z)-5-(2-(3-aminopyrrolidin-1-yl)-3-chlorobenzylidene)thiazolidine-2,4-dione Example 86 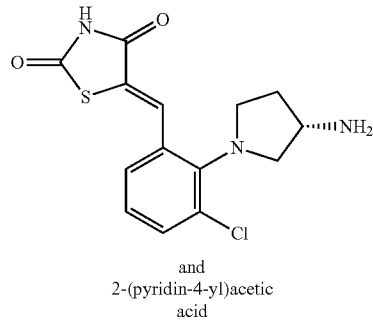 and 2-(pyridin-4-yl)acetic acid 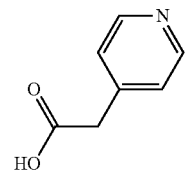 |
| 141 | (S,Z)-N-(1-(2-chloro-6-((2,4-dioxothiazolidin-5-ylidene)methyl)phenyl)pyrrolidin-3-yl)-1-methyl-1H-pyrazole-4-carboxamide 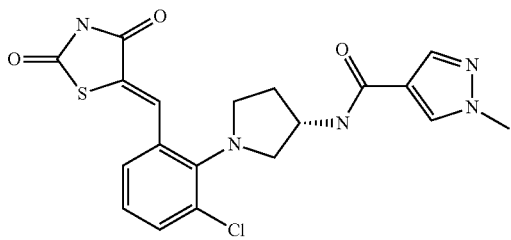 | 8.17 (s, 1 H) 8.07 (s, 1 H) 7.94 (s, 1 H) 7.47 (ddd, 2 H) 7.27 (t, 1 H) 4.67-4.78 (m, 1 H) 3.89-3.97 (m, 3 H) 3.73 (dd, 1 H) 3.44 (t, 2 H) 3.19 (dd, 1 H) 2.42 (dd, 1 H) 2.14 (dd, 1 H) | 432 | (S,Z)-5-(2-(3-aminopyrrolidin-1-yl)-3-chlorobenzylidene)thiazolidine-2,4-dione Example 86 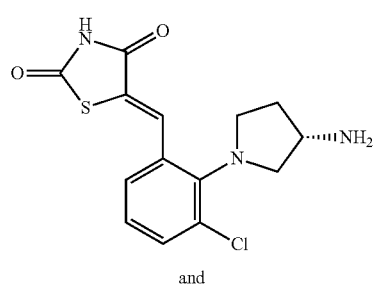 and 1-methyl-1H-pyrazole-4-carboxylic acid 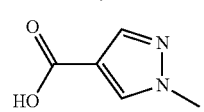 |

| | | | | |
|---|---|---|---|---|
| 142 | (S,Z)-N-(1-(2-chloro-6-((2,4-dioxothiazolidin-5-ylidene)methyl)phenyl)pyrrolidin-3-yl)-2-(oxodothiomorpholin-4-yl)acetamide 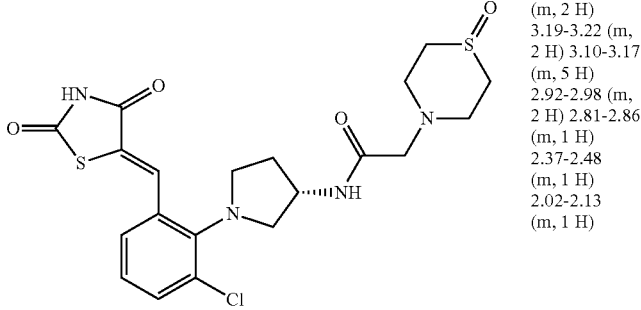 | 7.91 (s, 1 H) 7.56 (dd, 1 H) 7.43 (dd, 1 H) 7.27 (t, 1 H) 4.62 (t, 1 H) 3.67-3.78 (m, 2 H) 3.41-3.48 (m, 2 H) 3.19-3.22 (m, 2 H) 3.10-3.17 (m, 5 H) 2.92-2.98 (m, 2 H) 2.81-2.86 (m, 1 H) 2.37-2.48 (m, 1 H) 2.02-2.13 (m, 1 H) | 483 | (S,Z)-5-(2-(3-aminopyrrolidin-1-yl)-3-chlorobenzylidene)thiazolidine-2,4-dione Example 86 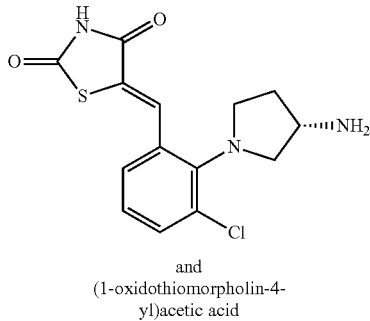 and (1-oxidothiomorpholin-4-yl)acetic acid 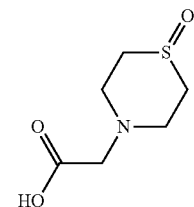 |
| 143 | (S,Z)-N-(1-(2-chloro-6-((2,4-dioxothiazolidin-5-ylidene)methyl)phenyl)pyrrolidin-3-yl)-4-sulfamoylbutanamide 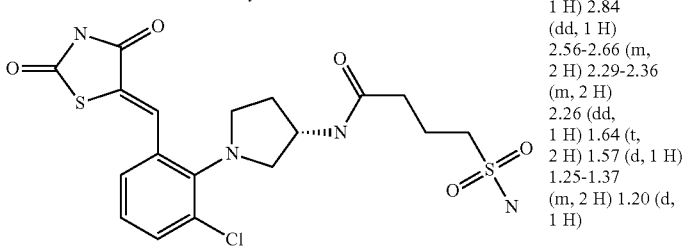 | 7.18 (s, 1 H) 6.70 (dd, 1 H) 6.62 (dd, 1 H) 6.45 (t, 1 H) 3.71 (s, 1 H) 2.84 (dd, 1 H) 2.56-2.66 (m, 2 H) 2.29-2.36 (m, 2 H) 2.26 (dd, 1 H) 1.64 (t, 2 H) 1.57 (d, 1 H) 1.25-1.37 (m, 2 H) 1.20 (d, 1 H) | 473 | (S,Z)-5-(2-(3-aminopyrrolidin-1-yl)-3-chlorobenzylidene)thiazolidine-2,4-dione Example 86 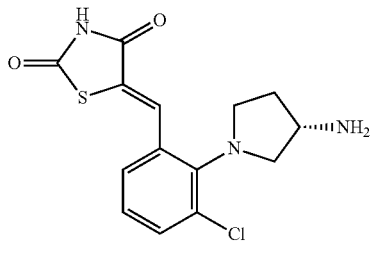 and 4-sulfamoylbutanoic acid 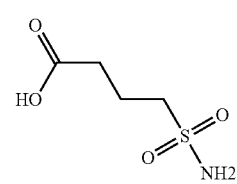 |

| | | | | |
|---|---|---|---|---|
| 144 | (S,Z)-N1-(1-(2-chloro-6-((2,4-dioxothiazolidin-5-ylidene)methyl)phenyl)pyrrolidin-3-yl)-N4,N4-dimethylsuccinamide 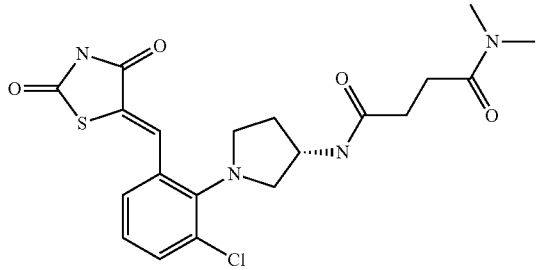 | 8.01 (s, 1 H) 7.50 (d, 1 H) 7.44 (d, 1 H) 7.26 (t, 1 H) 4.47-4.58 (m, 1 H) 3.62 (t, 1 H) 3.42 (t, 2 H) 3.02-3.15 (m, 4 H) 2.92 (s, 3 H) 2.67 (d, 2 H) 2.56 (t, 2 H) 2.36 (dd, 1 H) 2.02 (dd, 1 H) | 451 | (S,Z)-5-(2-(3-aminopyrrolidin-1-yl)-3-chlorobenzylidene)thiazolidine-2,4-dione Example 86 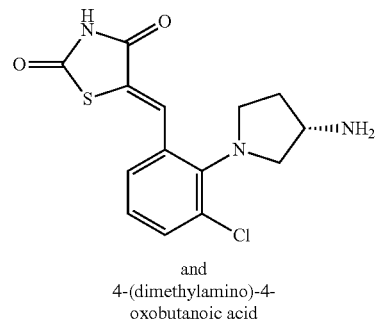 and 4-(dimethylamino)-4-oxobutanoic acid 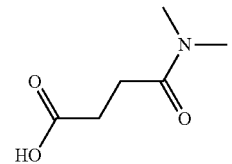 |
| 145 | (S,Z)-N-(1-(2-chloro-6-((2,4-dioxothiazolidin-5-ylidene)methyl)phenyl)pyrrolidin-3-yl)-2-(dimethylamino)acetamide 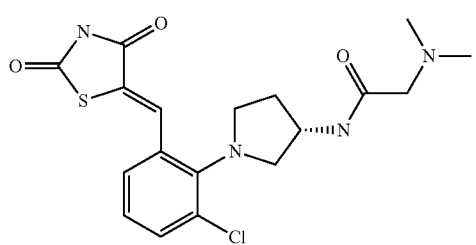 | 7.07 (s, 1 H) 6.69-6.74 (m, 1 H) 6.59 (dd, 1 H) 6.43 (t, 1 H) 3.76 (br. S., 1 H) 2.85-2.94 (m, 2 H) 2.84 (d, 1 H) 2.36 (br. S., 1 H) 2.29 (dd, 2 H) 1.52-1.64 (m, 7 H) 1.18-1.28 (m, 1 H) | 409 | (S,Z)-5-(2-(3-aminopyrrolidin-1-yl)-3-chlorobenzylidene)thiazolidine-2,4-dione Example 86 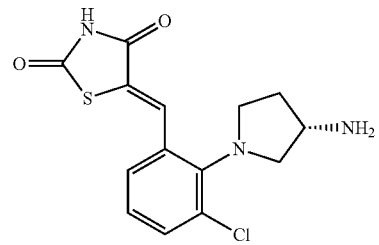 and 2-(dimethylamino)acetic acid 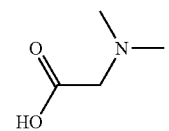 |

| 146 | (S,Z)-N-(1-(2-chloro-6-((2,4-dioxothiazolidin-5-ylidene)methyl)phenyl)pyrrolidin-3-yl)-2-cyanoacetamide 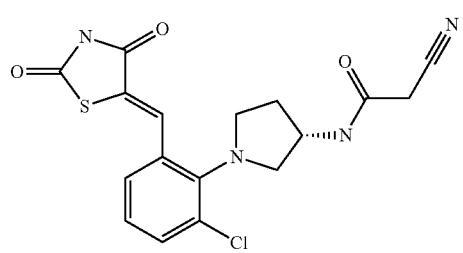 | 7.95 (s, 1 H) 7.52 (dd, 1 H) 7.42 (dd, 1 H) 7.26 (t, 1 H) 4.50 (ddd, 1 H) 3.68-3.78 (m, 1 H) 3.64 (dd, 1 H) 3.44-3.50 (m, 1 H) 3.40 (t, 1 H) 3.22 (q, 1 H) 3.09 (dd, 1 H) 2.39 (dt, 1 H) 2.03 (d, 1 H) | 391 | (S,Z)-5-(2-(3-aminopyrrolidin-1-yl)-3-chlorobenzylidene)thiazolidin-2,4-dione Example 86 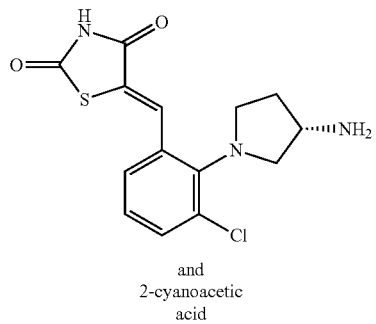 and 2-cyanoacetic acid 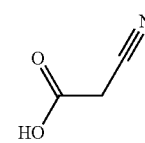 |
|---|---|---|---|---|
| 147 | (S,Z)-2-acetamido-N-(1-(2-chloro-6-((2,4-dioxothiazolidin-5-ylidene)methyl)phenyl)pyrrolidin-3-yl)acetamide 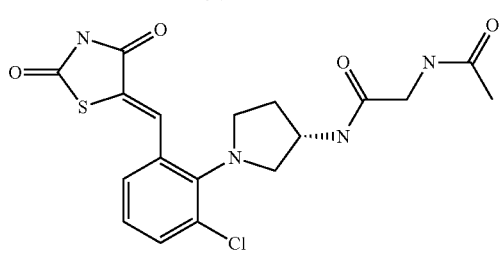 | 7.89 (s, 1 H) 7.54 (dd, 1 H) 7.39 (dd, 1 H) 7.24 (t, 1 H) 4.49-4.60 (m, 1 H) 3.86-3.98 (m, 1 H) 3.65 (dd, 1 H) 3.36-3.48 (m, 2 H) 3.17-3.25 (m, 1 H) 3.07-3.16 (m, 1 H) 2.31-2.43 (m, 1 H) 1.96-2.09 (m, 4 H) | 423 | (S,Z)-5-(2-(3-aminopyrrolidin-1-yl)-3-chlorobenzylidene)thiazolidine-2,4-dione Example 86 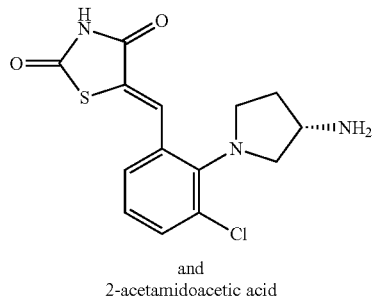 and 2-acetamidoacetic acid 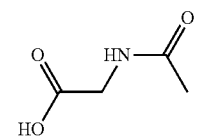 |

Example 148

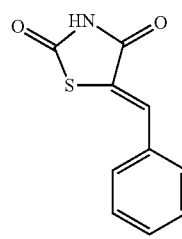 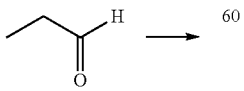 →

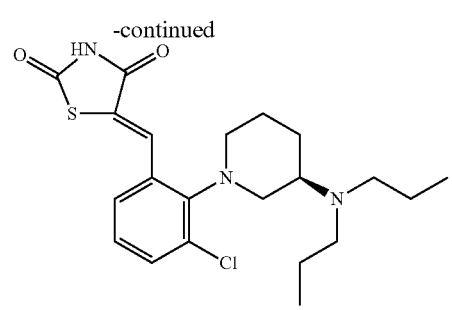

(R,Z)-5-(3-chloro-2-(3-(dipropylamino)piperidin-1-yl)benzylidene)thiazolidine-2,4-dione A mixture of (R,Z)-5-(2-(3-aminopiperidin-1-yl)-3-chlorobenzylidene)thiazolidine-2,4-dione (122D) (100 mg, 0.27 mmol) and propionaldehyde (20.17 mg, 0.35 mmol) in CH$_2$Cl$_2$ (15 mL) was stirred at 50° C. for 20 min. before sodium triacetoxyborohydride (170 mg, 0.80 mmol) was added. The mixture was then stirred at 50° C. for 4 h. before sat'd aqueous K$_2$CO$_3$ (~50 mL) was added to the mixture. This solution was poured into a separatory funnel and extracted with CHCl$_3$/isopropanol (5/1) (2×50 mL). The combined organic extract was dried over anhydrous Na$_2$SO$_4$, filtered, and conc. in vacuo affording the product. It was purified with Gilson (0.1% TFA in water:0.1% TFA in CAN=30% to 80%; UV absorption at 322) to yield the title compound as a yellow solid (94 mg, 77%). $^1$H NMR (400 MHz, DMSO-d$_6$) δ ppm 7.96 (s, 1 H) 7.48 (d, 1 H) 7.41-7.34 (m, 1 H) 7.29 (t, 1 H) 3.67-3.58 (m, 2 H) 3.44-3.37 (m, 2 H) 3.03-2.78 (m, 5 H) 2.21 (brs, 1 H), 1.79 (d, 1 H) 1.61 (d, 6 H) 0.84-0.79 (m, 6 H). m/z 422.

He following examples were prepared by the procedure of 148, using the appropriate starting materials.

Example 151

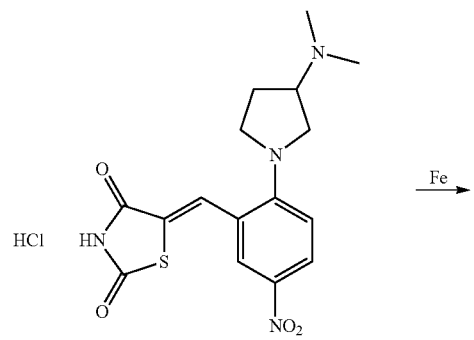

| | | | | |
|---|---|---|---|---|
| 149 | (R,Z)-5-(3-chloro-2-(3-(3,3,3-trifluoropropylamino)piperidin-1-yl)benzylidene)thiazolidine-2,4-dione 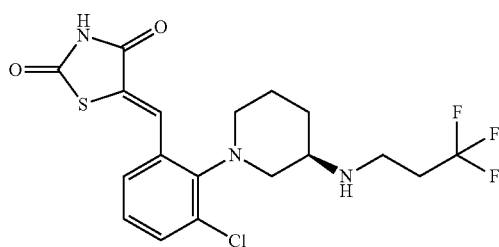 | 12.65 (brs,1 H) 9.35 (brs, 1H) 8.05 (s, 1 H) 7.56 (d, 1 H) 7.44 (brs, 1 H) 7.37 (t, 1 H) 3.75-3.63 (m, 2 H) 3.53-3.45 (m, 2 H) 3.23 (m, 1 H) 2.85-2.65 (m, 4 H) 2.30 (brs, 1 H) 1.85-1.76 (m, 1 H) 1.67 (brs, 1 H) 1.49 (brs, 1 H) | 433 | (R,Z)-5-(2-(3-aminopiperidin-1-yl)-3-chlorobenzylidene)thiazolidine-2,4-dione hydrochloride Example 122D 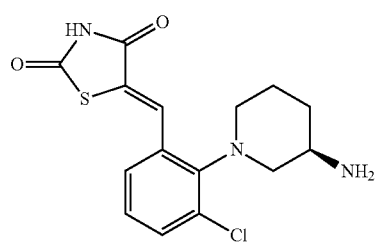 and 3,3,-trifluoropropanal 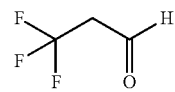 |
| 150 | 5-(2-(3-(isopropylamino)propoxy)-5-methoxybenzylidene)thiazolidine-2,4-dione 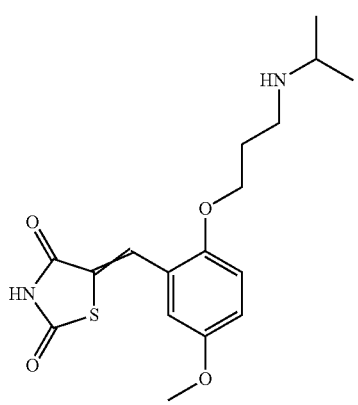 | 12.65 (s, 1H), 8.91 (s, br, 2H), 7.91 (s, 1H), 7.10 (m, 2H), 7.85 (s, 1H), 4.17 (m, 2H), 3.65 (m, 4H), 3.05 (m, 2H), 2.14 (m, 2H), 1.22 (m, 6H) | 351 | 5-(2-(3-aminoproxy)-5-methoxybenzylidene)thiazolidine-2,4-dione hydrochloride Example 129C 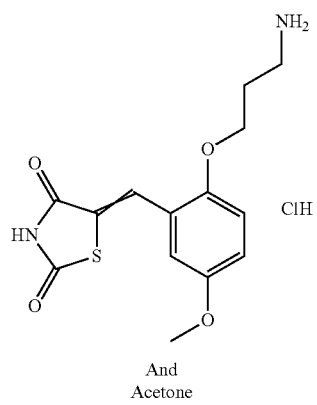 And Acetone  |

195
-continued

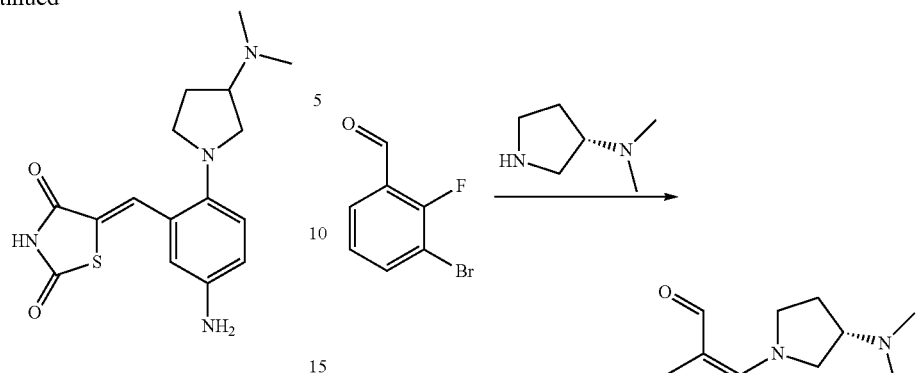

(Z)-5-(5-amino-2-(3-(dimethylamino)pyrrolidin-1-yl)benzylidene)thiazolidine-2,4-dione To a mixture of (Z)-5-(2-(3-(dimethylamino)pyrrolidin-1-yl)-5-nitrobenzylidene)thiazolidine-2,4-dione (100 mg, 0.28 mmol) (Method 149) and iron (154 mg, 2.76 mmol) chip in MeOH (10 mL) was added 5 drops of conc. HCl and 5 drops of water. The mixture was stirred at 80° C. for 1 hr. The mixture was loaded into silica gel, purified with ISCO (100% ethyl acetate to methanol/ethyl acetate=50%) to yield a red solid which was repurified with Gilson (acetonitrile:water: 0.1% TFA=0% to 50% fro 7 min) to yield a yellow solid as (Z)-5-(5-amino-2-(3-(dimethylamino)pyrrolidin-1-yl)benzylidene)thiazolidine-2,4-dione (51.0 mg, 38.6%). $^1$H NMR (400 MHz, DMSO-d6) δ ppm 12.55 (brs, 1 H), 11.32 (brs, 1 H), 10.30 (brs, 2 H), 7.80 (s, 1 H), 7.42 (m, 2 H), 7.19 (m, 1 H), 3.95 (m, 1 H), 3.39-3.27 (m, 4 H), 2.78 (s, 6 H), 2.30-2.10 (m, 2 H); m/z 333.

The following intermediates were prepared by the procedure of Example 151 using the appropriate starting materials.

196
Methods Section

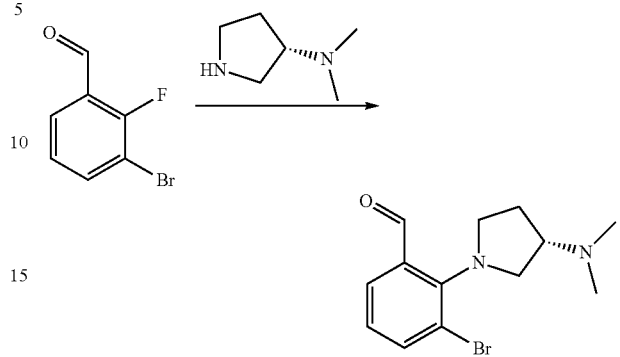

Method 1:

(S)-3-bromo-2-(3-(dimethylamino)pyrrolidin-1-yl)benzaldehyde

A 50 mL round bottom flask was charged with a magnetic stir bar, 3-bromo-2-fluorobenzaldehyde (0.555 g, 2.73 mmol), (S)-N,N-dimethylpyrrolidin-3-amine (0.312 g, 2.73 mmol), DMSO (5.47 ml), and potassium carbonate (0.378 g, 2.73 mmol). The mixture was heated to 85° C. overnight with stirring. The reaction was allowed to cool to ambient temperature, was diluted with water, and extracted into methylene chloride. The combined organic extract was dried with MgSO$_4$, filtered, and conc. in vacuo to provide the product which was purified via silica gel chromatography (40 g) using ethyl acetate/MeOH (10:1) as eluent to afford (S)-3-bromo-2-(3-(dimethylamino)pyrrolidin-1-yl)benzaldehyde (0.369 g, 45.4%).

The following intermediates were prepared by the procedure of Method 1, using the appropriate starting materials.

| Ex | Compound | $^1$H NMR | m/z | SM |
|---|---|---|---|---|
| 152 | (Z)-5-(2-amino-4,5-dimethoxybenzylidene)thiazolidine-2,4-dione | 12.45 (brs, 1 H) 7.87 (s, 1 H) 6.80 (s, 1 H) 6.79 (s, 1 H) 3.78 (s, 3 H) 3.73 (s, 3 H) | 280 | (Z)-5-(4,5-dimethoxy-2-nitrobenzylidene)thiazolidine-2,4-dione Method 150 |

| Method | Compound | ¹H NMR | m/z | SM |
|---|---|---|---|---|
| 2 | 2-((3S,5R)-3,5-dimethylpiperazin-1-yl)-5-(trifluoromethyl)benzaldehyde | | 287 | 2-fluoro-5-(trifluoromethyl)benazldehyde and (2R,6S)-2,6-dimethylpiperazine |
| 3 | 2-((3S,5R)-3,5-dimethylpiperazin-1-yl)-3-methoxybenzaldehyde | | 249 | 2-fluoro-3-methoxybenazldehyde and (2R,6S)-2,6-dimethylpiperazine |
| 4 | (S)-2-(3-(dimethylamino)pyrrolidin-1-yl)-3-methoxybenzaldehyde | | 249 | 2-fluoro-3-methoxybenazldehyde and (3S)-N,N-dimethylpyrrolidin-3-amine |

| Method | Compound | ¹H NMR | m/z | SM |
|---|---|---|---|---|
| 5 | 3-chloro-2-((3S,5R)-3,5-dimethylpiperazin-1-yl)benzaldehyde 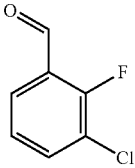 | | 254 | 3-chloro-2-fluorobenzaldehyde 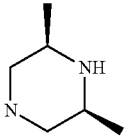 and (2R,6S)-2,6-dimethylpiperazine |
| 6 | (S)-3-chloro-2-(3-(dimethylamino)pyrrolidin-1-yl)benzaldehyde  | | 253 | 3-chloro-2-fluorobenzaldehyde 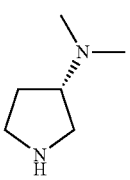 and (3S)-N,N-dimethylpyrrolidin-3-amine |
| 7 | (R)-2-(3-(dimethylamino)pyrrolidin-1-yl)-4,5-dimethoxybenzaldehyde 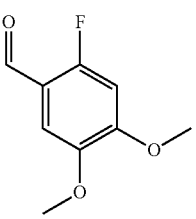 | | 279 | 2-fluoro-4,5-dimethoxybenzaldehyde 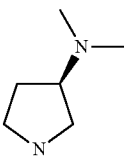 and (3R)-N,N-dimethylpyrrolidin-3-amine |

-continued

| Method | Compound | ¹H NMR | m/z | SM |
|---|---|---|---|---|
| 8 | (S)-2-(3-(dimethylamino)pyrrolidin-1-yl)-4,5-dimethoxybenzaldehyde 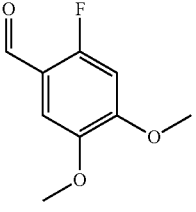 | | 279 | 2-fluoro-4,5-dimethoxybenzaldehyde 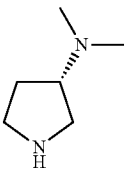 and (3S)-N,N-dimethylpyrrolidin-3-amine |
| 9 | 2-(4-(hydroxymethyl)piperidin-1-yl)-4,5-dimethoxybenzaldehyde 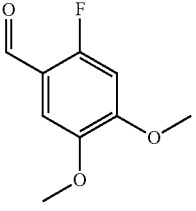 | | 280 | 2-fluoro-4,5-dimethoxybenzaldehyde 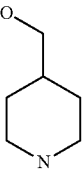 and piperidin-4-ylmethanol |
| 10 | 2-(4-(hydroxypiperidin-1-yl)-4,5-dimethoxybenzaldehyde 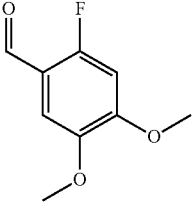 | | 266 | 2-fluoro-4,5-dimethoxybenzaldehyde 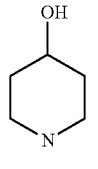 and piperidin-4-ol |

-continued

| Method | Compound | ¹H NMR | m/z | SM |
|---|---|---|---|---|
| 11 | 2-(3-(dimethylamino)pyrrolidin-1-yl)-5-methoxybenzaldehyde 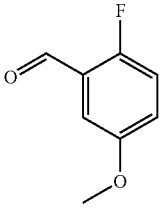 | | 249 | 2-fluoro-5-methoxybenzaldehyde 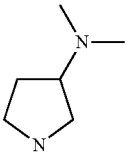 and N,N-dimethylpyrrolidin-3-amine |
| 12 | 2-(4-(dimethylamino)piperidin-1-yl)-5-methoxybenzaldehyde 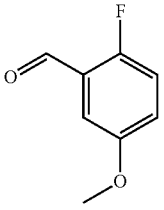 | | 263 | 2-fluoro-5-methoxybenzaldehyde 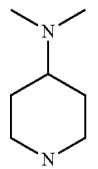 and N,N-dimethylpiperidin-4-amine |
| 13 | 2-(3-hydroxypyrrolidin-1-yl)-4,5-dimethoxybenzaldehyde 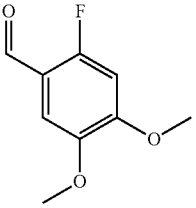 | | 253 | 2-fluoro-4,5-dimethoxybenzaldehyde 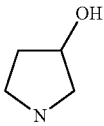 and pyrrolidin-3-ol |

-continued
| Method | Compound | ¹H NMR | m/z | SM |
|---|---|---|---|---|
| 14 | 4,5-dimethoxy-2-(pyrrolidin-1-yl)benzaldehyde 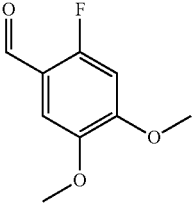 | | 236 | 2-fluoro-4,5-dimethoxybenzaldehyde  and pyrrolidine |
| 15 | 2-((2-(dimethylamino)ethyl)(methyl)amino)benzaldehyde 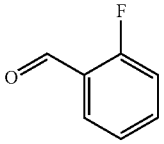 | | 207 | 2-fluorobenzaldehyde 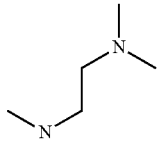 and N,N,N'-trimethylethane-1,2-diamine |
| 16 | 2-(3-(dimethylamino)pyrrolidin-1-yl)benzaldehyde 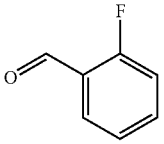 | | 219 | 2-fluorobenzaldehyde 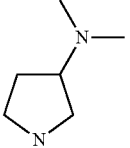 and N,N-dimethylpyrrolidin-3-amine |

-continued
| Method | Compound | ¹H NMR | m/z | SM |
|---|---|---|---|---|
| 17 | 2-(4-(dimethylamino)piperidin-1-yl)benzaldehyde 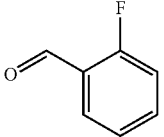 | | 233 | 2-fluorobenzaldehyde and N,N-dimethylpiperidin-4-amine 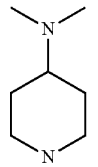 |
| 18 | 2-(4-isopropylpiperazin-1-yl)benzaldehyde 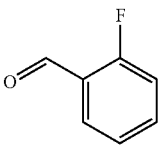 | | 233 | 2-fluorobenzaldehyde and 1-isopropylpiperazine 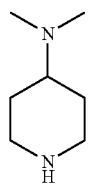 |
| 19 | 2-((2-(dimethylamino)ethyl)(methyl)amino)-4,5-dimethoxybenzaldehyde 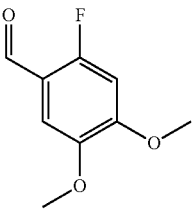 | | 267 | 2-fluoro-4,5-dimethoxybenzaldehyde and N,N,N'-trimethylethane-1,2-diamine 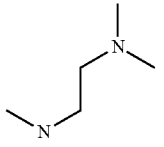 |

-continued

| Method | Compound | ¹H NMR | m/z | SM |
|---|---|---|---|---|
| 20 | 2-(3-(dimethylamino)pyrrolidin-1-yl)-4,5-dimethoxybenzaldehyde 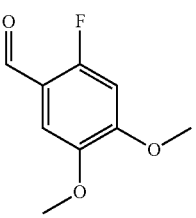 | | 279 | 2-fluoro-4,5-dimethoxybenzaldehyde 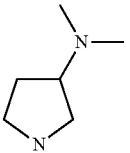 and N,N-dimethylpyrrolidin-3-amine |
| 21 | 2-(4-isopropylpiperazin-1-yl)-4,5-dimethoxybenzaldehyde 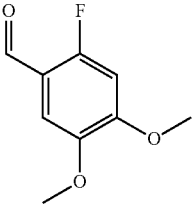 | | 293 | 2-fluoro-4,5-dimethoxybenzaldehyde 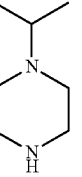 and 1-isopropylpiperazine |
| 22 | 2-(4-(dimethylamino)piperidin-1-yl)-4,5-dimethoxybenzaldehyde 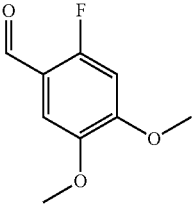 | | 293 | 2-fluoro-4,5-dimethoxybenzaldehyde 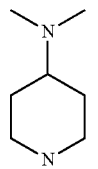 and N,N-dimethylpiperidin-4-amine |

| Method | Compound | ¹H NMR | m/z | SM |
|---|---|---|---|---|
| 23 | tert-butyl 4-(2-formyl-4-(trifluoromethyl)phenyl)piperazine-1-carboxylate 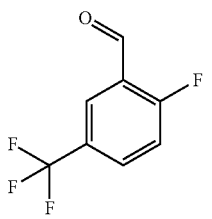 | | 359 | 2-fluoro-5-(trifluoromethyl)benzaldehyde 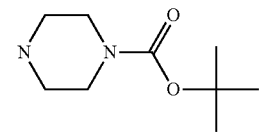 and tert-butyl piperazine-1-carboxylate |
| 24 | 2-(3-(dimethylamino)pyrrolidin-1-yl)-5-nitrobenzaldehyde 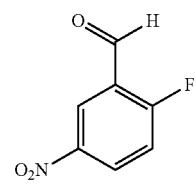 | | 264 | 2-fluoro-5-nitrobenzaldehyde 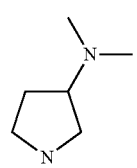 and N,N-dimethylpyrrolidin-3-amine |
| 25 | 4-(3-(dimethylamino)pyrrolidin-1-yl)-3-formylbenzaldehyde 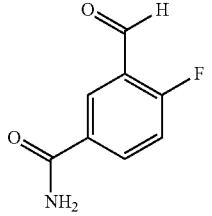 | | 262 | 4-fluoro-3-formylbenzaldehyde 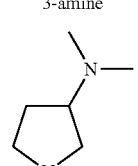 and N,N-dimethylpyrrolidin-3-amine |

-continued

| Method | Compound | ¹H NMR | m/z | SM |
|---|---|---|---|---|
| 26 | tert-butyl 4-(2-formylphenyl)piperazine-1-carboxylate 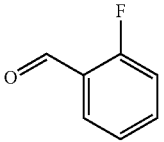 | | 291 | 2-fluorobenzaldehyde 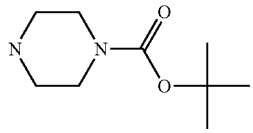<br>and<br>tert-butyl piperazine-1-carboxylate |
| 79 | tert-butyl [(3S)-1-(2-chloro-6-formylphenyl)pyrrolidin-3-yl]carbamate  | | 326 | 3-chloro-2-fluorobenzaldehyde 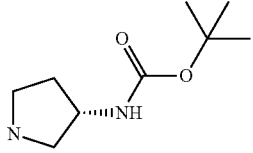<br>and<br>tert-butyl (3S)-pyrrolidin-3-ylcarbamate |
| 80 | tert butyl 4-[2-formyl 4-(trifluoromethyl)phenyl]piperazine-1-carboxylate 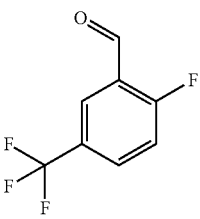 | | 359 | 2-fluoro-5-(trifluoromethyl)benzaldehyde 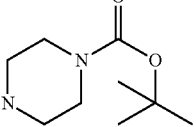<br>and<br>tert-butyl piperazine-1-carboxylate |

-continued

| Method | Compound | ¹H NMR | m/z | SM |
|---|---|---|---|---|
| 81 | tert-butyl{(3S)-1-[2-formyl-4-(trifluoromethyl)phenyl]pyrrolidin-3-yl}carbamate 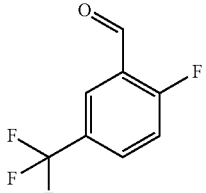 | | 359 | 2-fluoro-5-(trifluoromethyl)benzaldehyde 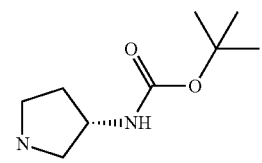 and tert-butyl (3S)-pyrrolidin-3-ylcarbamate |
| 82 | tert butyl 4-(3-formylpyridin-2-yl)piperazine-1-carboxylate 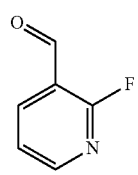 | | 292 | 2-fluoronicotinaldehyde 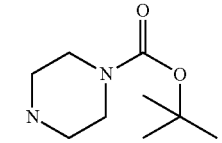 and tert-butyl piperazine-1-carboxylate |
| 83 | tert-butyl [(3S)-1-(2-formyl-6-methoxyphenyl)pyrrolidin-3-yl]carbamate  | | 322 | 2-fluoro-3-methoxybenzaldehyde 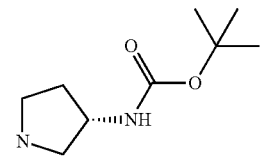 and tert-butyl (3S)-pyrrolidin-3-ylcarbamate |

| Method | Compound | ¹H NMR | m/z | SM |
|---|---|---|---|---|
| 84 | tert-butyl 4-(2-formyl 6-methoxyphenyl] piperazine-1-carboxylate  | | 321 | 2-fluoro-3-methoxybenzaldehyde 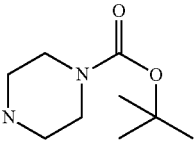 and tert-butyl piperazine-1-carboxylate |
| 85 | tert-butyl 4-(2-chloro 6-formylphenyl) piperazine-1-carboxylate  | | 326 | 3-chloro-2-fluorobenzaldehyde 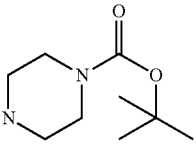 and tert-butyl piperazine-1-carboxylate |
| 86 | tert-butyl (1-(2-formyl-4,5-dimethoxyphenyl) pyrrolidin-3-yl)methylcarbamate 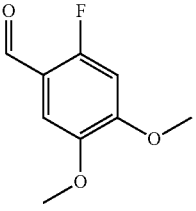 | | 365 | 2-fluoro-4,5-dimethoxybenzaldehyde 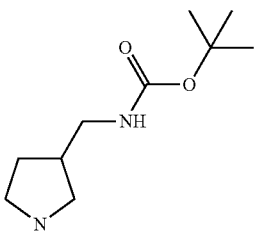 and tert-butyl (pyrrolidin-3-ylmethyl)carbamate |

-continued

| Method | Compound | ¹H NMR | m/z | SM |
|---|---|---|---|---|
| 87 | (R)-tert-butyl 1-(2-formyl-4,5-dimethoxyphenyl)pyrrolidin-3-ylcarbamate 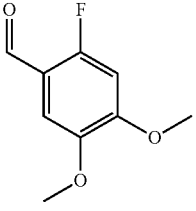 | | 351 | 2-fluoro-4,5-dimethoxybenzaldehyde 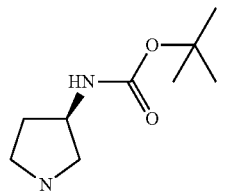 and tert-butyl (3R)-pyrrolidin-3-ylcarbamate |
| 88 | (S)-tert-butyl 1-(2-formyl-4,5-dimethoxyphenyl)pyrrolidin-3-ylcarbamate 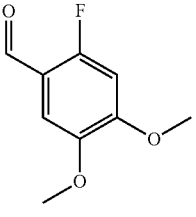 | | 351 | 2-fluoro-4,5-dimethoxybenzaldehyde 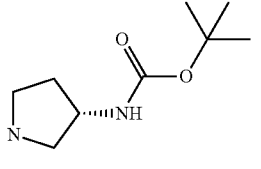 and tert-butyl (3S)-pyrrolidin-3-ylcarbamate |
| 89 | tert-butyl 4-(2-formylphenyl)-1,4-diazepane-1-carboxylate 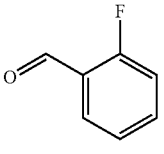 | | 305 | 2-fluorobenzaldehyde 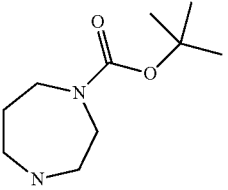 and tert-butyl 1,4-diazepane-1-carboxylate |

| Method | Compound | ¹H NMR | m/z | SM |
|---|---|---|---|---|
| 90 | tert-butyl 1-(2-formyl-4,5-dimethoxyphenyl)pyrrolidin-3-ylcarbamate 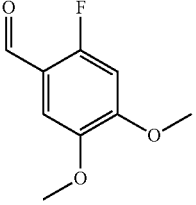 | | 351 | 2-fluoro-4,5-dimethoxybenzaldehyde 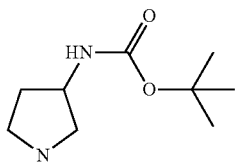 and tert-butyl pyrrolidin-3-ylcarbamate |
| 91 | (R)-tert-butyl (1-(2-chloro-6-formylphenyl)pyrrolidin-3-yl)methylcarbamate 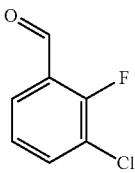 | | 339 | 3-chloro-2-fluorobenzaldehyde 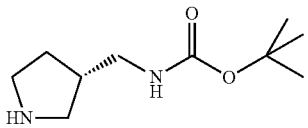 and (S)-tert-butyl pyrrolidin-3-ylmethylcarbamate |
| 92 | (S)-tert-butyl (1-(2-chloro-6-formylphenyl)pyrrolidin-3-yl)methylcarbamate  | | 339 | 3-chloro-2-fluorobenzaldehyde 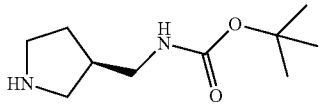 and (R)-tert-butyl pyrrolidin-3-ylmethylcarbamate |

| Method | Compound | ¹H NMR | m/z | SM |
|---|---|---|---|---|
| 93 | (R)-tert-butyl 1-(2-chloro-6-formylphenyl)piperidin-3-ylcarbamate 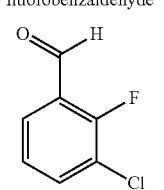 | | 339 | 3-chloro-2-fluorobenzaldehyde 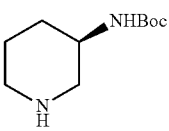 and (R)-tert-butyl piperdin-3-ylcarbamate |
| 94 | (R)-tert-butyl 1-(2-formyl-6-methoxyphenyl)piperidin-3-ylcarbamate 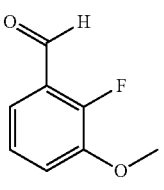 | | 335 | 2-fluoro-3-methoxybenzaldehyde 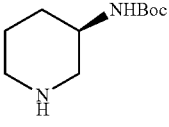 and (R)-tert-butyl piperdin-3-ylcarbamate |
| 95 | (R)-tert-butyl 1-(2-bromo-6-methoxyphenyl)piperidin-3-ylcarbamate 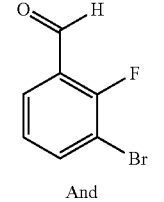 | | 385 | 3-bromo-2-fluorobenzaldehyde 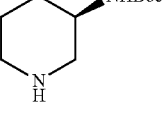 And (R)-tert-butyl piperidin-3-ylcarbamate |

-continued

| Method | Compound | ¹H NMR | m/z | SM |
|---|---|---|---|---|
| 96 | (R)-tert-butyl 1-(2-chloro-6-formylphenyl)pyrrolidin-3-ylcarbamate 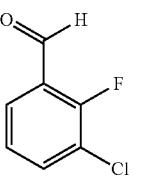 | | 325 | 3-chloro-2-fluorobenzaldehyde 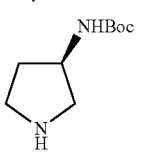 And (R)-tert-butyl pyrrolidin-3-ylcarbamate |
| 97 | (S) tert butyl 1-(2-bromo-6-formylphenyl)pyrrolidin-3-ylcarbamate 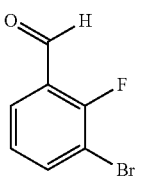 | | 371 | 3-bromo-2-fluorobenzaldehyde 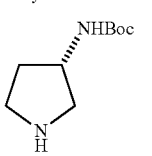 And (S)-tert-butyl pyrrolidin-3-ylcarbamate |
| 98 | (R)-tert butyl 1-(2-ethoxy-6-formylphenyl)piperidin-3-ylcarbamate 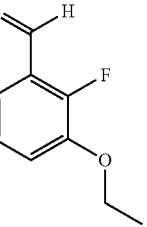 | | 349 | 3-ethoxy-2-fluorobenzaldehyde Method 172 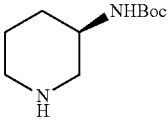 And (R)-tert-butyl piperidin-3-ylcarbamate |

-continued

| Method | Compound | ¹H NMR | m/z | SM |
|---|---|---|---|---|
| 99 | (R)-tert butyl 1-(2-formyl-6-isobutoxyphenyl)piperidin-3-ylcarbamate 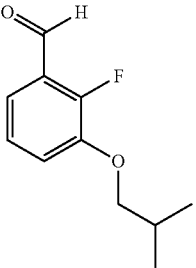 | | 377 | 2-fluoro-3-isobutoxybenzaldehyde Method 173 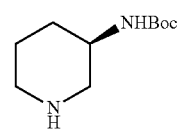 And (R)-tert-butyl piperidin-3-ylcarbamate |
| 100 | (R)-tert butyl 1-(2-(cyclohexylmethoxy)-6-formylphenyl)piperidin-3-ylcarbamate 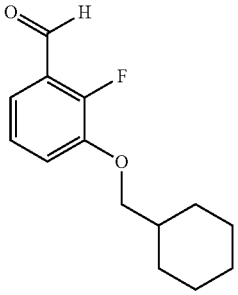 | | 417 | 3-(cyclohexylmethoxy)-2-fluorobenzaldehyde Method 174 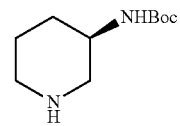 And (R)-tert-butyl piperidin-3-ylcarbamate |
| 101 | (R)-tert butyl 1-(2-(cyclohexyloxy)-6-formylphenyl)piperidin-3-ylcarbamate 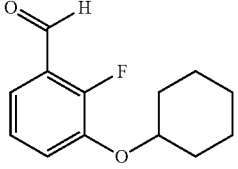 | | 403 | 3-(cyclohexyloxy)-2-fluorobenzaldehyde Method 175 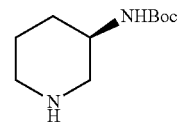 And (R)-tert-butyl piperidin-3-ylcarbamate |

-continued

| Method | Compound | ¹H NMR | m/z | SM |
|---|---|---|---|---|
| 102 | (±)-tert butyl 1-(2-chloro-6-formylphenyl)-4-hydroxypiperidin-3-ylcarbamate | | 354 | 3-chloro-2-fluorobenzaldehyde<br><br>And<br>(±)-tert-butyl-4-hydroxypiperidin-3-ylcarbamate<br>Method 189 |
| 103 | tert-butyl 4-(2-chloro-6-formylphenyl)-1,4-diazepane-1-carboxylate | 10.49 (s, 1 H), 7.75 (d, 1 H), 7.63 (d, 1 H), 7.25 (t, 1 H), 3.37 (brs, 4 H), 1.88 (brs, 2 H), 1.53 (s, 9 H) | 339 | 3-chloro-2-fluorobenzaldehyde<br><br>And<br>tert-butyl 1,4-diazepane-1-carboxylate |
| 104 | (S)-2-(3-(dimethylamino)pyrrolidin-1-yl)-5-methoxybenzaldehyde | | 249 | 2-fluoro-5-methoxybenzaldehyde<br><br>And<br>(S)-N,N-dimethylpyrrolidin-3-amine |

-continued

| Method | Compound | ¹H NMR | m/z | SM |
|---|---|---|---|---|
| 105 | (S)-2-(3-(dimethylamino)pyrrolidin-1-yl)-5-(trifluoromethyl)benzaldehyde 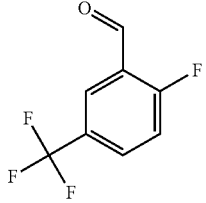 | | 287 | 2-fluoro-5-(trifluoromethyl)benzaldehyde 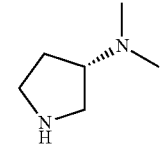 And (S)-N,N-dimethylpyrrolidin-3-amine |
| 106 | (S)-5-chloro-2-(3-(dimethylamino)pyrrolidin-1-yl)benzaldehydeMethod 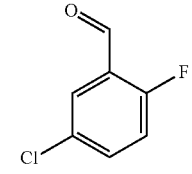 | | 253 | 5-chloro-2-fluorobenzaldehyde 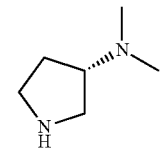 And (S)-N,N-dimethylpyrrolidin-3-amine |
| 107 | (S)-2-(3-(dimethylamino)pyrrolidin-1-yl)-4-methylbenzaldehyde 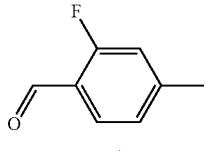 | | 233 | 2-fluoro-4-methylbenzaldehyde 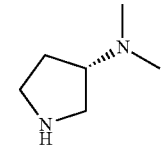 And (S)-N,N-dimethylpyrrolidin-3-amine |

-continued

| Method | Compound | ¹H NMR | m/z | SM |
|---|---|---|---|---|
| 108 | (S)-2-(3-(dimethylamino)pyrrolidin-1-yl)-5-fluorobenzaldehyde  | | 237 | 2,5-difluorobenzaldehyde 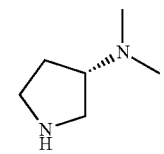 And (S)-N,N-dimethylpyrrolidin-3-amine |
| 109 | (S)-2-(3-(dimethylamino)pyrrolidin-1-yl)-5-methylbenzaldehyde 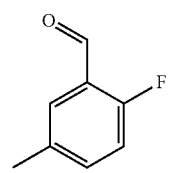 | | 233 | 2-fluoro-5-methylbenzaldehyde 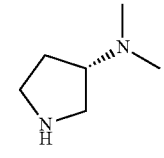 And (S)-N,N-dimethylpyrrolidin-3-amine |
| 110 | (S)-5-bromo-2-(3-(dimethylamino)pyrrolidin-1-yl)benzaldehyde 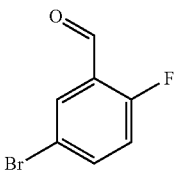 | | 298 | 5-bromo-2-fluorobenzaldehyde 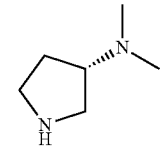 And (S)-N,N-dimethylpyrrolidin-3-amine |

| Method | Compound | ¹H NMR | m/z | SM |
|--------|----------|--------|-----|-----|
| 111 | (S)-2-(3-(dimethylamino)pyrrolidin-1-yl)-3-fluorobenzaldehyde  | | 237 | 2,3-difluorobenzaldehyde 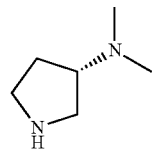<br>And<br>(S)-N,N-dimethylpyrrolidin-3-amine |
| 112 | (S)-2-chloro-6-(3-(dimethylamino)pyrrolidin-1-yl)benzaldehyde 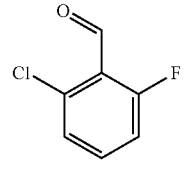 | | 253 | 2-chloro-6-fluorobenzaldehyde 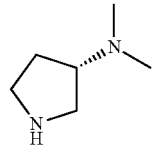<br>And<br>(S)-N,N-dimethylpyrrolidin-3-amine |
| 113 | (R)-tert-butyl 1-(2-formyl-6-isopropoxyphenyl)piperidin-3-ylcarbamate 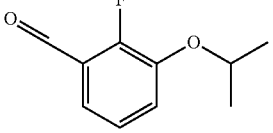 | | 363 | 2-fluoro-3-isopropoxybenzaldehyde Method 176 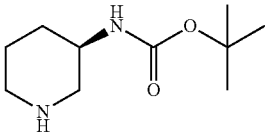<br>(R)-tert-butyl piperidin-3-ylcarbamate |

-continued

| Method | Compound | ¹H NMR | m/z | SM |
|---|---|---|---|---|
| 114 | (S)-tert-butyl 1-(2-formyl-6-isopropoxyphenyl)pyrrolidin-3-ylcarbamate 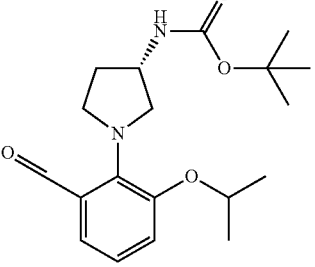 | | 349 | 2-fluoro-3-isopropoxybenzaldehyde Method 176 <br><br>(S)-tert-butyl pyrrolidin-3-ylcarbamate 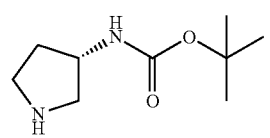 |
| 115 | (S)-tert-butyl 1-(2-ethoxy-6-formylphenyl)pyrrolidin-3-ylcarbamate 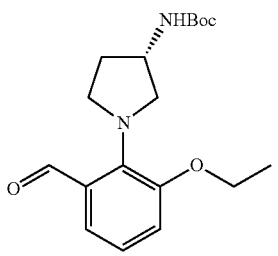 | | 334 | 3-ethoxy-2-fluorobenzaldehyde Method 172 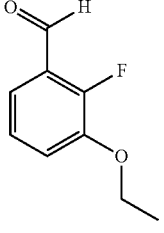<br><br>And (S)-tert-butyl pyrrolidin-3-ylcarbamate 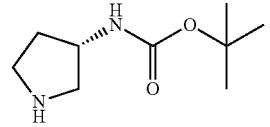 |
| 116 | 2-(3-(dimethylamino)pyrrolidin-1-yl)-5-nitrobenzaldehyde 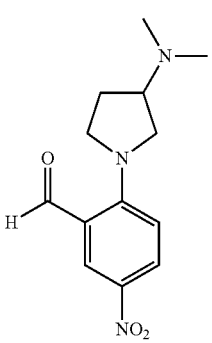 | | 263 | 2-fluoro-5-nitrobenzaldehyde 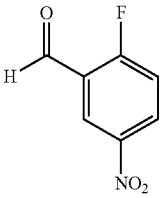<br><br>and N,N-dimethylpyrrolidin-3-amine 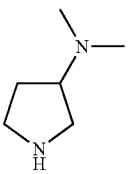 |

-continued

| Method | Compound | ¹H NMR | m/z | SM |
|---|---|---|---|---|
| 117 | (±)-tert-butyl-1-(2-chloro-6-formylphenyl)-4-hydroxypyrrolidin-3-ylcarbamate 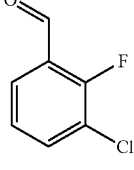 | 10.30 (s, 1 H) 7.76 (dd, 1 H) 7.65 (dd, 1 H) 7.29-7.24 (m, 1 H) 5.05 (brs, 1 H) 4.41 (brs, 1 H) 4.20 (brs, 1 H) 3.87 (dd, 1 H) 3.78 (dd, 1 H) 3.64-3.47 (m, 1 H) 3.36 (brs, 1 H) 3.21 (dd, 1 H) 1.50 (s, 9 H) | 341 | 3-chloro-2-fluorobenzaldehyde 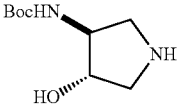 And (±)-tert-butyl-4-hydroxypyrrolidin-3-ylcarbamate Method 188 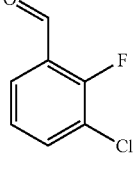 |
| 118 | tert-butyl-1-(2-chloro-6-formylphenyl)-4-methylpiperidin-3-yl(methyl)carbamate 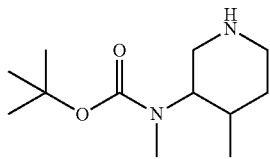 | | 367 | 3-chloro-2-fluorobenzaldehyde 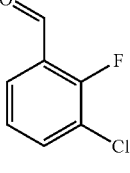 tert-butyl methyl(4-methylpiperidin-3-yl)carbamate 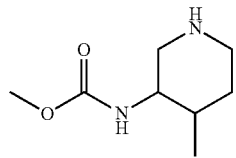 |
| 119 | methyl 1-(2-chloro-6-formylphenyl)-4-methylpiperidin-3-ylcarbamate | | 310 | 3-chloro-2-fluorobenzaldehyde methyl 4-methylpiperidin-3-ylcarbamate |

| Method | Compound | ¹H NMR | m/z | SM |
|---|---|---|---|---|
| 120 | (R)-tert-butyl 1-(2-formylphenyl)piperidin-3-ylcarbamate 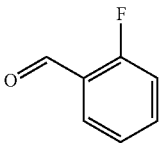 | | 305 | 2-fluorobenzaldehyde 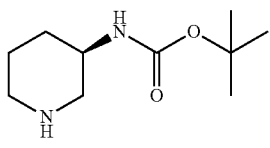<br>And<br>(R)-tert-butyl piperidin-3-ylcarbamate |
| 121 | (S)-tert-butyl 1-(2-formylphenyl)pyrrolidin-3-ylcarbamate 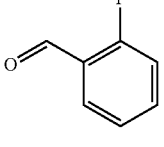 | | 291 | 2-fluorobenzaldehyde 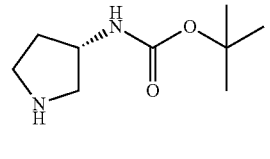<br>And<br>(S)-tert-butyl pyrrolidin-3-ylcarbamate |
| 122 | (R)-tert-butyl 1-(2-formyl-6-(2,2,2-trifluoroethoxy)phenyl)piperidin-3-ylcarbamate 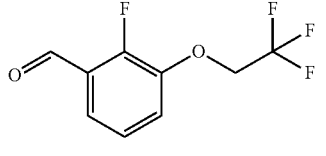 | | 403 | 2-fluoro-3-(2,2,2-trifluoroethoxy)benzaldehyde Method 177 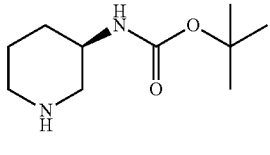<br>And<br>(R)-tert-butyl piperidin-3-ylcarbamate |

| Method | Compound | ¹H NMR | m/z | SM |
|---|---|---|---|---|
| 123 | (S)-tert-butyl 1-(2-formyl-6-(2,2,2-trifluoroethoxy)phenyl)pyrrolidin-3-ylcarbamate | | 389 | 2-fluoro-3-(2,2,2-trifluoroethoxy)benzaldehyde Method 177<br>And<br>(S)-tert-butyl pyrrolidin-3-ylcarbamate |
| 124 | (R)-tert-butyl 1-(2-formyl-6-(2-methoxyethoxy)phenyl)piperidin-3-ylcarbamate | | 379 | 2-fluoro-3-(2-methoxyethoxy)benzaldehyde Method 178<br>and<br>And<br>(R)-tert-butyl piperidin-3-ylcarbamate |
| 125 | (S)-tert-butyl 1-(2-formyl-6-(2-methoxyethoxy)phenyl)pyrrolidin-3-ylcarbamate | | 365 | 2-fluoro-3-(2-methoxyethoxy)benzaldehyde Method 178<br>And<br>(S)-tert-butyl pyrrolidin-3-ylcarbamate |

| Method | Compound | ¹H NMR | m/z | SM |
|---|---|---|---|---|
| 126 | (R)-tert-butyl 1-(2-(cyclopentyloxy)-6-formylphenyl)piperidin-3-ylcarbamate 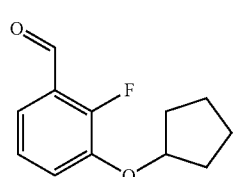 | | 389 | 3-(cyclopentyloxy)-2-fluorobenzaldehyde Method 179 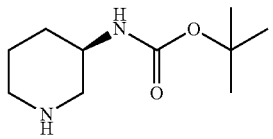 And (R)-tert-butyl piperidin-3-ylcarbamate |
| 127 | (R)-tert-butyl 1-(2-cyclobutoxy-6-formylphenyl)piperidin-3-ylcarbamate 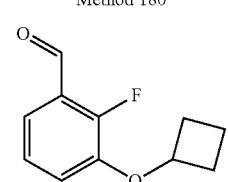 | | 375 | 3-cyclobutoxy-2-fluorobenzaldehyde Method 180 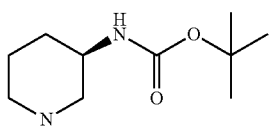 And (R)-tert-butyl piperidin-3-ylcarbamate |
| 128 | (R)-tert-butyl 1-(4-carbamoyl-2-formylphenyl)piperidin-3-ylcarbamate 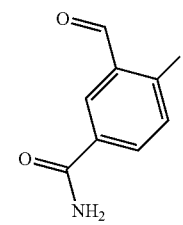 | | 348 | 4-fluoro-3-formylbenzamide 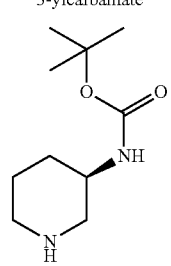 And (R)-tert-butyl piperidin-3-ylcarbamate |

| Method | Compound | ¹H NMR | m/z | SM |
|---|---|---|---|---|
| 129 | (S)-tert-butyl 1-(4-carbamoyl-2-formylphenyl)piperidin-3-ylcarbamate 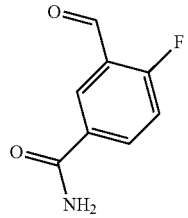 | | 348 | 4-fluoro-3-formylbenzamide 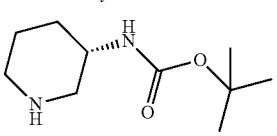 And (S)-tert-butyl piperidin-3-ylcarbamate |
| 130 | (R)-4-(3-(tert-butoxycarbonylamino)piperidin-1-yl)-3-formylbenzoic acid 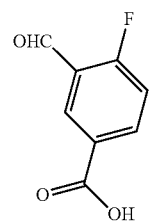 | | 348 | 4-fluoro-3-formylbenzoic acid 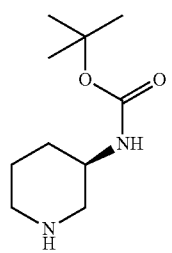 And (R)-tert-butyl piperidin-3-ylcarbamate |
| 131 | (S)-4-(3-(tert-butoxycarbonylamino)pyrrolidin-1-yl)-3-formylbenzoic acid 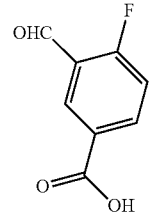 | | 334 | 4-fluoro-3-formylbenzoic acid 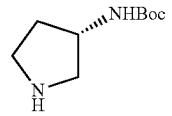 And (S)-tert-butyl pyrrolidin-3-ylcarbamate |

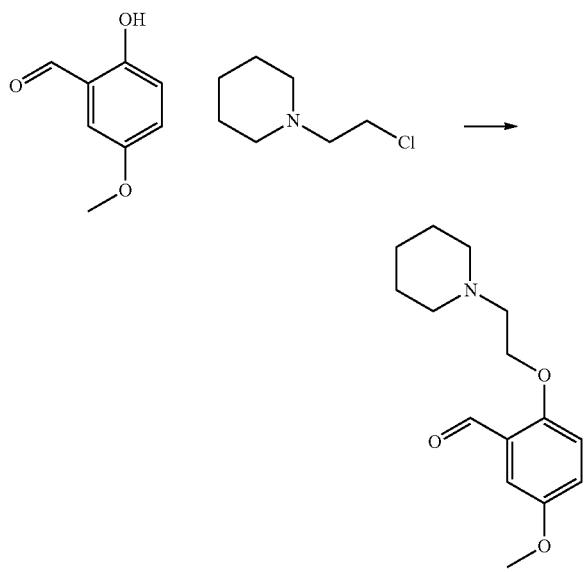

Method 27:

5-methoxy-2-(2-(piperidin-1-yl)ethoxy)benzaldehyde

A mixture of 2-hydroxy-5-methoxybenzaldehyde (0.761 g, 5 mmol), 1-(2-chloroethyl)piperidine hydrochloride (0.921 g, 5.00 mmol), $K_2CO_3$ (2.07 g, 14.99 mmol), and sodium iodide (0.075 g, 0.50 mmol) in acetonitrile (40 mL) was stirred at 100° C. overnight. The reaction was allowed to cool to ambient temperature and sat'd aqueous $K_2CO_3$ was added to the reaction mixture. The mixture was poured into a separatory funnel and extracted with EtOAc. The organic phase was dried over anhydrous $MgSO_4$, filtered through a bed of Celite, and conc. in vacuo to yield the product which was purified via silica gel chromatography (80 g) using EtOAc/hexanes (4:1) as eluent to yield the title compound as a brown oil (0.551 g, 42%); m/z 264.

The following intermediates were prepared by the procedure of Method 27, using the appropriate starting materials.

| Method | Compound | $^1$H NMR | m/z | SM |
|---|---|---|---|---|
| 28 | 5-methoxy-2-(2-morpholinoethoxy)benzaldehyde | | 266 | 2-hydroxy-5-methoxybenzaldehyde and 4-(2-chloroethyl)morpholine hydrochloride |
| 29 | 2-(2-(diethylamino)ethoxy)-5-methoxybenzaldehyde | | 252 | 2-hydroxy-5-methoxybenzaldehyde and 2-chloro-N,N-diethylethanamine |

-continued

| Method | Compound | ¹H NMR | m/z | SM |
|---|---|---|---|---|
| 30A | 2-(2-(diethylamino)ethoxy)benzaldehyde | | 222 | Salicylaldehyde and 2-chloro-N,N-diethylethanamine |
| 30B | 2-(3-(1,3-dioxoisoindolin-2-yl)propoxy)-5-methoxybenzaldehyde | 10.18 (s, 1 H) 7.69 (m, 4 H) 7.11 (m, 2 H) 6.97 (d, 1 H) 4.05 (m, 2 H) 3.83 (m, 2 H) 3.67 (s, 3 H) 2.12 (m, 2 H) | 340 | 2-hydroxy-5-methoxybenzaldehyde and 2-(3-bromopropyl)isoindoline-1,3-dione |

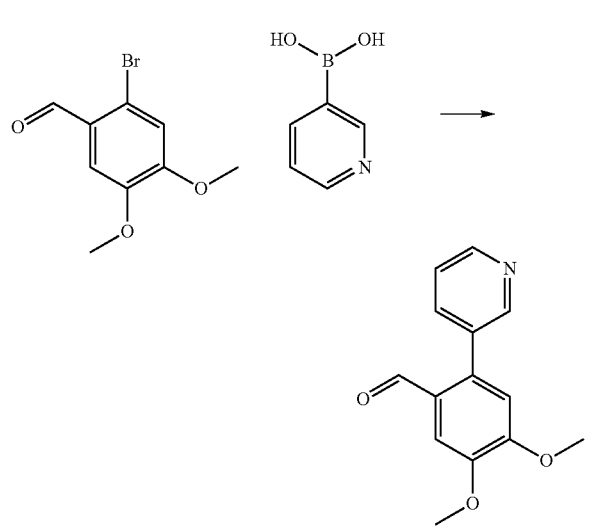

Method 31:

4,5-dimethoxy-2-(pyridin-3-yl)benzaldehyde

A mixture of 2-bromo-4,5-dimethoxybenzaldehyde (0.368 g, 1.5 mmol), pyridin-3-ylboronic acid (0.246 g, 2.0 mmol), Pd(PPh$_3$)$_4$ (0.173 g, 0.150 mmol), and cesium carbonate (0.977 g, 3 mmol) were suspended in dioxane (4 mL) and water (1 mL). The mixture was heated to 140° C. in a microwave for 1 h. The reaction vessel was allowed to cool to ambient temperature, diluted with ethyl acetate (~25 mL), filtered through a bed of Celite, and conc. in vacuo to afford the aldehyde which was purified via SiO$_2$ chromatography (40 g) using ethyl acetate/hexanes (5:1) as eluent to afford the title compound as a white solid (0.340 g, 93%); m/z 244.

The following intermediates were prepared by the procedure of Method 31, using the appropriate starting materials.

| Method | Compound | ¹H NMR | m/z | SM |
|---|---|---|---|---|
| 32A | 4,5-dimethoxy-2-(pyridin-4-yl)benzaldehyde 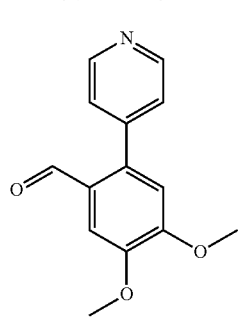 [SMILES: COc1cc(C=O)c(-c2ccncc2)cc1OC] | | 244 | 2-bromo-4,5-dimethoxybenzaldehyde 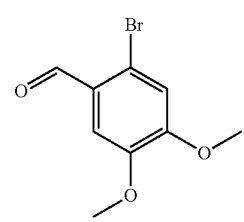 and pyridin-4-ylboronic acid 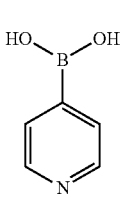 |
| 32B | N-(2-(dimethylamino)ethyl)-2'-formyl-N-methylbiphenyl-4-sulfonamide 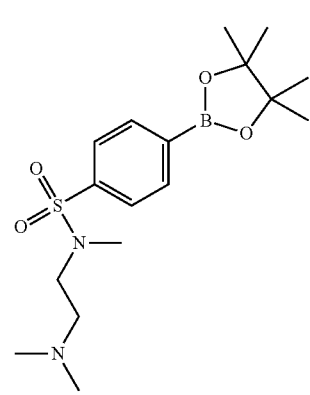 | 9.95 (s, 1 H), 8.05 (d, 1 H), 7.96 (d, 2 H), 7.72-7.83 (m, 1 H), 7.57-7.72 (m, 3 H), 7.53 (d, 1 H), 3.24 (t, 2 H), 2.79-2.91 (m, 3 H), 2.65 (t, 2 H), 2.37 (s, 6 H) | 346 | N-(2-(dimethylamino)ethyl)-N-methyl-4-(4,4,5,5,-tetramethyl-1,3,2-dioxaborolan-2-yl)benzenesulfonamide 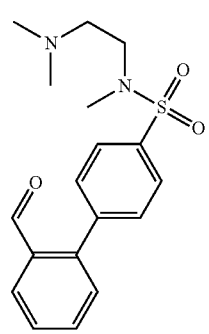 And 2-bromobenzaldehyde 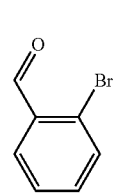 |
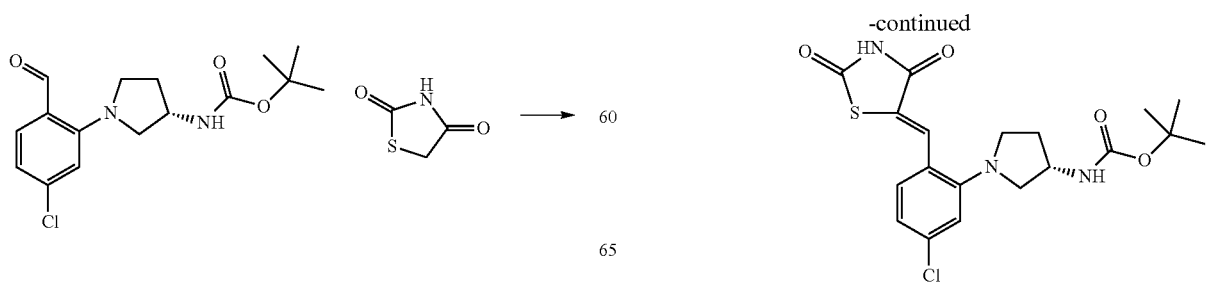

Method 33:

(S,Z)-tert-butyl 1-(5-chloro-2-((2,4-dioxothiazolidin-5-ylidene)methyl)phenyl)pyrrolidin-3-ylcarbamate A 100 mL round bottom flask was charged with a magnetic stir bar, (S)-tert-butyl 1-(5-chloro-2-formylphenyl)pyrrolidin-3-ylcarbamate (Method 78) (1.100 g, 3.39 mmol), thiazolidine-2,4-dione (0.397 g, 3.39 mmol), and ethanol (11.29 ml). Piperidine (0.034 mL, 0.34 mmol) was added and the reaction was heated to reflux for 2 h. Once the reaction was judged to be complete by LCMS, it was allowed to cool to ambient temperature and conc. in vacuo to afford the title compound (1.310 g, 91%) which was used in the next step without further purification; m/z 425.

The following intermediates were prepared by the procedure of Method 33, using the appropriate starting materials.

| Method | Compound | ¹H NMR | m/z | SM |
|---|---|---|---|---|
| 34 | (S,Z)-tert-butyl 1-(2-chloro-6-((2,4-dioxothiazolidin-5-ylidene)methyl)phenyl)pyrrolidin-3-ylcarbamate | | 425 | tert-butyl [(3S)-1-(2-chloro-6-formylphenyl)pyrrolidin-3-yl]carbamate Method 79 |
| 35 | (Z)-tert-butyl 4-(2-((2,4-dioxothiazolidin-5-ylidene)methyl)-4-(trifluoromethyl)phenyl)piperazine-1-carboxylate | | 459 | tert-butyl 4-[2-formyl-4-(trifluoromethyl)phenyl]piperazine-1-carboxylate Method 80 |
| 36 | (S,Z)-tert-butyl 1-(2-((2,4-dioxothiazolidin-5-ylidene)methyl)-4-(trifluoromethyl)phenyl)pyrrolidin-3-ylcarbamate | | 459 | tert-butyl{3S-1-[2-formyl-4-(trifluoromethyl)phenyl]pyrrolidin-3-yl}carbamate Method 81 |

| Method | Compound | ¹H NMR | m/z | SM |
|---|---|---|---|---|
| 37 | (Z)-tert-butyl 4-(3-((2,4-dioxothiazolidin-5-ylidene)methyl)pyridin-2-yl)piperazine-1-carboxylate | | 391 | tert-butyl 4-(3-formylpyridin-2-yl)piperazine-1-carboxylate Method 82 |
| 44 | (S,Z)-tert-butyl 1-(2-((2,4-dioxothiazolidin-5-ylidene)methyl)-6-methoxyphenyl)pyrrolidin-3-ylcarbamate | | | tert-butyl [(3S)-1-(2-formyl-6-methoxyphenyl)pyrrolidin-3-yl]carbamate Method 83 |
| 45 | (Z)-tert-butyl 4-(2-((2,4-dioxothiazolidin-5-ylidene)methyl)-6-methoxyphenyl)piperazin-1-carboxamide | | 421 | tert-butyl 4-(2-formyl-6-methoxyphenyl)piperazine-1-carboxylate Method 85 |
| 46 | (Z)-tert-butyl 4-(2-chloro-6-((2,4-dioxothiazolidin-5-ylidene)methyl)phenyl)piperazine-1-carboxylate | | 425 | tert-butyl 4-(2-chloro-6-formylphenyl)piperazine-1-carboxylate Method 85 |

-continued

| Method | Compound | ¹H NMR | m/z | SM |
|---|---|---|---|---|
| 47 | (Z)-tert-butyl (1-(2-((2,4-dioxothiazolidin-5-ylidene)methyl)-4,5-dimethoxyphenyl)pyrrolidin-3-yl)methylcarbamate | | 465 | tert-butyl (1-(2-formyl-4,5-dimethoxyphenyl)pyrrolidin-3-yl)methylcarbamate Method 86 |
| 48 | (R,Z)-tert-butyl 1-(2-((2,4-dioxothiazolidin-5-ylidene)methyl)-4,5-dimethoxyphenyl)pyrrolidin-3-ylcarbamate | | 451 | (R)-tert-butyl 1-(2-formyl-4,5-dimethoxyphenyl)pyrrolidin-3-ylcarbamate Method 87 |
| 49 | (S,Z)-tert-butyl 1-(2-((2,4-dioxothiazolidin-5-ylidene)methyl)-4,5-dimethoxyphenyl)pyrrolidin-3-ylcarbamate | | 451 | (S)-tert-butyl 1-(2-fomryl-4,5-dimethoxy)phenyl)pyrrolidin-3-ylcarbamate Method 88 |

| Method | Compound | ¹H NMR | m/z | SM |
|---|---|---|---|---|
| 54 | (Z)-tert-butyl 4-(2-((2,4-dioxothiazolidin-5-ylidene)methyl)phenyl)-1,4-diazepane-1-carboxylate | | 404 | tert-butyl 4-(2-formylphenyl)-1,4-diazepane-1-carboxylate Method 89 |
| 65 | tert-butyl 1-(2-((2,4-dioxothiazolidin-5-ylidene)methyl)-4,5-dimethoxyphenyl)pyrrolidin-3-ylcarbamate | | 451 | tert-butyl 1-(2-formyl-4,5-dimethoxyphenyl)pyrrolidin-3-ylcarbamate Method 90 |
| 132 | (R,Z)-tert-butyl (1-(2-chloro-6-((2,4-dioxothiazolidin-5-ylidene)methyl)phenyl)pyrrolidin-3-yl)methylcarbamate | | 439 | (R)-tert-butyl 1-(2-chloro-6-formylphenyl)pyrrolidin-3-yl)methylcarbamate Method 91 |

-continued

| Method | Compound | ¹H NMR | m/z | SM |
|---|---|---|---|---|
| 133 | (S,Z)-tert-butyl (1-(2-chloro-6-((2,4-dioxothiazolidin-5-ylidene)methyl)phenyl)pyrrolidin-3-yl)methylcarbamate | | 439 | (S)-tert-butyl (1-(2-chloro-6-formylphenyl)pyrrolidin-3-yl)methylcarbamate Method 92 |
| 134 | (R,Z)-tert-butyl 1-(2-chloro-6-((2,4-dioxothiazolidin-5-ylidene)methyl)phenyl)piperidin-3-ylcarbamate | | 438 | (R)-tert-butyl 1-(2-chloro-6-formylphenyl)piperidin-3-ylcarbamate Method 93 |
| 135 | (R,Z)-tert-butyl 1-(2-((2,4-dioxothiazolidin-5-ylidene)methyl)-6-methoxyphenyl)piperidin-3-ylcarbamate | | 434 | (R)-tert-butyl 1-(2-formyl-6-methoxyphenyl)piperidin-3-ylcarbamate Method 94 |
| 136 | (R,Z)-tert-butyl 1-(2-bromo-6-((2,4-dioxothiazolidin-5-ylidene)methyl)phenyl)piperidin-3-ylcarbamate | | 484 | (R)-tert-butyl 1-(2-bromo-6-formylphenyl)piperidin-3-ylcarbamate Method 95 |

| Method | Compound | ¹H NMR | m/z | SM |
|---|---|---|---|---|
| 137 | (R,Z)-tert-butyl 1-(2-chloro-6-((2,4-dioxothiazolidin-5-ylidene)methyl)phenyl)pyrrolidin-3-ylcarbamate | | 424 | (R)-tert-butyl 1-(2-chloro-6-formylphenyl)pyrrolidin-3-ylcarbamate Method 96 |
| 138 | (S,Z)-tert-butyl 1-(2-bromo-6-((2,4-dioxothiazolidin-5-ylidene)methyl)phenyl)pyrrolidin-3-ylcarbamate | | 470 | (S)-tert-butyl 1-(2-bromo-6-formylphenyl)pyrrolidin-3-ylcarbamate Method 97 |
| 139 | (R,Z)-tert-butyl 1-(2-((2,4-dioxothiazolidin-5-ylidene)methyl)-6-ethoxyphenyl)piperidin-3-ylcarbamate | | 448 | (R)-tert-butyl 1-(2-ethoxy-6-formylphenyl)piperidin-3-ylcarbamate Method 98 |
| 140 | (R,Z)-tert-butyl 1-(2-((2,4-dioxothiazolidin-5-ylidene)methyl)-6-isobutoxyphenyl)piperidin-3-ylcarbamate | | 476 | (R)-tert-butyl 1-(2-formyl-6-isobutoxyphenyl)piperidin-3-ylcarbamate Method 99 |

| Method | Compound | ¹H NMR | m/z | SM |
|--------|----------|--------|-----|-----|
| 141 | (R,Z)-tert-butyl 1-(2-(cyclohexylmethoxy)-6-((2,4-dioxothiazolidin-5-ylidene)methyl)phenyl)piperidin-3-ylcarbamate 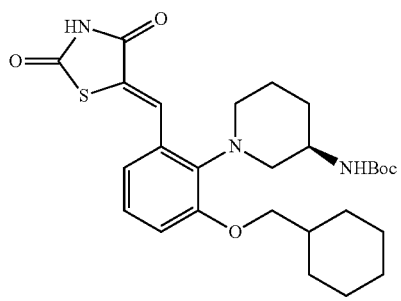 | | 516 | (R)-tert-butyl 1-(2-(cyclohexylmethoxy)-6-formylphenyl)piperidin-3-ylcarbamate Method 100 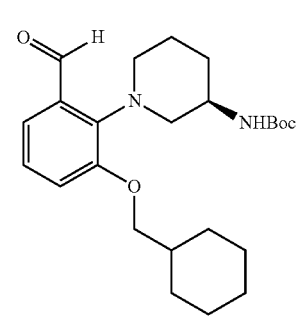 |
| 142 | (R,Z)-tert-butyl 1-(2-(cyclohexyloxy)-6-((2,4-dioxothiazolidin-5-ylidene)methyl)phenyl)piperidin-3-ylcarbamate 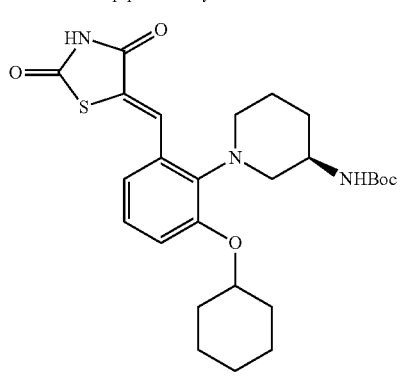 | | 501 | (R)-tert-butyl 1-(2-(cyclohexyloxy)-6-formylphenyl)piperidin-3-ylcarbamate Method 101 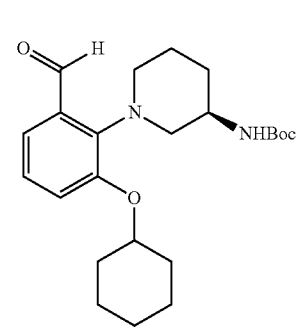 |
| 143 | (±)-tert-butyl-1-(2-chloro-6-((Z)-(2,4-dioxothiazolidin-5-ylidene)methyl)phenyl)-4-hydroxypiperidin-3-ylcarbamate 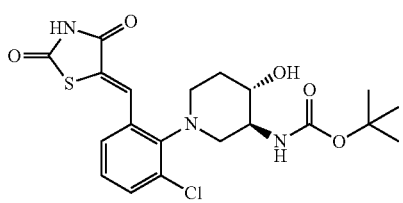 | | 454 | (±)-tert-butyl-1-(2-chloro-6-formylphenyl)-4-hydroxypiperidin-3-ylcarbamate Method 102 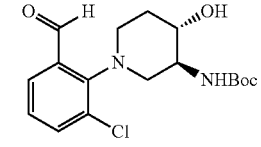 |

-continued

| Method | Compound | ¹H NMR | m/z | SM |
|---|---|---|---|---|
| 144 | (Z)-tert-butyl 4-(2-chloro-6-((2,4-dioxothiazolidin-5-ylidene)methyl)phenyl)-1,4-diazepane-1-carboxylate | 8.66 (brs, 1 H), 8.36 (brs, 1 H), 7.47 (d, 1 H), 7.39 (d, 1 H), 7.22 (t, 1 H), 3.61 (brs, 3 H), 3.52 (brs, 2 H), 3.27 (brs, 3 H), 1.91 (brs, 2 H), 1.52 (s, 9 H) | 438 | tert-butyl 4-(2-chloro-6-formylphenyl)-1,4-diazepane-1-carboxylate Method 103 |
| 145 | (R,Z)-tert-butyl 1-(2-((2,4-dioxothiazolidin-5-ylidene)methyl)-6-isopropoxyphenyl)piperidin-3-ylcarbamate | | 462 | (R)-tert-butyl 1-(2-formyl-6-iosopropoxyphenyl)piperidin-3-ylcarbamate Method 113 |
| 146 | (S,Z)-tert-butyl 1-(2-((2,4-dioxothiazolidin-5-ylidene)methyl)-6-isopropoxyphenyl) pyrrolidin-3-ylcarbamate | | 448 | (S)-tert-butyl 1-(2-formyl-6-isopropoxyphenyl) pyrrolidin-3-ylcarbamate Method 114 |

| Method | Compound | ¹H NMR | m/z | SM |
|---|---|---|---|---|
| 147 | (S,Z)-tert-butyl 1-(2-((2,4-dioxothiazolidin-5-ylidene)methyl)-6-ethoxyphenyl)pyrrolidin-3-ylcarbamate | | 334 | (S)-tert-butyl 1-(2-ethoxy-6-formylphenyl)pyrrolidin-3-ylcarbamate Method 115 |
| 148 | 5-(2-(3-(1,3-dioxoisoindolin-2-yl)propoxy)-5-methoxybenzylidene)thiazolidine-2,4-dione | 12.54 (s, 1 H) 7.83-7.79 (m, 5 H) 7.04 (s, 2 H) 6.86 (s, 1 H) 4.08 (m, 2 H) 3.80-3.75 (m, 5 H) 2.11 (m, 2 H) | 438 | 2-(3-(1,3-dioxoisoindolin-2-yl)propoxy)-5-methoxybenzaldehyde Method 30B |
| 149 | 5-(2-(3-(dimethylamino)pyrrolidin-1-yl)-5-nitrobenzylidene)thiazolidine-2,4-dione | 8.20 (s, 1 H) 8.07 (d, 1 H) 7.82 (s, 1 H) 6.96 (d, 1 H) 3.58-3.51 (m, 3 H) 3.36 (m, 1 H) 3.04 (m, 1 H) 2.51 (s, 6 H), 2.40 (m, 1 H), 1.86 (m, 1 H) | 363 | 2-(3-(dimethylamino)pyrrolidin-1-yl)-5-nitrobenzaldehyde Method 116 |

-continued

| Method | Compound | ¹H NMR | m/z | SM |
|---|---|---|---|---|
| 150 | (Z)-5-(4,5-dimethoxy-2-nitrobenzylidene)thiazolidine-2,4-dione 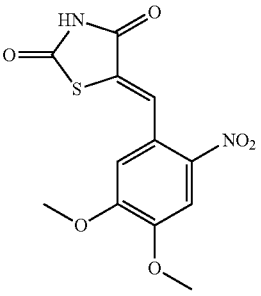 | 8.32 (s, 1 H) 8.25 (brs, 1 H) 7.79 (s, 1 H) 7.02 (s, 1 H) 4.03 (s, 6 H) | 309 | 4,5-dimethoxy-2-nitrobenzaldehyde 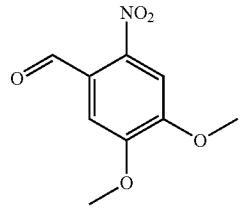 |
| 151 | tert-butyl (3S,4S)-1-(2-chloro-6-((Z)-(2,4-dioxothiazolidin-5-ylidene)methyl)phenyl)-4-hydroxypyrrolidin-3-ylcarbamate 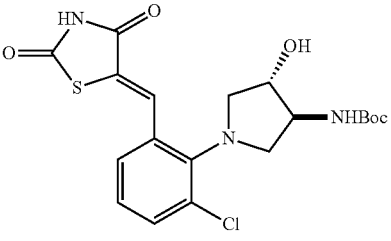 | 8.30 (s, 1 H) 7.49 (d, 1 H) 7.42 (d, 1 H) 7.28-7.20 (m, 1 H) 5.01 (d, 1 H) 4.39 (brs, 1 H) 4.27 (brs, 1 H) 4.05 (s, 1 H) 3.83 (dd, 1 H) 3.69 (dd, 1 H) 3.27 (brs, 1 H) 3.19 (dd, 1 H), 1.50 (s, 9 H) | 439 | tert-butyl (3S,4S)-1-(2-chloro-6-formylphenyl)-4-hydroxypyrrolidin-3-ylcarbamate Method 117 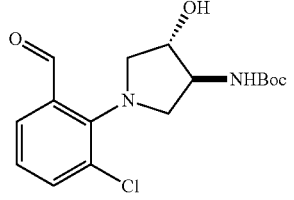 |
| 152 | (Z)-tert-butyl 1-(2-chloro-6-((2,4-dioxothiazolidin-5-ylidene)methyl)phenyl)-4-methylpiperidin-3-yl(methyl)carbamate 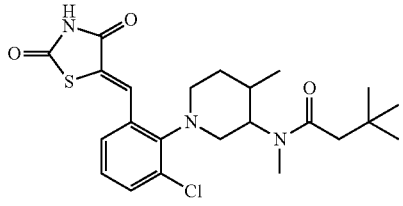 | | 465 | tert-butyl 1-(2-chloro-6-formylphenyl)-4-methylpiperidin-3-yl(methyl)carbamate Method 118 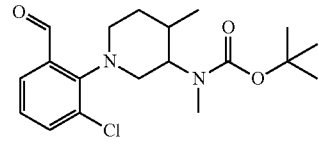 |
| 153 | (Z)-tert-butyl 1-(2-chloro-6-((2,4-dioxothiazolidin-5-ylidene)methyl)phenyl)-4-methylpiperidin-3-ylcarbamate 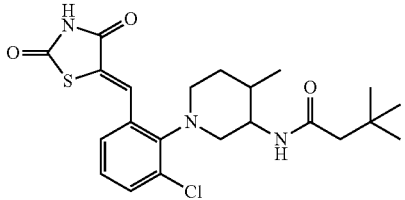 | | 451 | tert-butyl 1-(2-chloro-6-formylphenyl)-4-methylpiperidin-3-ylcarbamate Method 119 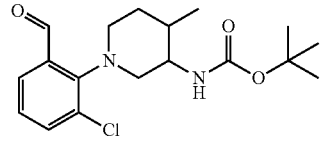 |

-continued

| Method | Compound | ¹H NMR | m/z | SM |
|---|---|---|---|---|
| 154 | (R,Z)-tert-butyl 1-(2-((2,4-dioxothiazolidin-5-ylidene)methyl)phenyl)piperidin-3-ylcarbamate | | 404 | (R)-tert-butyl 1-(2-formylphenyl)piperidin-3-ylcarbamate Method 120 |
| 155 | (S,Z)-tert-butyl 1-(2-((2,4-dioxothiazolidin-5-ylidene)methyl)phenyl)pyrrolidin-3-ylcarbamate | | 390 | (S)-tert-butyl 1-(2-formylphenyl)pyrrolidin-3-ylcarbamate Method 121 |
| 156 | (R,Z)-tert-butyl 1-(2-((2,4-dioxothiazolidin-5-ylidene)methyl)-6-(2,2,2-trifluoroethoxy)phenyl)piperidin-3-ylcarbamate | | 502 | (R)-tert-butyl 1-(2-formyl-6-(2,2,2-trifluoroethoxy)phenyl)piperidin-3-ylcarbamate Method 122 |
| 157 | (S,Z)-tert-butyl 1-(2-((2,4-dioxothiazolidin-5-ylidene)methyl)-6-(2,2,2-trifluoroethoxy)phenyl)pyrrolidin-3-ylcarbamate | | 488 | (S)-tert-butyl 1-(2-formyl-6-(2,2,2-trifluoroethoxy)phenyl)pyrrolidin-3-ylcarbamate Method 123 |

| Method | Compound | ¹H NMR | m/z | SM |
|---|---|---|---|---|
| 158 | (R,Z)-tert-butyl 1-(2-((2,4-dioxothiazolidin-5-ylidene)methyl)-6-(2-methoxyethoxy)phenyl)piperidin-3-ylcarbamate | | 478 | (R)-tert-butyl 1-(2-formyl-6-(2-methoxyethoxy)phenyl)piperidin-3-ylcarbamate Method 124 |
| 159 | (S,Z)-tert-butyl 1-(2-((2,4-dioxothiazolidin-5-ylidene)methyl)-6-(2-methoxyethoxy)phenyl)pyrrolidin-3-ylcarbamate | | 464 | (S)-tert-butyl 1-(2-formyl-6-(2-methoxyethoxy)phenyl)pyrrolidin-3-ylcarbamate Method 125 |
| 160 | (R,Z)-tert-butyl 1-(2-(cyclopentyloxy)-6-((2,4-dioxothiazolidin-5-ylidene)methyl)phenyl)piperidin-3-ylcarbamate | | 488 | (R)-tert-butyl 1-(2-(cyclopentyloxy)-6-formylphenyl)piperidin-3-ylcarbamate Method 126 |

| Method | Compound | ¹H NMR | m/z | SM |
|---|---|---|---|---|
| 161 | (R,Z)-tert-butyl 1-(2-cyclobutoxy-6-((2,4-dioxothiazolidin-5-ylidene)methyl)phenyl)piperidin-3-ylcarbamate | | 474 | (R)-tert-butyl 1-(2-cyclobutoxy-6-formylphenyl)piperidin-3-ylcarbamate Method 127 |
| 162 | (R,Z)-tert-butyl 1-(4-carbamoyl-2-((2,4-dioxothiazolidin-5-ylidene)methyl)phenyl)piperidin-3-ylcarbamate | | 447 | (R)-tert-butyl 1-(4-carbamoyl-2-formylphenyl)piperidin-3-ylcarbamate Method 128 |
| 163 | (S,Z)-tert-butyl 1-(4-carbamoyl-2-((2,4-dioxothiazolidin-5-ylidene)methyl)phenyl)piperidin-3-ylcarbamate | | 447 | (S)-tert-butyl 1-(4-carbamoyl-2-formylphenyl)piperidin-3-ylcarbamate Method 129 |

| Method | Compound | ¹H NMR | m/z | SM |
|---|---|---|---|---|
| 164 | (R,Z)-4-(3-(tert-butoxycarbonylamino)piperidin-1-yl)-3-((2,4-dioxothiazolidin-5-ylidene)methyl)benzoic acid | | 447 | (R)-4-(3-(tert-butoxycarbonylamino)piperidin-1-yl)-3-formylbenzoic acid Method 130 |
| 165 | (S,Z)-4-(3-(tert-butoxycarbonylamino)pyrrolidin-1-yl)-3-((2,4-dioxothiazolidin-5-ylidene)methyl)benzoic acid | | 433 | (S)-4-(3-(tert-butoxycarbonylamino)pyrrolidin-1-yl)-3-formylbenzoic acid Method 131 |
| 166 | (R,Z)-tert-butyl 1-(3-((2,4-dioxothiazolidin-5-ylidene)methyl)biphenyl-2-yl)piperidin-3-ylcarbamate | | 480 | (R)-tert-butyl 1-(3-formylbiphenyl-2-yl)piperidin-3-ylcarbamate Method 201 |

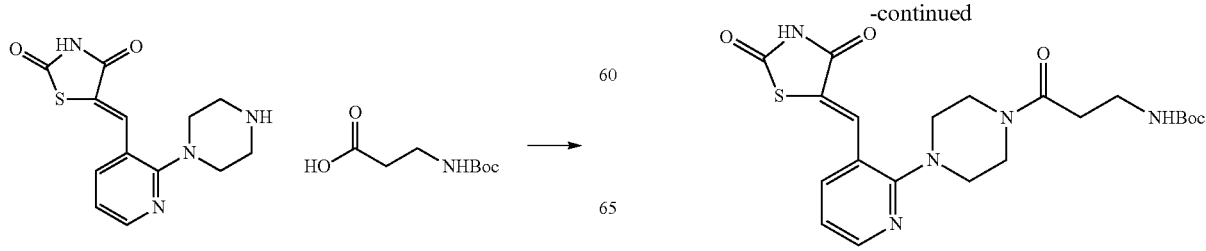

Method 38:

(Z)-tert-butyl 3-(4-(3-((2,4-dioxothiazolidin-5-ylidene)methyl)pyridin-2-yl)piperazin-1-yl)-3-oxopropylcarbamate A 50 mL vial was charged with a magnetic spin bar, (Z)-5-((2-(piperazin-1-yl)pyridin-3-yl)methylene)thiazolidine-2,4-dione hydrochloride (Example 89) (0.125 g, 0.38 mmol), 3-(tert-butoxycarbonylamino)propanoic acid (0.109 g, 0.57 mmol), DMF (1.912 ml), and diisopropylethylamine (0.334 ml, 1.91 mmol). With stirring, HATU (0.291 g, 0.76 mmol) was added and the reaction was warmed to 50° C. for 3 h. The reaction was then diluted with water and extracted with ethyl acetate (3×50 mL). The combined organic extract was dried with $MgSO_4$, filtered through a bed of Celite, and conc. in vacuo to yield the product which was purified via silica gel chromatography (80 g) using ethyl acetate/hexanes (1:1) as eluent to provide the title compound as an off white solid. (0.080 g, 45.3%); m/z 462.

The following intermediates were prepared by the procedure of Method 38, using the appropriate starting materials.

| Method | Compound | $^1$H NMR | m/z | SM |
|---|---|---|---|---|
| 39 | (Z)-tert-butyl 4-(4-(2-((2,4-dioxothiazolidin-5-ylidene)methyl)phenyl)piperazine-1-carbonyl)piperidine-1-carboxylate 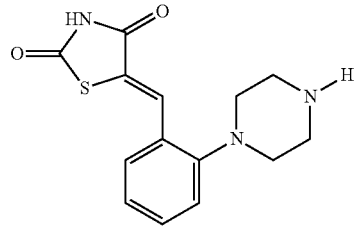 | | 502 | (5Z)-5-(2-piperazin-1-ylbenzylidene)-1,3-thiazolidine-2,4-dione 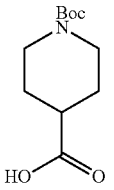 Example 115 and 1-(tert-butoxycarbonyl)piperidine-4-carboxylic acid |
| 40 | (Z)-tert-butyl 3-(4-(2-((2,4-dioxothiazolidin-5-ylidene)methyl)-4-(trifluoromethyl)phenyl)piperazine-1-carbonyl)piperidine-1-carboxylate 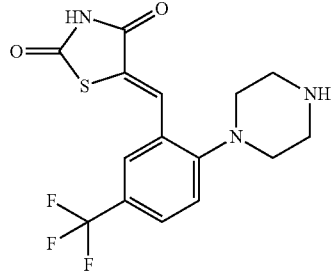 | | 560 | (Z)-5-(2-(piperazin-1-yl)-5-(trifluoromethyl)benzylidene)thiazolidine-2,4-dione 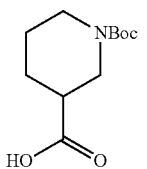 Example 87 and 1-(tert-butoxycarbonyl)piperidine-3-carboxylic acid |

-continued

| Method | Compound | ¹H NMR | m/z | SM |
|---|---|---|---|---|
| 41 | (Z)-tert-butyl 3-(4-(2-((2,4-dioxothiazolidin-5-ylidene)methyl)-4-(trifluoromethyl)phenyl)piperazin-1-yl)-3-oxopropylcarbamate | | 530 | (Z)-5-(2-(piperazin-1-yl)-5-(trifluoromethyl)benzylidene)thiazolidine-2,4-dione<br><br>Example 87 and 3-[(tert-butoxycarbonyl)amino]propanoic acid |
| 42 | (Z)-tert-butyl 3-(4-(2-((2,4-dioxothiazolidin-5-ylidene)methyl)-6-methoxyphenyl)piperazin-1-yl)-3-oxopropylcarbamate | | 492 | (Z)-5-(3-methoxy-2-(piperazin-1-yl)benzylidene)thiaozlidine-2,4-dione<br><br>Example 97 and 3-[(tert-butoxycarbonyl)amino]propanoic acid |
| 43 | (Z)-tert-butyl 3-(4-(2-chloro-6-((2,4-dioxothiazolidin-5-ylidene)methyl)phenyl)piperazin-1-yl)-3-oxopropylcarbamate | | 496 | (Z)-5-(3-chloro-2-(piperazin-1-yl)benzylidene)thiazolidine-2,4-dione<br><br>Example 98 and 3-[(tert-butoxycarbonyl)amino]propanoic acid |

| Method | Compound | ¹H NMR | m/z | SM |
|---|---|---|---|---|
| 50 | (Z)-tert-butyl 3-(4-(2-((2,4-dioxothiazolidin-5-ylidene)methyl)phenyl)-1,4-diazepane-1-carbonyl)piperidine-1-carboxylate | | 516 | (Z)-5-(2-(1,4-diazepan-1-yl)benzylidene)thiazolidine-2,4-dione<br><br>Example 106 and 1-(tert-butoxycarbonyl)piperidine-3-carboxylic acid |
| 51 | (Z)-tert-butyl 5-(4-(2-((2,4-dioxothiazolidin-5-ylidene)methyl)phenyl)-1,4-diazepan-1-yl)-5-oxopentylcarbamate | | 504 | (Z)-5-(2-(1,4-diazepan-1-yl)benzylidene)thiazolidine-2,4-dione<br><br>Example 106 and 5-[(tert-butoxycarbonyl)amino]pentaonic acid |

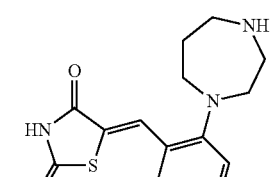

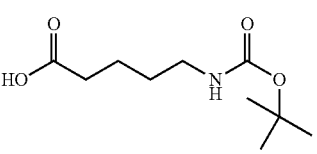

-continued

| Method | Compound | ¹H NMR | m/z | SM |
|---|---|---|---|---|
| 52 | (Z)-tert-butyl 4-(4-(2-((2,4-dioxothiazolidin-5-ylidene)methyl)phenyl)-1,4-diazepan-1-yl)-4-oxobutylcarbamate 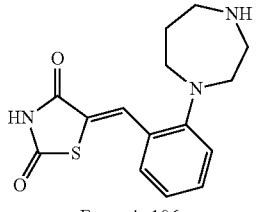 | | 490 | (Z)-5-(2-(1,4-diazepan-1-yl)benzylidene)thiazolidine-2,4-dione 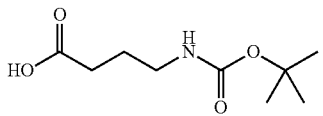<br>Example 106 and 4-[(tert-butoxycarbonyl)amino]butanoic acid |
| 53 | (Z)-tert-butyl 3-(4-(2-((2,4-dioxothiazolidin-5-ylidene)methyl)phenyl)-1,4-diazepan-1-yl)-3-carbamate 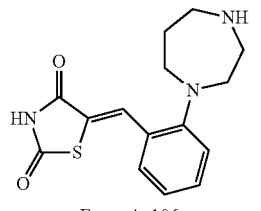 | | 475 | (Z)-5-(2-(1,4-diazepan-1-yl)benzylidene)thiazolidine-2,4-dione 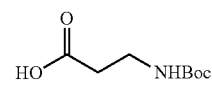<br>Example 106 and 3-[(tert-butoxycarbonyl)amino]propanoic acid |
| 55 | (Z)-tert-butyl 4-(4-(2-((2,4-dioxothiazolidin-5-ylidene)methyl)phenyl)piperazin-1-yl)-4-oxobutylcarbamate 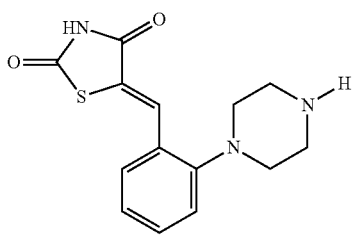 | | 476 | (5Z)-5-(2-piperazin-1-ylbenzylidene)-1,3-thiazolidine-2,4-dione 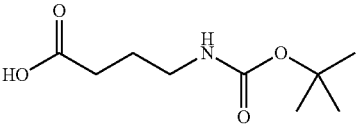<br>Example 115 and 4-[(tert-butoxycarbonyl)amino]butanoic acid |

| Method | Compound | ¹H NMR | m/z | SM |
|---|---|---|---|---|
| 56 | (Z)-tert-butyl 5-(4-(2-((2,4-dioxothiazolidin-5-ylidene)methyl)phenyl)piperazin-1-yl)-5-oxopentylcarbamate | | 490 | (5Z)-5-(2-piperazin-1-ylbenzylidene)-1,3-thiazolidine-2,4-dione<br><br>Example 115<br>and<br>nd<br>5-[(tert-butoxycarbonyl)amino]pentaonic acid |
| 57 | (Z)-tert-butyl 4-(4-(4-(2-((2,4-dioxothiazolidin-5-ylidene)methyl)phenyl)piperazine-1-carbonyl)benzyl)piperazine-1-carboxylate | | 593 | (5Z)-5-(2-piperazin-1-ylbenzylidene)-1,3-thiazolidine-2,4-dione<br><br>Example 115<br>and<br>4-{[4-(tert-butoxycarbonyl)piperazin-1-yl]methyl} benzoic acid |

-continued

| Method | Compound | ¹H NMR | m/z | SM |
|---|---|---|---|---|
| 58 | (Z)-tert-butyl 3-(4-(2-((2,4-dioxothiazolidin-5-ylidene)methyl)phenyl)piperazine-1-carbonyl)benzylcarbamate 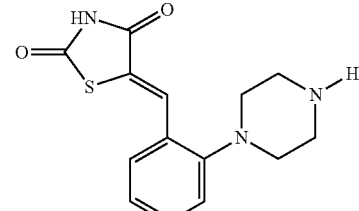 | | 524 | (5Z)-5-(2-piperazin-1-ylbenzylidene)-1,3-thiazolidine-2,4-dione 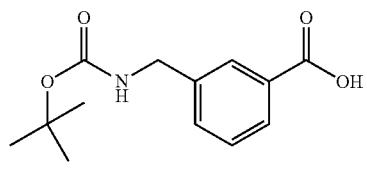<br>Example 115 and 3-{[(tert-butoxycarbonyl)amino]methyl}benzoic acid |
| 63 | tert-butyl 3-(4-(2-((2,4-dioxothiazolidin-5-ylidene)methyl)phenyl)piperazine-1-carbonyl)piperidine-1-carboxylate 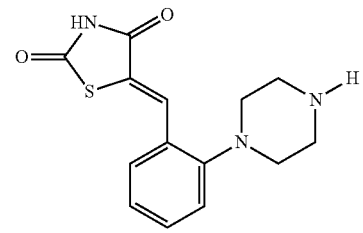 | | 501 | (5Z)-5-(2-piperazin-1-ylbenzylidene)-1,3-thiazolidine-2,4-dione<br>Example 115 And 1-(tert-butoxycarbonyl)piperidine-3-carboxylic acid 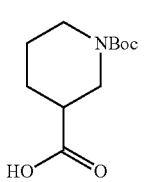 |

| Method | Compound | ¹H NMR | m/z | SM |
|---|---|---|---|---|
| 64 | tert-butyl 3-(4-(2-((2,4-dioxothiazolidin-5-ylidene)methyl)phenyl)piperazine-1-carbonyl)azetidine-1-carboxylate 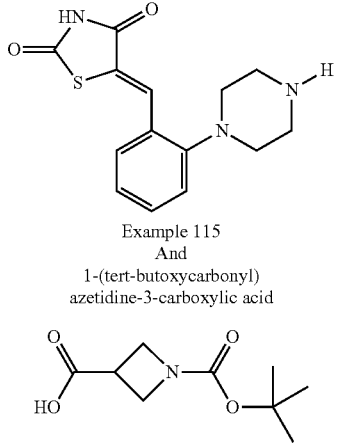 | | 473 | (5Z)-5-(2-piperazin-1-ylbenzylidene)-1,3-thiazolidine-2,4-dione 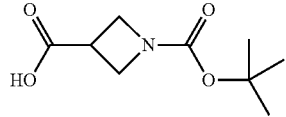  Example 115 And 1-(tert-butoxycarbonyl)azetidine-3-carboxylic acid |
| 66 | (R,Z)-tert-butyl 5-(1-(2-((2,4-dioxothiazolidin-5-ylidene)methyl)-4,5-dimethoxyphenyl)pyrrolidin-3-ylamino)-5-oxopentylcarbamte 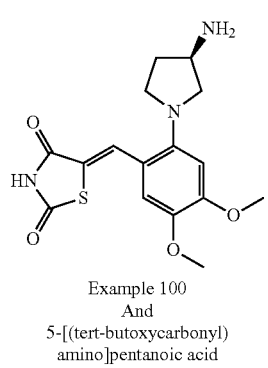 | | 550 | (R,Z)-5-(2-(3-aminopyrrolidin-1-yl)-4,5-dimethoxybenzylidene)thiazolidine-2,4-dione 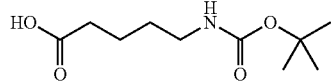  Example 100 And 5-[(tert-butoxycarbonyl)amino]pentanoic acid |

-continued

| Method | Compound | ¹H NMR | m/z | SM |
|---|---|---|---|---|
| 67 | (S,Z)-tert-butyl 5-(1-(2-((2,4-dioxothiazolidin-5-ylidene)methyl)-4,5-dimethoxyphenyl)pyrrolidin-3-ylamino)-5-oxopentylcarbamate | | 550 | (S,Z)-5-(2-(3-aminopyrrolidin-1-yl)-4,5-dimethoxybenzylidene)thiazolidine-2,4-dione<br><br>Example 101<br>And<br>5-[(tert-butoxycarbonyl)amino]pentanoic acid |
| 75 | (Z)-3-(1,3-dioxoisoindolin-2-yl)-N-(1-(2-((2,4-dioxothiazolidin-5-ylidene)methyl)-4,5-dimethoxyphenyl)pyrrolidin-3-yl)propanamide | | 552 | (5Z)-5-[2-(3-aminopyrrolidin-1-yl)-4,5-dimethoxybenzylidene]-1,3-thiaozolidine-2,4-dione<br><br>Example 118<br>and<br>3-(1,3-dioxo-1,3-dihydro-2H-isoindol-2-yl)propanoic acid |

| Method | Compound | ¹H NMR | m/z | SM |
|---|---|---|---|---|
| 76 | 5Z)-2-(4-(3-(1,3-dioxoisoindolin-2-yl)propanoyl)piperazin-1-yl)benzylidene)thiazolidine-2,4-dione<br>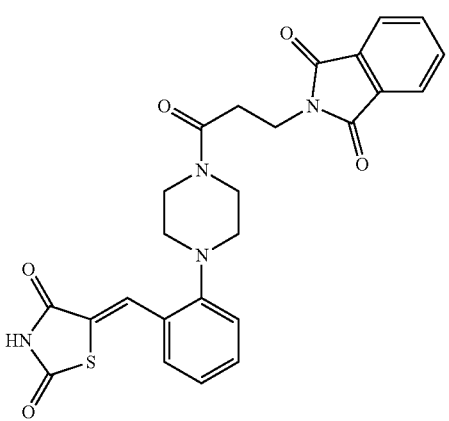 | | | (5Z)-5-(2-piperazin-1-ylbenzylidene)-1,3-thiazolidine-2,4-dione<br>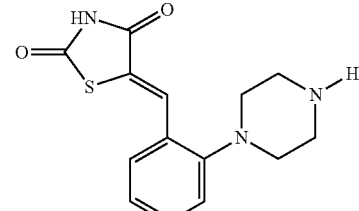<br>Example 115<br>and<br>3-(1,3-dioxo-1,3-dihydro-2H-isoindol-2-yl)propanoic acid<br>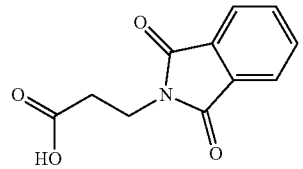 |

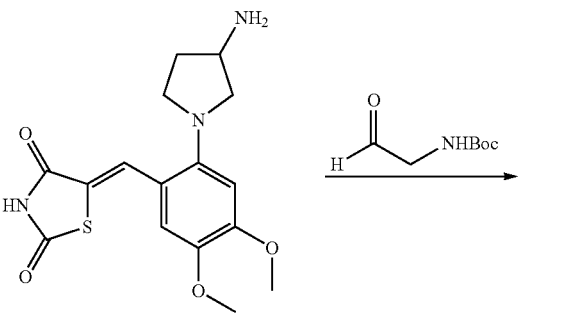

Method 59:

(Z)-tert-butyl 2-(1-(2-((2,4-dioxothiazolidin-5-ylidene)methyl)-4,5-dimethoxyphenyl)pyrrolidin-3-ylamino)ethylcarbamate A mixture of (5Z)-5-{2-[3-(dimethylamino)pyrrolidin-1-yl]-4,5-dimethoxybenzylidene}-1,3-thiazolidine-2,4-dione (Example 52) (120 mg, 0.31 mmol) and tert-butyl 2-oxoethylcarbamate (198 mg, 1.24 mmol) in $CH_2Cl_2$ (20 mL) were heated to reflux for 15 min followed by the addition of sodium triacetoxyhydroborate (65.9 mg, 0.31 mmol). The reaction mixture was refluxed overnight before being allowed to cool to ambient temperature. Water (~0.5 mL) was added and the mixture was allowed to stir for 15 min before being loaded onto a silica gel column which was eluted with ethyl acetate/hexane (10:1) to yield the title compound as an orange solid as (60.0 mg, 39.2%); m/z 493.

The following intermediates were prepared by the procedure of Method 59, using the appropriate starting materials.

| Method | Compound | ¹H NMR | m/z | SM |
|---|---|---|---|---|
| 60 | (Z)-tert-butyl 2-(4-(2-((2,4-dioxothiazolidin-5-ylidene)methyl)phenyl)piperazin-1-yl)ethylcarbamate 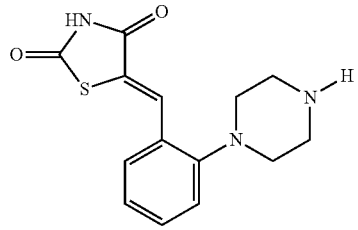 | | 433 | (5Z)-5-(2-piperazin-1-ylbenzylidene)-1,3-thiazolidine-2,4-dione 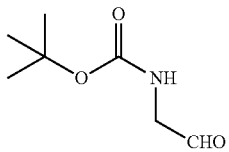<br>Example 115<br>and<br>tert-butyl (2-oxoethyl)carbamate |
| 61 | (Z)-tert-butyl 2-(1-(2-((2,4-dioxothiazolidin-5-ylidene)methyl)-4,5-dimethoxyphenyl)pyrrolidin-3-ylamino)ethyl(methyl)carbamate 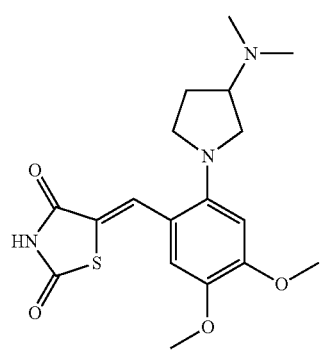 | | 507 | (5Z)-5-{2-[3-(dimethylamino)pyrrolidin-1-yl]-4,5-dimethoxybenzylidene}-1,3-thiazolidine-2,4-dione 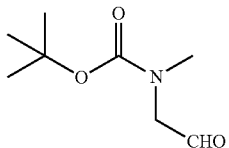<br>Example 52<br>and<br>tert-butyl methyl(2-oxoethyl)carbamate |

-continued

| Method | Compound | ¹H NMR | m/z | SM |
|---|---|---|---|---|
| 62 | (Z)-tert-butyl 2-(4-(2-((2,4-dioxothiazolidin-5-ylidene)methyl)phenyl)piperazin-1-yl)ethyl (methyl)carbabmate Method 62 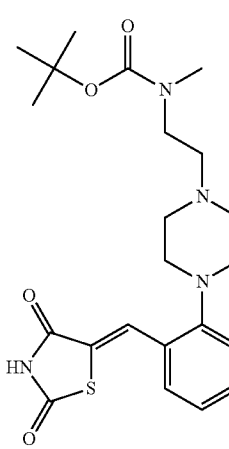 | | 448 | (5Z)-5-(2-piperazin-1-ylbenzylidene)-1,3-thiazolidine-2,4-dione 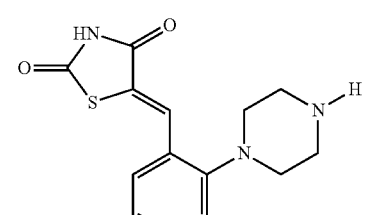 Example 115 and tert-butyl methyl(2-oxoethyl)carbamate 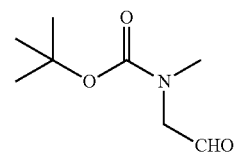 |
| 68 | (S,Z)-tert-butyl 3-(1-(2-((2,4-dioxothiazolidin-5-ylidene)methyl)-4,5-dimethoxyphenyl)pyrrolidin-3-ylamino)propylcarbamate 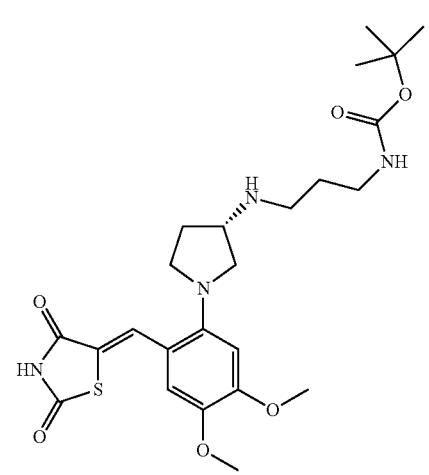 | | 507 | (S,Z)-5-(2-(3-aminopyrrolidin-1-yl)-4,5-dimethoxybenzylidene)thiazolidine-2,4-dione 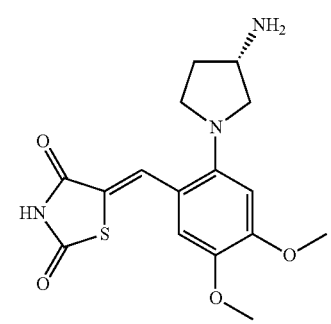 Example 101 and tert-butyl (3-oxopropyl)carbamate 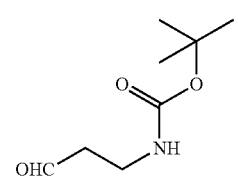 |

| Method | Compound | ¹H NMR | m/z | SM |
|---|---|---|---|---|
| 69 | (R,Z)-tert-butyl 3-(1-(2-((2,4-dioxothiazolidin-5-ylidene)methyl)-4,5-dimethoxyphenyl)pyrrolidin-3-ylamino)propylcarbamate 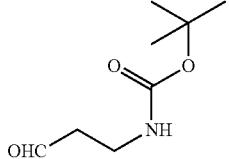 | | 507 | (R,Z)-5-(2-(3-aminopyrrolidin-1-yl)-4,5-dimethoxybenzylidene)thiazolidine-2,4-dione 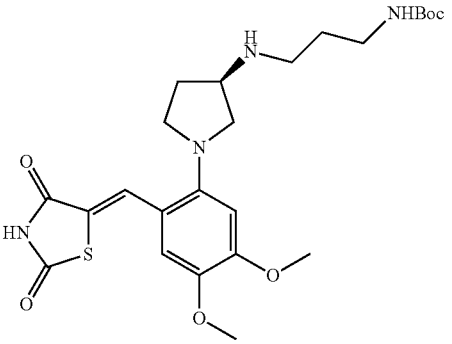<br>Example 100 and tert-butyl (3-oxopropyl)carbamate 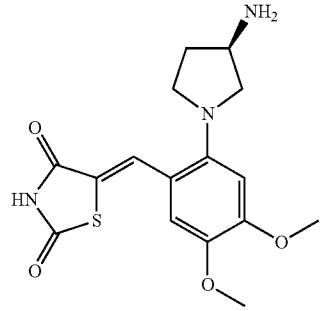 |
| 70 | (S,Z)-5-(2-(3-(3-(1,3-dioxoisoindolin-2-yl)propylamino)pyrrolidin-1-yl)-5-(trifluoromethyl)benzylidene)thiazolidine-2,4-dione 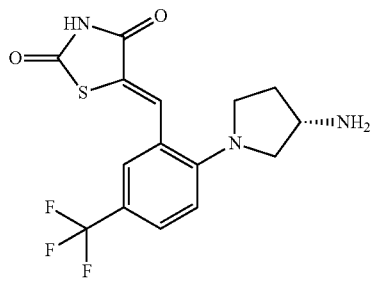 | | 545 | (S,Z)-5-(2-(3-aminopyrrolidin-1-yl)-5-(trifluoromethyl)benzylidene)thiazolidine-2,4-dione 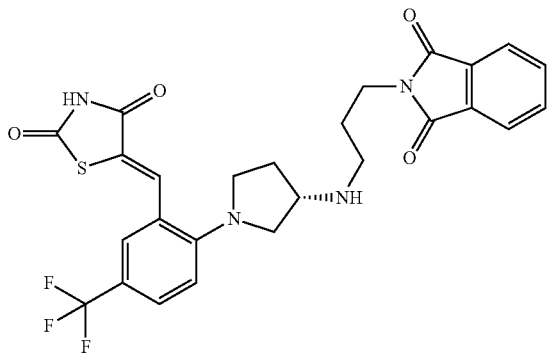<br>Example 88 and 3-(1,3-dioxoisoindolin-2-yl)propanal 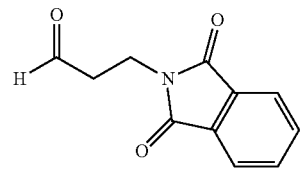 |

-continued

| Method | Compound | ¹H NMR | m/z | SM |
|---|---|---|---|---|
| 71 | (S,Z)-5-(2-(3-(3-(1,3-dioxoisoindolin-2-yl)propylamino)pyrrolidin-1-yl)-3-methoxybenzylidene)thiazolidine-2,4-dione 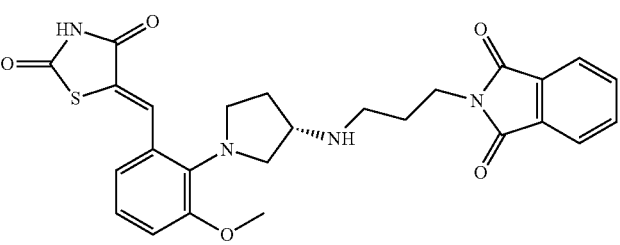 |  | 508 | (S,Z)-5-(2-(3-aminopyrrolidin-1-yl)-3-methoxybenzylidene)thiazolidine-2,4-dione 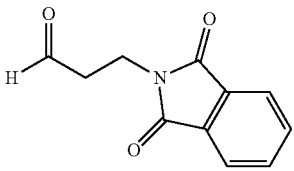<br>Example 96 and 3-(1,3-dioxoisoindolin-2-yl)propanal |
| 72 | (S,Z)-5-(3-chloro-2-(3-(3-(1,3-dioxoisoindolin-2-yl)propylamino)pyrrolidin-1-yl)benzylidene)thiazolidine-2,4-dione 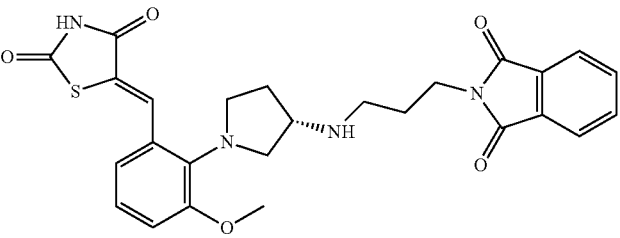 |  | 512 | (S,Z)-5-(2-(3-aminopyrrolidin-1-yl)-3-chlorobenzylidene)thiazolidine-2,4-dione 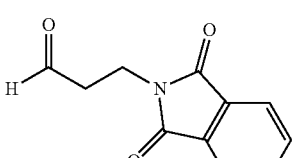<br>Example 86 and 3-(1,3-dioxoisoindolin-2-yl)propanal |

-continued

| Method | Compound | ¹H NMR | m/z | SM |
|---|---|---|---|---|
| 73 | (Z)-5-(2-(3-(3-(1,3-dioxoisoindolin-2-yl)propylamino)pyrrolidin-1-yl)-4,5-dimethoxybenzylidene)thiazolidine-2,4-dione | | 507 | (5Z)-5-{2-[3-(dimethylamino)pyrrolidine-1-yl]-4,5-dimethoxy-benzylidene}-1,3-thiazolidine-2,4-dione<br><br>Example 52 and 3-(1,3-dioxoisoindolin-2-yl)propanal |
| 74 | (Z)-5-(2-(4-(3-(1,3-dioxoisoinodolin-2-yl)propyl)piperazin-1-yl)benzylidene)thiazolidine-2,4-dione | | 477 | (5Z)-5-(2-piperazin-1-ylbenzylidene)-1,3-thiazolidine-2,4-dione<br><br>Example 115 and 3-(1,3-dioxoisoindolin-2-yl)propanal |

| Method | Compound | ¹H NMR | m/z | SM |
|---|---|---|---|---|
| 77 | (Z)-5-(2-(3-(2-(tert-butyldimethylsilyloxy)ethylamino)pyrrolidin-1-yl)-4,5-dimethoxybenzylidene)thiazolidine-2,4-dione | | 509 | (5Z)-5-[2-(3-aminopyrrolidin-1-yl)-4,5-dimethoxybenzylidene]-1,3-thiazolidine-2,4-dione<br><br>Example 118 and 2-(tert-butyldimethylsilyloxy)acetaldehyde |
| 167 | (R,Z)-tert-butyl 4-((1-(2-chloro-6-((2,4-dioxothiazolidin-5-ylidene)methyl)phenyl)piperidin-3-ylamino)methyl)benzylcarbamate | | 557 | (R,Z)-5-(2-(3-aminopiperidin-1-yl)-3-chlorobenzylidene)thiazolidine-2,4-dione hydrochloride<br>Example 122D<br><br>And tert-butyl 4-formylbenzylcarbamate |

| Method | Compound | ¹H NMR | m/z | SM |
|---|---|---|---|---|
| 168 | (R,Z)-tert-butyl 2-(1-(2-chloro-6-((2,4-dioxothiazolidin-5-ylidene)methyl)phenyl)piperidin-3-ylamino)ethyl(methyl)carbamate 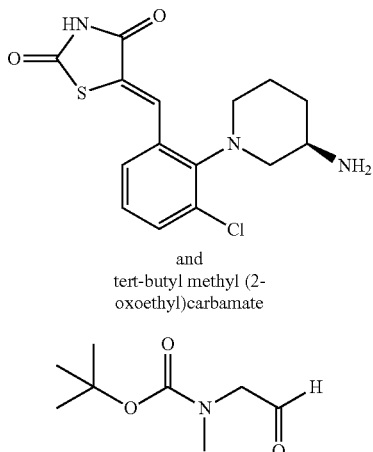 | | 496 | (R,Z)-5-(2-(3-aminopiperidin-1-yl)-3-chlorobenzylidene)thiazolidine-2,4-dione hydrochloride Example 122D 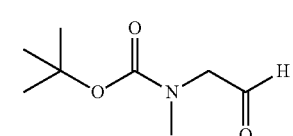 and tert-butyl methyl (2-oxoethyl)carbamate |
| 169 | (R,Z)-5-(2-(3-(2-(tert-butyldimethylsilyloxy)ethylamino)piperidin-1-yl)-3-chlorobenzylidene)thiazolidine-2,4-dione 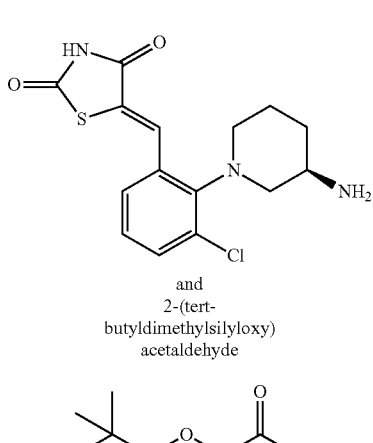 | | 496 | (R,Z)-5-(2-(3-aminopiperidin-1-yl)-3-chlorobenzylidene)thiazolidine-2,4-dione hydrochloride Example 122D 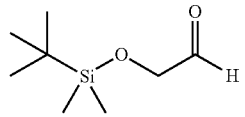 and 2-(tert-butyldimethylsilyloxy)acetaldehyde |

-continued

| Method | Compound | ¹H NMR | m/z | SM |
|---|---|---|---|---|
| 170 | (R,Z)-5-(2-(3-(3-(tert-butyldimethylsilyloxy)propylamino)piperidin-1-yl)-3-chlorobenzylidene)thiazolidene-2,4-dione | | 510 | (R,Z)-5-(2-(3-aminopiperidin-1-yl)-3-chlorobenzylidene)thiazolidine-2,4-dione hydrochloride Example 122D<br><br>and<br><br>3-(tert-butyldimethylsilyloxy)propanal |
| 171 | (R,Z)-5-(3-chloro-2-(3-(3-(1,3-dioxoisoindolin-2-yl)propylamino)piperidin-1-yl)benzylidene)thiazolidine-2,4-dione | | 525 | (R,Z)-5-(2-(3-aminopiperidin-1-yl)-3-chlorobenzylidene)thiazolidine-2,4-dione hydrochloride Example 122D<br><br>3-(1,3-dioxoisoindolin-2-yl)propanal |

Method 172

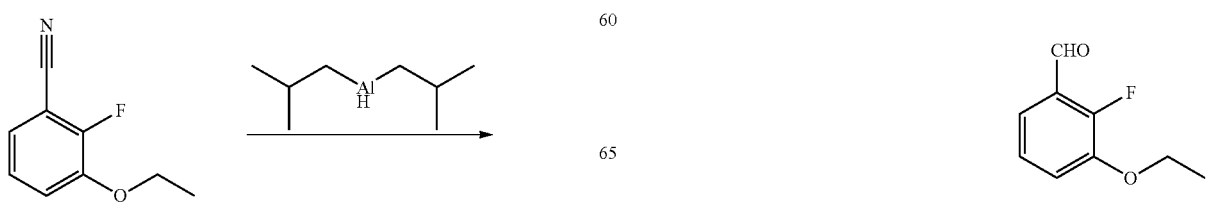

-continued

3-ethoxy-2-fluorobenzaldehyde

A 200 mL round bottom flask was charged with a magnetic stir bar, 3-ethoxy-2-fluorobenzonitrile (1.000 g, 6.05 mmol), and anhydrous toluene (12.92 ml). The sol'n was placed under argon and cooled to 0° C. with an ice bath. DIBAL-H (7.27 ml, 7.27 mmol) (1M in PhMe) was then added drop wise via syringe and the reaction was allowed to stir to rt overnight. To this mixture was added 10% HCl until the sol'n reached a pH of ~2. The resulting mixture was then left to stir for 0.5 h. and was then poured into a separatory funnel and extracted with ethyl acetate (2×200 mL). The combined organic extract was dried with MgSO$_4$, filtered, and conc. in vacuo to yield the crude product which was purified via silica gel chromatography (80 g) using ethyl acetate/hexanes (1:4) as eluent to provide pure 3-ethoxy-2-fluorobenzaldehyde (0.810 g, 80%). m/z 196.

The following intermediates were prepared by the procedure of Method 172, using the appropriate starting materials.

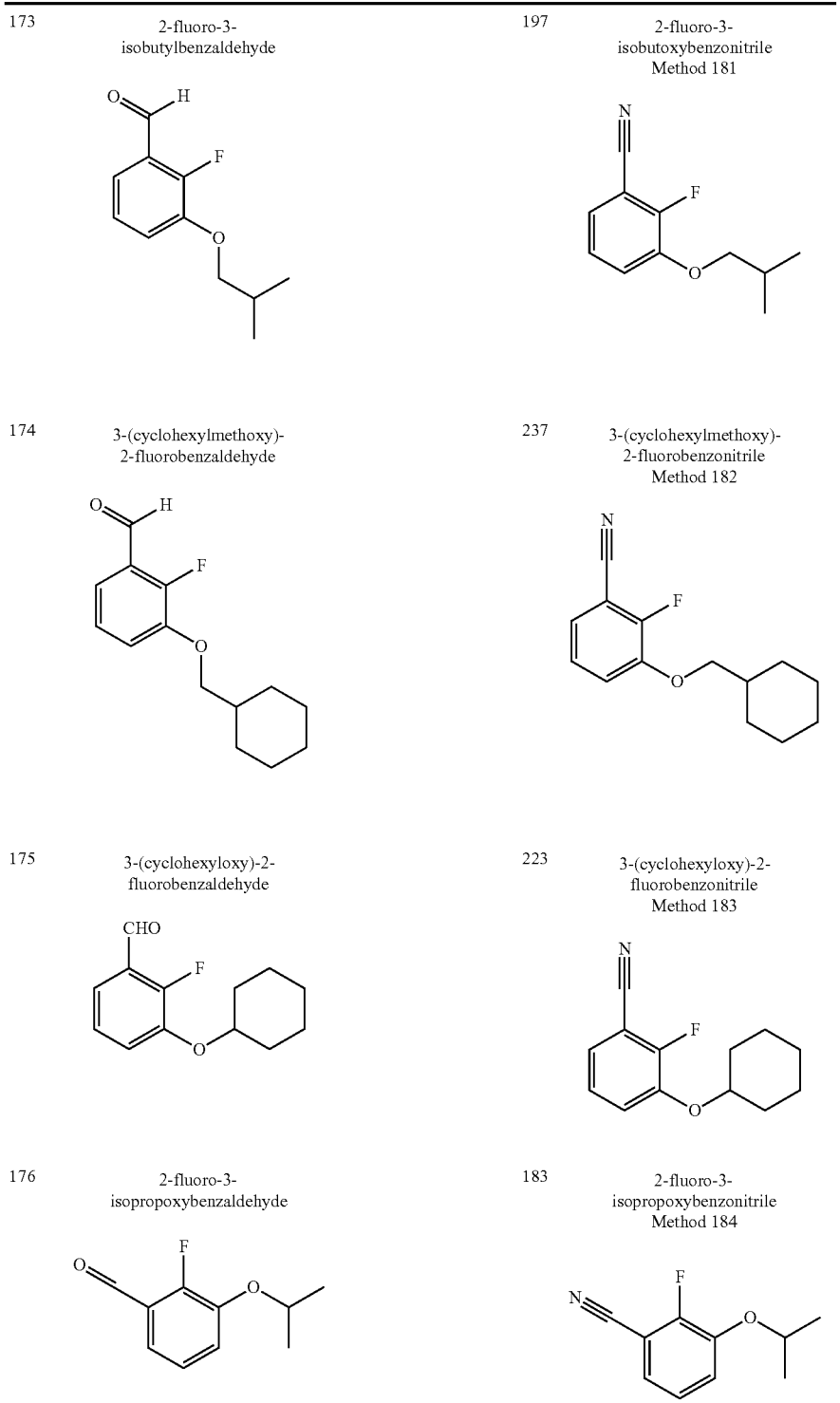

| | | | | | |
|---|---|---|---|---|---|
| 177 | 2-fluoro-3-(2,2,2-trifluoroethoxy)benzaldehyde 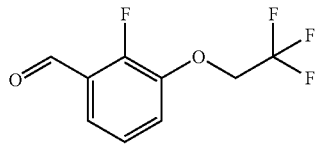 | | 223 | 2-fluoro-3-(2,2,2-trifluoroethoxy)benzonitrile Method 200 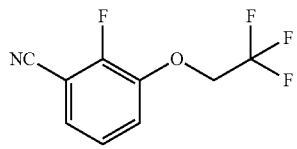 | |
| 178 | 2-fluoro-3-(2-methoxyethoxy)benzaldehyde 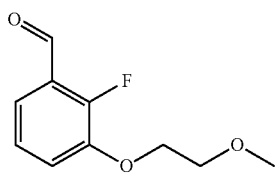 | 10.32 (s, 1 H) 7.56-7.35 (m, 2 H) 7.13-6.96 (m, 1 H) 4.33-4.22 (m, 2 H) 3.84-3.77 (m, 2 H) 3.42 (s, 3 H) | 199 | 2-fluoro-3-(2-methoxyethoxy)benzonitrile Method 185 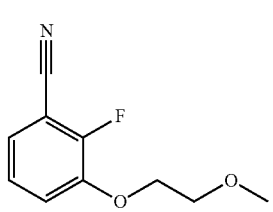 | |
| 179 | 3-(cyclopentyloxy)-2-fluorobenzaldehyde 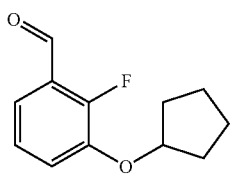 | | 195 | 3-(cyclopentyloxy)-2-fluorobenzonitrile Method 187 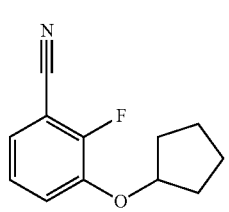 | |
| 180 | 3-cyclobutoxy-2-fluorobenzaldehyde 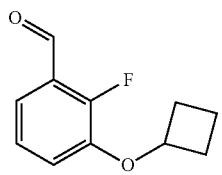 | 10.31 (s, 1 H) 7.41-7.36 (m, 2 H) 7.05-7.03 (m, 1 H) 4.94-4.85 (m, 1 H) 2.01-1.83 (m, 8 H) | 209 | 3-cyclobutoxy-2-fluorobenzonitrile Method 186 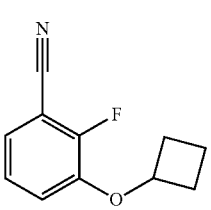 | |

Method 181

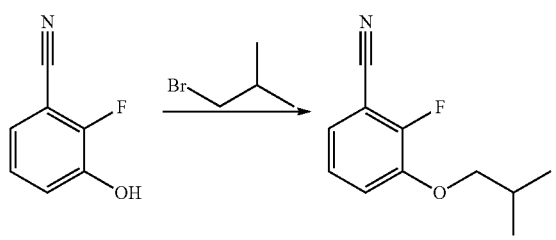

A 100 mL round bottom flask was charged with a magnetic stir bar, 2-fluoro-3-hydroxybenzonitrile (0.500 g, 3.65 mmol), MeCN (13.89 ml), 1-bromo-2-methylpropane (0.699 ml, 7.29 mmol), and $K_2CO_3$ (1.008 g, 7.29 mmol). The mixture was then placed in an oil bath and heated to 60° C. with stirring overnight. This mixture was then cooled to rt, filtered through a bed of Celite, and conc. In vacuo. The crude material was purified via silica gel chromatography (40 g) using ethyl acetate/hexanes (1:4) as eluent to afford pure 2-fluoro-3-isobutoxybenzonitrile (0.610 g, 87%) as a colorless oil. M/z 194.

The following intermediates were prepared by the procedure of Method 181, using the appropriate starting materials.

| | | | |
|---|---|---|---|
| 182 | 3-(cyclohexylmethoxy)-2-fluorobenzonitrile 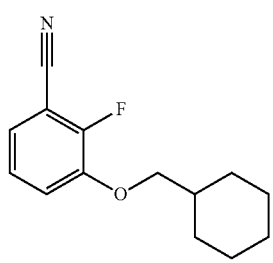 | 234 | 2-fluoro-3-hydroxybenzonitrile 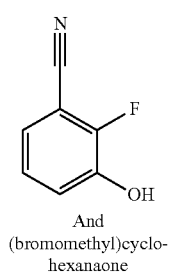<br>And (bromomethyl)cyclohexanaone 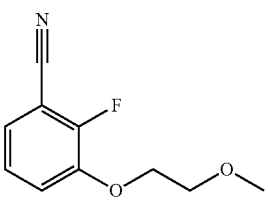 |
| 185 | 2-fluoro-3-(2-methoxyethoxy)benzonitrile 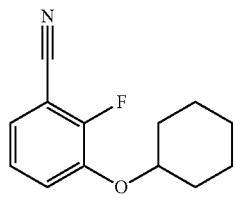 | 196 | 2-fluoro-3-hydroxybenzonitrile 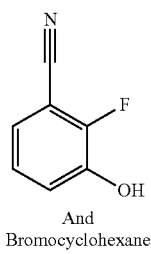<br>And 1-bromo-2-methoxyethane 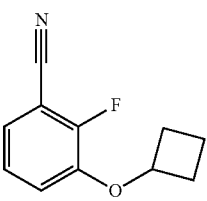 |
| 183 | 3-(cyclohexyloxy)-2-fluorobenzonitrile | 220 | 2-fluoro-3-hydroxybenzonitrile<br>And Bromocyclohexane |
| 186 | 3-cyclobutoxy-2-fluorobenzonitrile | 192 | 2-fluoro-3-hydroxybenzonitrile<br>And Bromocyclobutane |
| 184 | 2-fluoro-3-isopropoxybenzonitrile 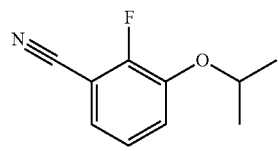 | 179 | 2-fluoro-3-hydroxybenzonitrile 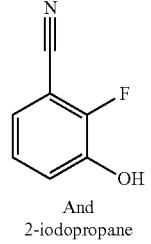<br>And 2-iodopropane |
| 187 | 3-(cyclopentyloxy)-2-fluorobenzonitrile 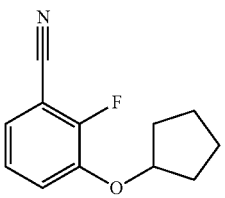 | | 2-fluoro-3-hydroxybenzonitrile 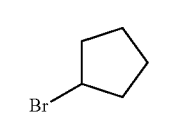<br>And bromocyclopentane 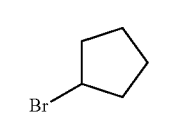 |

Method 188

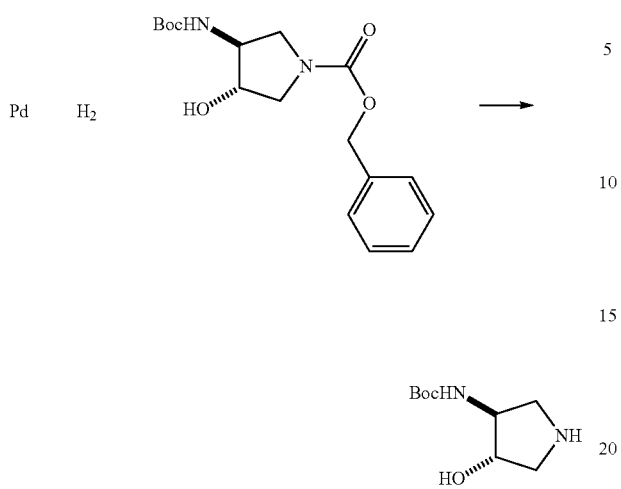

(±)-tert-butyl-4-hydroxypyrrolidin-3-ylcarbamate

A racemic mixture of trans-benzyl 3-(tert-butoxycarbonylamino)-4-hydroxypyrrolidine-1-carboxylate (3.36 g, 9.99 mmol) (Method 190) in MeOH (40 mL) was degassed, then 10 wt % Pd/C (3.19 g, 3.00 mmol) was added. The mixture was degassed, charged with H$_2$, and stirred overnight. The mixture was filtered through a bed of Celite, washed with methanol, the filtrate was dried over anhydrous Na$_2$SO$_4$, filtered and conc. in vacuo to yield a white solid as racemic tert-butyl-4-hydroxypyrrolidin-3-ylcarbamate (2.020 g, 100%). $^1$H NMR (400 MHz, MeOD) δ ppm 4.13 (dt, 1 H), 3.89-3.75 (m, 1 H), 3.35 (brs, 1 H), 3.14 (dd, 1 H), 2.93-2.73 (m, 2 H), 1.46 (s, 10 H); m/z 203.

The following intermediates were prepared by the procedure of Method 188, using the appropriate starting materials.

Method 190

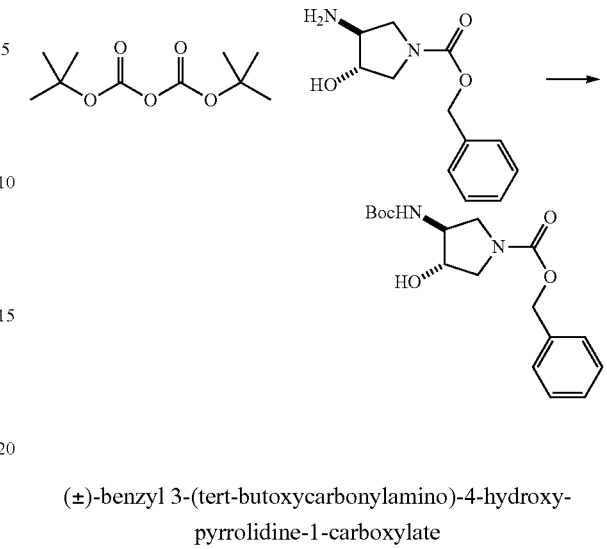

(±)-benzyl 3-(tert-butoxycarbonylamino)-4-hydroxypyrrolidine-1-carboxylate

To a mixture of racemic trans-benzyl 3-amino-4-hydroxypyrrolidine-1-carboxylate (2.67 g, 11.30 mmol) (Method 193) and di-tert-butyl dicarbonate (3.70 g, 16.95 mmol) in CH$_2$Cl$_2$ (50 mL) was added Et$_3$N (4.73 mL, 33.90 mmol) at 0° C. The mixture was then stirred at rt for 48 h. The reaction mixture was then conc. in vacuo giving a residue which was purified via silica gel chromatography (40% to 90% ethyl acetate/hexane) to yield a white solid as (±)-benzyl 3-(tert-butoxycarbonylamino)-4-hydroxypyrrolidine-1-carboxylate (3.36 g, 88%). $^1$H NMR (400 MHz, Dichloromethane-d2) δ ppm 7.48-7.32 (m, 5 H), 5.21-5.00 (m, 2 H), 4.78 (brs, 1 H), 4.29-4.18 (m, 1 H), 3.84 (dd, 1 H), 3.74 (d, 1 H), 3.41-3.12 (m, 2 H), 1.49-1.33 (m, 9 H); m/z 337

The following starting materials were prepared by the procedure of Method 190 using the appropriate starting materials.

| Method | Compound | $^1$H NMR | m/z | SM |
|---|---|---|---|---|
| 189 | (±)-tert-butyl-4-hydroxypiperidin-3-ylcarbamate | | 216 | (±)-benzyl 3-(tert-butoxycarbonylamino)-4-hydroxypiperidine-1-carboxylate Method 191 |

| Method | Compound | m/z | SM |
|---|---|---|---|
| 191 | (±)-benzyl 3-(tert-butoxycarbonylamino)-4-hydroxypiperidine-1-carboxylate 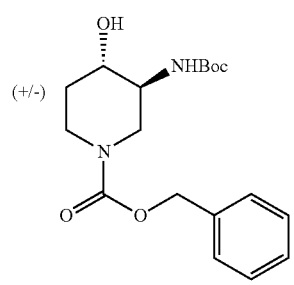 | 350 | (±)-benzyl 3-amino-4-hydroxypiperidine-1-carboxylate Method 194 |
| 192 | tert-butyl 1-(2-chloro-6-formylphenyl)-4-methylpiperidin-3-ylcarbamate | 352 | 2-(3-amino-4-methylpiperidin-1-yl)-3-chlorobenzaldehyde Method 199 |

Method 193

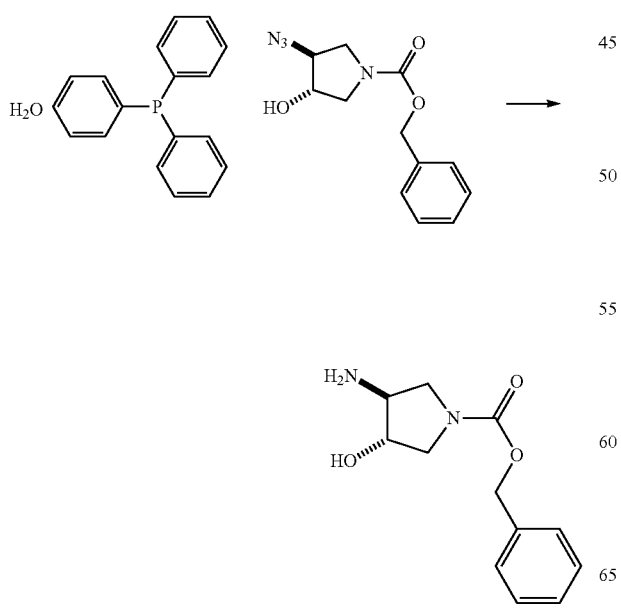

(±)-benzyl 3-amino-4-hydroxypyrrolidine-1-carboxylate

A mixture of racemic trans-benzyl 3-azido-4-hydroxypyrrolidine-1-carboxylate (2.96 g, 11.29 mmol) (Method 195) and triphenylphosphine (3.11 g, 11.85 mmol) in THF (25 mL) was stirred at rt for 7 h. Water (2 mL, 111 mmol) was then added and the mixture then stirred at 50° C. overnight. The mixture was then concentrated under reduced pressure, and the residue was purified via silica gel chromatography (100% DCM to 37:3:60/methanol:Et$_3$N:DCM) to yield the title compound (2.96 g, 11.29 mmol) as an oil. $^1$H NMR (400 MHz, Dichloromethane-d2) δ ppm 7.38-7.19 (m, 5 H), 5.02 (s, 2 H), 3.89 (brs, 1 H), 3.62 (dd, 2 H), 3.29-3.15 (m, 2 H), 3.12-3.01 (m, 1 H); m/z 236.

The following starting materials were prepared by the procedure of Method 193 using the appropriate starting materials.

| Method | Compound | ¹H NMR | m/z | SM |
|---|---|---|---|---|
| 194 | (±)-benzyl 3-amino-4-hydroxypiperidine-1-carboxylate 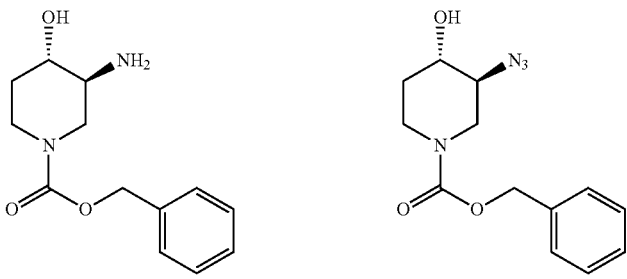 | | 250 | (±)-benzyl 3-azido-4-hydroxypiperidine-1-carboxylate Method 196 |

Method 195

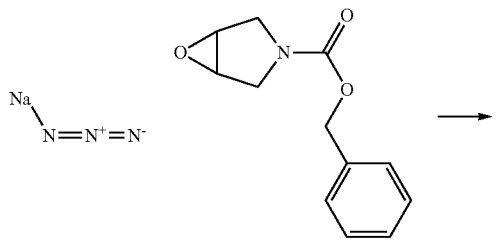

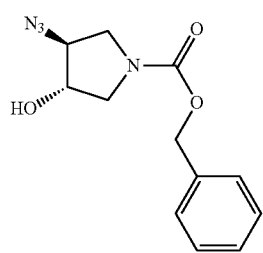

(±)-benzyl 3-azido-4-hydroxypyrrolidine-1-carboxylate

To a stirred mixture of benzyl 6-oxa-3-azabicyclo[3.1.0]hexane-3-carboxylate (5.2 g, 23.72 mmol) (Method 197) in DMF (30 mL) was added sodium azide (2.313 g, 35.58 mmol) in a mixture of acetone (20.00 mL) and water (10.00 mL). The resulting mixture was stirred at 80° C. for 24 h. The mixture was then diluted with water and ether, separated, and the organic layer was washed with brine, dried and conc. in vacuo. The resulting material was purified via silica gel chromatography (eluted with 15% to 35% ethyl acetate/hexane), yielding the title compound as a yellow solid (4.10 g, 65.9%). ¹H NMR (400 MHz, dichloromethane-d2) δ ppm 7.50-7.25 (m, 5 H), 5.43-5.25 (m, 2 H), 4.31 (brs, 1 H), 4.00 (brs, 1 H), 3.77 (dd, 1 H), 3.69 (dd, 1 H), 3.53 (d, 1 H), 3.44 (dd, 1 H), 2.17 (brs, 1 H); m/z 263.

The following starting materials were prepared by the procedure of Method 195 using the appropriate starting materials.

| Method | Compound | ¹H NMR | m/z | SM |
|---|---|---|---|---|
| 196 | (±)-benzyl 3-azido-4-hydroxypiperidine-1-carboxylate | | 276 | benzyl 7-oxa-3-azabicyclo[4.1.0]heptane-3-carboxylate Method 198 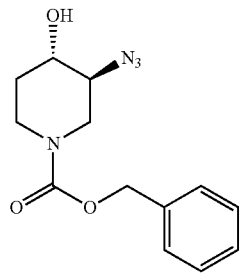 |

Method 197

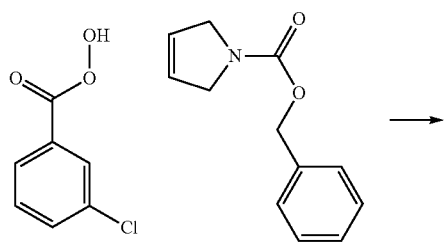

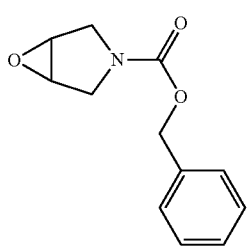

benzyl
6-oxa-3-azabicyclo[3.1.0]hexane-3-carboxylate

To a stirred mixture of benzyl 2,5-dihydro-1H-pyrrole-1-carboxylate (5 g, 24.60 mmol) in DCM (80 mL) was added 3-chlorobenzoperoxoic acid (6.89 g, 30.75 mmol) at 0° C. The mixture was then stirred at rt overnight. The reaction mixture was then filtered through a bed of Celite and the filtrate was washed with sat'd aqueous Na₂CO₃ and brine. The organic was then separated and dried over anhydrous Na₂SO₄, filtered, and conc. in vacuo to yield the title compound that was used for next step without further purification.

The following starting materials were prepared by the procedure of Method 197 using the appropriate starting materials.

Method 199:

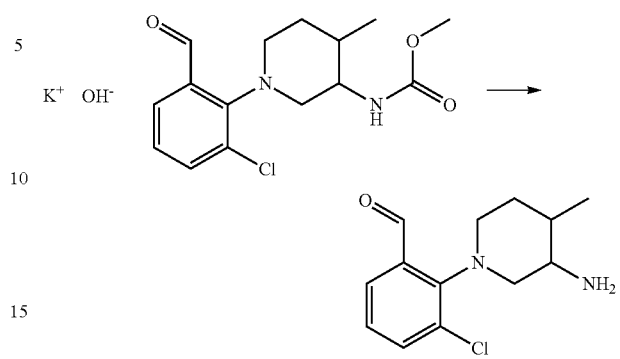

2-(3-amino-4-methylpiperidin-1-yl)-3-chlorobenzaldehyde

To a stirred solution of methyl 1-(2-chloro-6-formylphenyl)-4-methylpiperidin-3-ylcarbamate (220 mg, 0.71 mmol) (Method 119) in MeOH (3 ml) was added 40% aqueous solution of KOH (10 ml) drop wise, and the resulting mixture was heated at reflux for 16 h. The mixture was allowed to cool to rt, diluted with water, and extracted with DCM. The combined organic extract was dried over anhydrous Na₂SO₄, filtered, and conc. in vacuo. The resulting residue was purified via silica gel chromatography (100% ethyl acetate to 10% methanol in ethyl acetate) to yield the title compound as a light yellow gum (0.057 g, 31.9%). ¹H NMR (400 MHz, CHLOROFORM-d) δ ppm 8.44 (s, 1 H), 7.40 (t, 2 H), 7.07 (t, 1 H), 4.29 (d, 1 H), 3.58 (ddd, 1 H), 3.38 (dd, 1 H), 3.11 (td, 1 H), 2.81 (d, 1 H), 2.20-1.91 (m, 1 H), 1.31-1.14 (m, 1 H), 1.08 (d, 3 H), 0.63-0.37 (m, 1 H).

Method 200

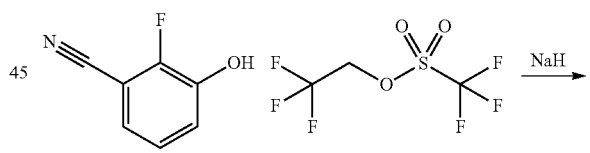

| Method | Compound | ¹H NMR | m/z | SM |
|---|---|---|---|---|
| 198 | benzyl 7-oxa-3-azabicyclo[4.1.0]heptane-3-carboxylate | | 217 | Benzyl 5,6-dihydropyridine-1(2H)-carboxylate |

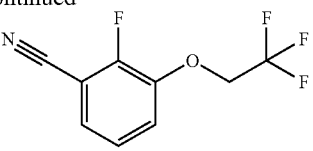

2-fluoro-3-(2,2,2-trifluoroethoxy)benzonitrile

A stirred solution of 2-fluoro-3-hydroxybenzonitrile (800 mg, 5.83 mmol) in DMF (10 mL) at 0° C. was treated portionwise with NaH (280 mg, 7.00 mmol) (60% oil dispersion). The reaction mixture was then stirred for 0.5 h and 2,2,2-trifluoroethyl trifluoromethanesulfonate (1490 mg, 6.42 mmol) was added. The reaction was allowed to warm to rt overnight with stirring. The reaction mixture was then treated with water (40 mL) and brine (5 mL) and extracted with ethyl acetate (~50 mL). The organic extract was washed with water, dried over anhydrous $Na_2SO_4$, filtered and conc. in vacuo to afford a residue which was purified via silica gel chromatography (10% to 30% ethyl acetate/hexanes) to yield the title compound as a white solid (1040 mg, 81%). $^1$H NMR (400 MHz, MeOD) δ ppm 7.56 (td, 1 H), 7.47-7.38 (m, 1 H), 7.38-7.24 (m, 1 H), 4.73 (q, 2 H); m/z 220.
Method 201:

(R)-tert-butyl 1-(3-formylbiphenyl-2-yl)piperidin-3-ylcarbamate

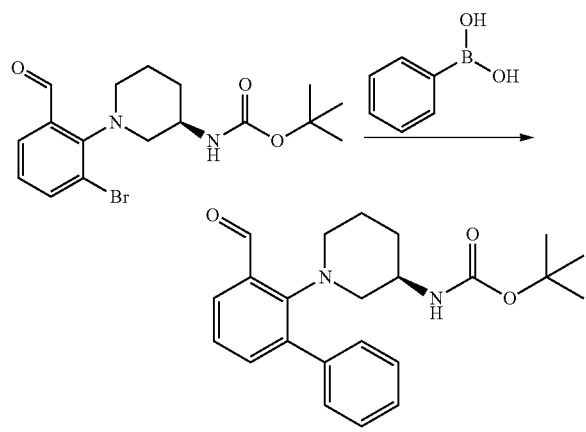

A mixture of (R)-tert-butyl 1-(2-bromo-6-formylphenyl) piperidin-3-yl carbamate (Method 95) (300 mg, 0.78 mmol), phenylboronic acid (143 mg, 1.17 mmol), 1,1'-bis(di-tert-butyllphosphino)ferrocenedichloro palladium (II) complex (40.8 mg, 0.06 mmol), and $Na_2CO_3$ (124 mg, 1.17 mmol) was suspended in dioxane (5 mL) and water (1.50 mL) and stirred at 110° C. for overnight under an atmosphere of nitrogen. The reaction was cooled to rt and water (~50 mL) and ethyl acetate (~50 mL) was added to the mixture. The organic phase was separated, dried over anhydrous $MgSO_4$, filtered, and conc. in vacuo affording a residue purified with via silica gel chromatography (40 g) using a gradient of 5% to 30% ethyl acetate/hexanes to yield the title compound as a low melting solid (168 mg, 56.4%); m/z 381.

One may purify examples provided above by reverse-phase HPLC in a solvent contain varying concentrations of trifluoroacetic acid or hydrochloric acid. Thus the examples above may be isolated as, the freebase, hydrochloride salt, or trifluoroacetate salt.

PIM 1 and 2 enzyme assay descriptions:
PIM1 In-Vitro Mobility Shift Assay

One may determine the activity of purified human His-PIM1 [2-313] enzyme in-vitro using a mobility shift assay on a Caliper LC3000 reader (Caliper, Mass.), which measures fluorescence of a phosphorylated and unphosphorylated FL-Ahx-Bad (FITC-(AHX)RSRHSSYPAGT-COOH, Primm 200606-00289, Primm Biotech, Mass.) and calculates a ratiometric value to determine percent turnover. One may express PIM1 (University of Dundee, Scotland) in baculovirus system with a typical yield of >85% purity.

One determines phosphorylation of the FL-Ahx-Bad in the presence and absence of the compound of interest. One preincubates 5u1 of Enzyme/Substrate/adenosine triphosphate (ATP) mix consisting of 2.4 nM PIM1, 3.6 uM FL-Ahx-Bad, and 240 uM ATP in 1.2× buffer with 2 ul of compound for 20 minutes at 25° C. One initiates reactions with 5 ul of Metal mix consisting of 24 mM $MgCl_2$ in 1.2× buffer and incubated at 25° C. for 90 minutes and stops the reactions by addition of 5 ul of Stop mix consisting of 100 mM HEPES, 121 mM ethylenediamine tetraacetic acid, 0.8% Coatin Reagent 3 (Caliper, Mass.), and 0.01% Tween. One detects phosphorylated and unphosphorylated substrate by a Caliper LC3000 reader (Caliper, Mass.) in the presence of separation buffer consisting of 100 mM HEPES, 16 mM ethylenediamine tetraacetic acid, 0.1% Coatin Reagent 3 (Caliper, Mass.), 0.015% Brij-35, 5% DMSO, and 5.6 mM $MgCl_2$. One may use the following separation conditions for a Caliper LC3000: −1.0 PSI, −2000 V upstream voltage, −400 V downstream voltage, 0.2 second sample sip, 45 second post sip, 10% laser strength.

PIM2 In-Vitro Mobility Shift Assay

One may determine the activity of purified human His-PIM2 [23-299] enzyme in-vitro using a mobility shift assay on a Caliper LC3000 reader (Caliper, Mass.), which measures fluorescence of a phosphorylated and unphosphorylated FL-Ahx-Bad (FITC-(AHX)RSRHSSYPAGT-COOH, Primm 200606-00289, Primm Biotech, Mass.) and calculates a ratiometric value to determine percent turnover. One may express PIM2 (produced at AstraZeneca, R&D Boston) in E. coli cells with a typical yield of >90% purity.

One determines phosphorylation of the FL-Ahx-Bad in the presence and absence of the compound of interest. One preincubates 5 uL of Enzyme/Substrate/adenosine triphosphate (ATP) mix consisting of 2.4 nM PIM1, 3.6 uM FL-Ahx-Bad, and 12 uM ATP in 1.2× buffer with 2 ul of compound for 20 minutes at 25° C. One initiates reactions with 5 uL of Metal mix consisting of 24 mM $MgCl_2$ in 1.2× buffer and incubates at 25° C. for 90 minutes. One stops reactions by addition of 5 uL of Stop mix consisting of 100 mM HEPES, 121 mM ethylenediamine tetraacetic acid, 0.8% Coatin Reagent 3 (Caliper, Mass.), and 0.01% Tween. One detects phosphorylated and unphosphorylated substrate by a Caliper LC3000 reader (Caliper, Mass.) in the presence of separation buffer consisting of 100 mM HEPES, 16 mM ethylenediamine tetraacetic acid, 0.1% Coatin Reagent 3 (Caliper, Mass.), 0.015% Brij-35, 5% DMSO, and 5.6 mM $MgCl_2$. One may use the following separation conditions for a Caliper LC3000: −1.0 PSI, −2000 V upstream voltage, −400 V downstream voltage, 0.2 second sample sip, 45 second post sip, 10% laser strength.

Using the above described assays, or appropriate modifications thereof, preferred compounds disclosed herein generally have an $IC_{50}$ for PIM1 of less that 5 micromolar (uM), and even more preferred of less than 1 micromolar. The table 1 below provides the percent inhibition of PIM1 at 0.3 micromolar for Examples provided herein. Several examples were tested more than once. Variations in the experimental outcomes, negative values, or values over 100% inhibition are presumably due to experimental error inherent in the assay.

TABLE 1

| Example number | PIM1 % I at 0.3 uM | PIM2 % I at 0.3 uM |
| --- | --- | --- |
| 1 | >95 | 77.7 |
| 2 | >95 | >95 |
| 3 | >95 | 58.0 |
| 4 | >95 | 79.6 |
| 5A | >95 | 79.9 |
| 5B | >95 | >95 |
| 6 | 79.4 | 9.5 |
| 7 | 5.4 | <5 |
| 8 | 16.3 | <5 |
| 9 | 6.9 | <5 |
| 10 | >95 | 50.1 |
| 11 | 89.4 | 17.9 |
| 12 | 80.2 | <5 |
| 13 | <5 | <5 |
| 14 | >95 | 69.9 |
| 15 | 12.9 | <5 |
| 16 | 13.9 | <5 |
| 17 | 29.8 | <5 |
| 18 | <5 | <5 |
| 19 | >95 | 38.3 |
| 20 | 86.5 | 19.1 |
| 21 | 82.9 | 15.8 |
| 22 | 81.9 | 8.5 |
| 23 | 87.6 | 19.7 |
| 24 | >95 | 44.3 |
| 25 | >95 | 68.4 |
| 26 | >95 | 49.6 |
| 27 | 90.8 | 25.1 |
| 28 | 90.0 | 27.4 |
| 29 | 92.8 | |
| 30 | 90.8 | 15.6 |
| 31 | 92.8 | 23.3 |
| 32 | 94.0 | 31.9 |
| 33 | >95 | >95 |
| 34 | >95 | 39.3 |
| 35 | <5 | <5 |
| 36 | >95 | >95 |
| 37 | 89.7 | 69.4 |
| 38 | >95 | 92.9 |
| 39 | 89.4 | 57.3 |
| 40 | >95 | 89.8 |
| 41 | 74.0 | 25.1 |
| 42 | 58.8 | 23.3 |
| 43 | 55.4 | 14.7 |
| 44 | 83.8 | 46.7 |
| 45 | 40.1 | 14.3 |
| 46 | 13.4 | 15.7 |
| 47 | 50.0 | 26.3 |
| 48 | 84.4 | 41.3 |
| 49 | >95 | 86.3 |
| 50 | 93.7 | 45.4 |
| 51 | 85.5 | 80.6 |
| 52 | >95 | 93.5 |
| 53 | 92.3 | 82.1 |
| 54 | 88.1 | 73.1 |
| 55 | 11.0 | <5 |
| 56 | 90.7 | 33.5 |
| 57 | 53.3 | 42.6 |
| 58 | 16.0 | 7.1 |
| 59 | <5 | 6.6 |
| 60 | 35.4 | 11.3 |
| 61 | 81.8 | 28.1 |
| 62 | 62.1 | 17.5 |
| 63 | 79.2 | 21.5 |
| 64 | 86.5 | 25.7 |
| 65 | 45.3 | 18.9 |
| 66 | 50.3 | 20.9 |
| 67 | | <5 |
| 68 | 41.9 | 9.0 |
| 69 | <5 | 16.3 |
| 70 | <5 | <5 |
| 71 | <5 | <5 |
| 72 | <5 | <5 |
| 73 | <5 | <5 |
| 74 | | |
| 75 | >95 | 69.5 |
| 76 | 59.6 | 27.6 |
| 77 | 51.2 | 22.7 |
| 78 | 71.4 | 30.0 |
| 79 | 90.0 | 60.7 |
| 80 | <5 | |
| 81 | <5 | |
| 82 | 87.4 | 58.2 |
| 83 | 34.0 | |
| 84A | 92.9 | 54.3 |
| 84B | | |
| 84C | 47.8 | 29.6 |
| 84D | 27.8 | <5 |
| 84E | 11.7 | 6.1 |
| 84F | 87.4 | 52.4 |
| 84G | 92.0 | 63.0 |
| 84H | >95 | 67.0 |
| 84I | >95 | 82.7 |
| 84J | 93.3 | 40.4 |
| 84K | >95 | 90.8 |
| 84L | >95 | 55.2 |
| 84M | >95 | 80.9 |
| 84N | 92.8 | 81.4 |
| 84O | <5 | <5 |
| 85 | >95 | 82.4 |
| 86 | >95 | >95 |
| 87 | >95 | 84.2 |
| 88 | >95 | 88.4 |
| 89 | 48.4 | 21.5 |
| 90 | 78.2 | 86.3 |
| 91 | 6.6 | 16.4 |
| 92 | >95 | 81.5 |
| 93 | >95 | 66.3 |
| 94 | >95 | >95 |
| 95 | >95 | >95 |
| 96 | >95 | >95 |
| 97 | >95 | 86.4 |
| 98 | >95 | 81.4 |
| 99 | >95 | >95 |
| 100 | 93.0 | 93.9 |
| 101 | >95 | >95 |
| 102 | 93.3 | 91.9 |
| 103 | >95 | 88.7 |
| 104 | >95 | 92.4 |
| 105 | >95 | 92.4 |
| 106 | >95 | 92.8 |
| 107 | >95 | >95 |
| 108 | >95 | >95 |
| 109 | 64.2 | 65.8 |
| 110 | 90.9 | 90.7 |
| 111 | >95 | >95 |
| 112 | >95 | >95 |
| 113 | >95 | >95 |
| 114 | >95 | >95 |
| 115 | 93.3 | 76.1 |
| 116 | >95 | >95 |
| 117 | >95 | >95 |
| 118 | >95 | >95 |
| 119 | 56.2 | 20.1 |
| 120 | 58.9 | 22.2 |
| 121 | >95 | 87.4 |
| 122A | 88.2 | 55.0 |
| 122B | >95 | 92.3 |
| 122C | >95 | >95 |
| 122D | >95 | >95 |
| 122E | >95 | >95 |
| 122F | >95 | >95 |
| 122G | >95 | 92.1 |
| 122H | >95 | >95 |

TABLE 1-continued

| Example number | PIM1 % I at 0.3 uM | PIM2 % I at 0.3 uM |
|---|---|---|
| 122I | >95 | >95 |
| 122J | >95 | >95 |
| 122K | >95 | >95 |
| 122L | >95 | >95 |
| 122M | >95 | >95 |
| 122N | >95 | >95 |
| 122O | >95 | >95 |
| 122P | >95 | >95 |
| 122Q | >95 | >95 |
| 122R | >95 | 89.6 |
| 122S | >95 | >95 |
| 122T | >95 | >95 |
| 122U | >95 | >95 |
| 122V | >95 | >95 |
| 122W | >95 | >95 |
| 122X | >95 | 67.1 |
| 122Y | >95 | >95 |
| 122Z | >95 | >95 |
| 122AA | >95 | >95 |
| 122AB | >95 | >95 |
| 122AC | >95 | >95 |
| 122AD | >95 | >95 |
| 122AE | >95 | >95 |
| 122AF | 83.9 | 87.9 |
| 122AG | 68.9 | 86.7 |
| 122AH | 19.0 | 14.0 |
| 122AI | >95 | >95 |
| 123 | >95 | >95 |
| 124 | >95 | >95 |
| 125 | >95 | >95 |
| 126 | >95 | >95 |
| 127 | >95 | >95 |
| 128 | 81.2 | 49.0 |
| 129A | >95 | >95 |
| 129B | >95 | >95 |
| 129C | 85.0 | 52.1 |
| 130 | 66.2 | 45.5 |
| 131A | 27.1 | <5 |
| 131B | <5 | <5 |
| 132 | 93.0 | 88.1 |
| 133 | >95 | 93.4 |
| 134 | >95 | 85.2 |
| 135 | 42.5 | 10.8 |
| 136 | 82.8 | 44.6 |
| 137 | 55.1 | 18.6 |
| 138 | 87.9 | 63.2 |
| 139 | 58.1 | 15.1 |
| 140 | 73.3 | 52.0 |
| 141 | 34.9 | <5 |
| 142 | 86.1 | 75.2 |
| 143 | 85.9 | 49.8 |
| 144 | 63.2 | 21.2 |
| 145 | >95 | 80.1 |
| 146 | 88.9 | 48.5 |
| 147 | 74.3 | 36.4 |
| 148 | 91.5 | 60.8 |
| 149 | >95 | 75.4 |
| 150 | 79.8 | 31.7 |
| 151 | 31.5 | 13.5 |
| 152 | 10.8 | 16.7 |

The invention claimed is:

1. A compound, or a pharmaceutically acceptable salt thereof, wherein the compound has the structure:

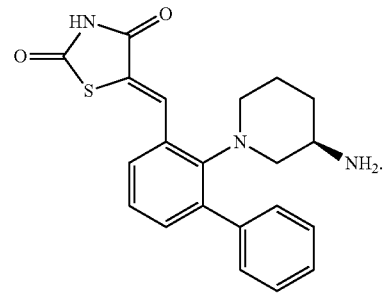 [SMILES: N[C@@H]1CCCN(c2c(/C=C3\SC(=O)NC3=O)cccc2-c2ccccc2)C1]

2. The compound of claim 1.
3. A pharmaceutically acceptable salt of the compound of claim 1.
4. The pharmaceutically acceptable salt of claim 3, wherein the pharmaceutically acceptable salt is the hydrochloride salt of the compound having the structure:

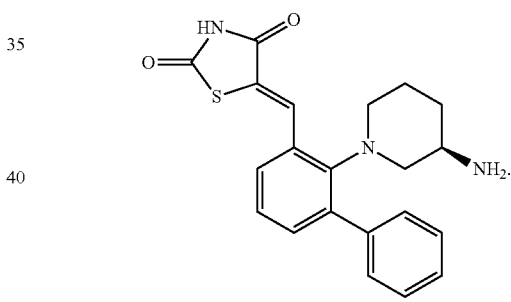

5. A pharmaceutical composition comprising the compound of claim 1, or a pharmaceutically acceptable salt thereof, and a physiological acceptable carrier or excipient.

* * * * *